United States Patent [19]

Akahoshi et al.

[11] Patent Number: 5,750,545
[45] Date of Patent: May 12, 1998

[54] TRIAZOLE DERIVATIVE AND PHARMACEUTICAL USE THEREOF

[75] Inventors: Fumihiko Akahoshi; Takehiro Okada; Shinji Takeda; Youichiro Naito; Chikara Fukaya; Shigeki Kuwahara; Masahiko Kajii; Hiroko Nishimura; Masanori Sugiura, all of Osaka, Japan

[73] Assignee: The Green Cross Corporation, Osaka, Japan

[21] Appl. No.: 586,787

[22] PCT Filed: Jul. 22, 1994

[86] PCT No.: PCT/JP94/01215

§ 371 Date: Jan. 23, 1996

§ 102(e) Date: Jan. 23, 1996

[87] PCT Pub. No.: WO95/03286

PCT Pub. Date: Feb. 2, 1995

[30] Foreign Application Priority Data

| Jul. 23, 1993 | [JP] | Japan | 5-182522 |
| Jul. 23, 1993 | [JP] | Japan | 5-182544 |
| Aug. 4, 1993 | [JP] | Japan | 5-193460 |

[51] Int. Cl.⁶ ............ C07D 249/14; C07D 487/04; A61K 31/41; A61K 31/53

[52] U.S. Cl. ............ 514/340; 514/383; 514/384; 546/272.4; 548/263.8; 548/264.8; 548/265.2; 548/265.6

[58] Field of Search ............ 546/272.4; 548/263.8, 548/264.8, 265.2, 265.6; 514/340, 383, 384

[56] References Cited

U.S. PATENT DOCUMENTS

5,135,928 8/1992 Reiter et al. ............ 514/233.2

FOREIGN PATENT DOCUMENTS

| 434982 | 7/1991 | European Pat. Off. | 548/265.6 |
| 2-235055 | 9/1990 | Japan . | |
| 3-209371 | 9/1991 | Japan . | |
| 4-507249 | 12/1992 | Japan . | |

Primary Examiner—Richard L. Raymond
Attorney, Agent, or Firm—Sughrue, Mion, Zinn, Macpeak & Seas, PLLC

[57] ABSTRACT

An agent for the prophylaxis and treatment of immune-related diseases, in particular, immunosuppressant, an agent for the prophylaxis and treatment of allergic diseases, an agent for the prophylaxis and treatment of eosinophil-related diseases and an eosinophilia inhibitor, comprising, as an active ingredient, a series of triazole derivatives of the following formula (I)

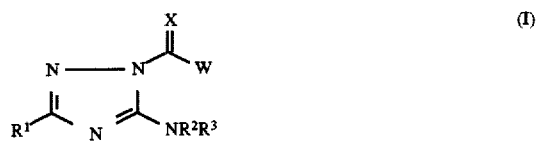

(I)

or the following formula (III)

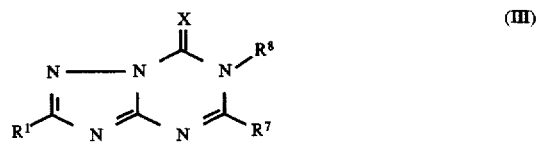

(III)

wherein each symbol is as defined in the specification, or a pharmaceutically acceptable salt thereof. A novel monocyclic or bicyclic triazole derivative. The agent for the prophylaxis and treatment of immune-related diseases, in particular, immunosuppressant, the agent for the prophylaxis and treatment of allergic diseases, the agent for the prophylaxis and treatment of eosinophil-related diseases, the eosinophilia inhibitor and the novel triazole derivative of the present invention all, have superior eosinophilia-inhibitory action and lymphocyte activation-inhibitory action. They are low toxic and persistent in action. They are particularly effective in the treatment of accumulation and activation of eosinophil and lymphocytes, inflammatory respiratory tract diseases, eosinophil-related diseases such as eosinophilia, and immune-related diseases.

17 Claims, No Drawings

TRIAZOLE DERIVATIVE AND PHARMACEUTICAL USE THEREOF

This application is a 371 of PCT/JP94/01215, filed Jul. 22, 1994.

1. Technical Field

The present invention relates to novel pharmaceutical use of a series of triazole derivatives and to novel triazole derivatives. More particularly, the present invention relates to an agent for the prophylaxis and treatment of immune-related diseases, which has eosinophilia-inhibitory action, lymphocytes activation-inhibitory action and the like, and to novel triazole derivatives.

2. Background Art

A typical condition of immune-related diseases is immune sthenia such as allergic diseases, and for the prevention and treatment thereof, there have been widely used bronchodilators and antiallergic agents.

An allergic disease is associated with, besides the reactions mainly of mastocytes and basocytes, increase and activation of eosinophil and activation of lymphocytes, by which, it has been clarified, inflammation is induced which causes chronic conditions of the disease. Accordingly, suppression of the disease upon development of an eosinophilia inhibitor and immunosuppressant has been considered.

In a typical allergic reaction, chemical transmitters such as histamin, leukotriene and PAF (platelet activating factor) and various enzymes are released from mastocytes and basocytes by the degranulation due to the invasion of an extraneous factor (allergen). At the same time, the lymphocytes, upon recognition of the allergen, produce various lymphokines which cause wandering, activation and growth of inflammatory cells (mainly eosinophil). These induce an inflammation which gives damages to the tissues, thus causing allergic diseases. The patients with such allergic diseases have been rapidly increasing in number, attracting much social attention, and various methods have been applied for the prophylaxis and treatment of the diseases. However, they are hardly sufficient in terms of effects and side-effects. Meanwhile, the action mechanism of the allergic reaction has been intensively studied, and the reports in recent years have clarified the deep involvement of the activation of, in the main, eosinophil and lymphocytes, and various factors released therefrom, in the onset of the disease. For example, it has been gradually clarified that type III and type IV allergies cause, besides type I allergic reaction, symptoms of bronchial asthma, and that inflammation of respiratory tract is present as a basic symptom. In fact, humectation and activation of eosinophil and lymphocytes have been observed on the air duct mucosa in bronchial asthma, thus suggesting the deep involvement of eosinophil and lymphocytes in the mechanism that makes the disease chronic.

Eosinocytes generally occupy 1–3% of the leukocytes in peripheral blood. An allergic disease such as allergic rhinitis and bronchial asthma, or vermination causes numerous emergence of eosinophil in the topical lesion and blood. Eosinophilia is a hematological pathic phenomenon found when allergic diseases and verminous diseases are contracted, wherein eosinophil occupies 6% or more of peripheral blood leukocytes. Eosinophilia is known to occur in various diseases, besides the above-mentioned allergic diseases and vermination, such as dermal diseases (e.g. herpes zoster, hives, psoriasis and eczema), haematopoietic diseases (e.g. myelocytic leukemia and pernicious anemia), various epidemic (e.g. cholera and malaria) and various osteopathic diseases (e.g. sarcoma, rachitis and myelitis). In allergic diseases such as asthma, moreover, the activation of lymphocytes has been found to play an important role prior to eosinophilia. That is, lymphokines produced by lymphocytes act on various inflammatory cells and cause wandering, activation and growth of inflammatory cells. In addition, lymphocytes exert important actions in various immune diseases as well, besides eosinophil.

Accordingly, a substance having inhibitory actions on eosinophilia and lymphocyte activation is expected to be effective in the treatment of accumulation and activation of eosinophil and lymphocytes caused by allergen, the treatment of inflammatory air duct diseases, and the treatment of eosinophilia, eosinophil-related diseases (e.g., eosinophilic enterogastritis, Hynel syndrome, atopic dermatitis, hives, allergic rhinitis and allergic conjunctivitis) and immune-related diseases.

It is therefore an object of the present invention to provide an agent for the prophylaxis and treatment of immune-related diseases, in particular, immunosuppressant, an agent for the prophylaxis and treatment of allergic diseases, an agent for the prophylaxis and treatment of eosinophil-related diseases, an eosinophilia inhibitor and a novel compound, all having eosinophilia-inhibitory action and lymphocyte activation-inhibitory action.

DISCLOSURE OF THE INVENTION

The present inventors have found that the above-mentioned objects can be accomplished by the present invention.

That is, the present invention firstly relates to an agent for the prophylaxis and treatment of immune-related diseases, in particular, immunosuppressant, an agent for the prophylaxis and treatment of allergic diseases, an agent for the prophylaxis and treatment of eosinophil-related diseases and an eosinophilia inhibitor, which comprise, as an active ingredient, a triazole derivative of the following formula

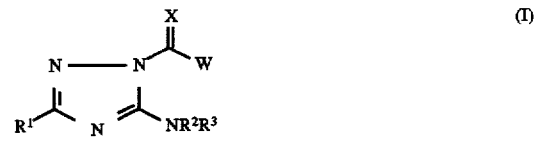

(I)

wherein

X is an oxygen atom or a sulfur atom;

W is $-NR^4R^5$ or $-SR^6$;

$R^1$ is a hydrogen atom, a lower alkyl, $-NR^{10}R^{11}$, $-N=R^{13}$ or a group of the formula (II)

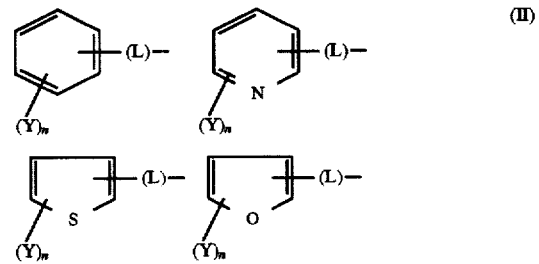

(II)

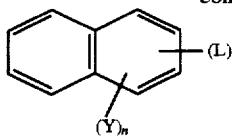

wherein Y is a hydrogen atom, a lower alkyl, a lower alkoxy, a halogen, a cyano, a nitro, a lower alkyl substituted by halogen, —NR$^{14}$R$^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and R$^2$ and R$^3$ are the same or different and each is a hydrogen atom or a lower alkyl;

wherein R$^4$ and R$^5$ are the same or different and each is a hydrogen atom, an optionally substituted lower alkyl, cycloalkyl, a phenyl or —(CH$_2$)$_m$COOR$^{16}$, R$^{16}$ is a hydrogen atom or a lower alkyl, m is an integer of 1 to 6, R$^6$ is a lower alkyl, R$^{10}$ and R$^{11}$ are the same or different and each is a hydrogen atom, an optionally substituted benzoyl, an optionally substituted phenyl, a lower alkylcarbonyl or —COCOOR$^{17}$, R$^{17}$ is a lower alkyl, R$^{13}$ is an optionally substituted methylene, R$^{14}$ and R$^{15}$ are the same or different and each is a hydrogen atom, a lower alkyl, —COCOOR$^{17}$ or —CSNHR$^{18}$, and R$^{18}$ is a lower alkyl, or a pharmaceutically acceptable salt thereof.

The present invention also relates to an agent for the prophylaxis and treatment of immune-related diseases, in particular, immunosuppressant, an agent for the prophylaxis and treatment of allergic diseases, an agent for the prophylaxis and treatment of eosinophil-related diseases and an eosinophilia inhibitor, which comprise, as an active ingredient, a triazole derivative of the formula (I) wherein R$^1$ is a group of the formula (II), or a pharmaceutically acceptable salt thereof.

Secondly, the present invention relates to an agent for the prophylaxis and treatment of immune-related diseases, in particular, immunosuppressant, an agent for the prophylaxis and treatment of allergic diseases, an agent for the prophylaxis and treatment of eosinophil-related diseases and an eosinophilia inhibitor, which comprise, as an active ingredient, a bicyclic triazole derivative of the formula (III)

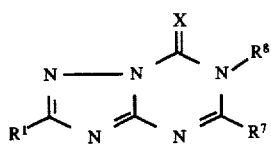 (III)

wherein

X is an oxygen atom or a sulfur atom;

R$^1$ is a hydrogen atom, a lower alkyl, —NR$^{10}$R$^{11}$, —N=R$^{13}$ or a group of the formula (II)

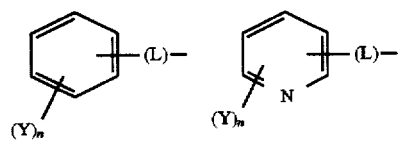 (II)

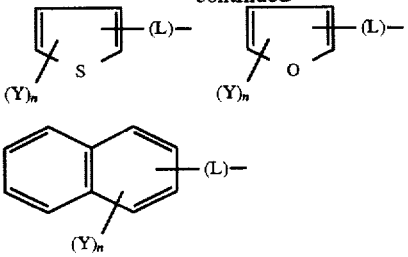

wherein Y is a hydrogen atom, a lower alkyl, a lower alkoxy, a halogen, a cyano, a nitro, a lower alkyl substituted by halogen, —NR$^{14}$R$^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different;

R$^7$ is a hydrogen atom, a lower alkyl or an optionally substituted phenyl; and R$^8$ is a hydrogen atom, a lower alkyl, an optionally substituted phenyl or —(CH$_2$)$_m$COOR$^{16}$, wherein R$^{10}$ and R$^{11}$ are the same or different and each is a hydrogen atom, an optionally substituted benzoyl, an optionally substituted phenyl, a lower alkylcarbonyl or —COCOOR$^{17}$, R$^{17}$ is a lower alkyl, R$^{13}$ is an optionally substituted methylene, R$^{14}$ and R$^{15}$ are the same or different and each is a hydrogen atom, a lower alkyl, —COCOOR$^{17}$ or —CSNHR$^{18}$, R$^{18}$ is a lower alkyl, R$^{16}$ is a hydrogen atom or a lower alkyl and m is an integer of 1 to 6, or a pharmaceutically acceptable salt thereof.

The present invention relates to an agent for the prophylaxis and treatment of immune-related diseases, in particular, immunosuppressant, an agent for the prophylaxis and treatment of allergic diseases, an agent for the prophylaxis and treatment of eosinophil-related diseases and an eosinophilia inhibitor, which comprise, as an active ingredient, the above-mentioned bicyclic triazole derivative of the formula (III) wherein R$^1$ is a group of the formula (II), or a pharmaceutically acceptable salt thereof.

Thirdly, the present invention relates to triazole derivatives of the formula (I')

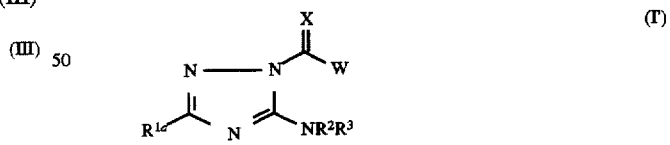 (I')

wherein

X is an oxygen atom or a sulfur atom;

W is —NR$^{4a}$R$^{5a}$ or —SR$^6$;

R$^{1a}$ is —NR$^{10}$R$^{11}$, —N=R$^{13}$ or a group of the formula (II)

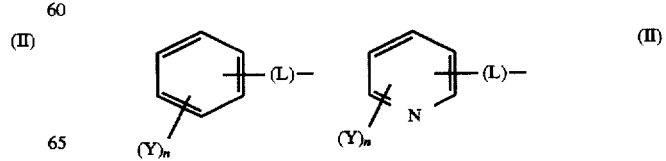 (II)

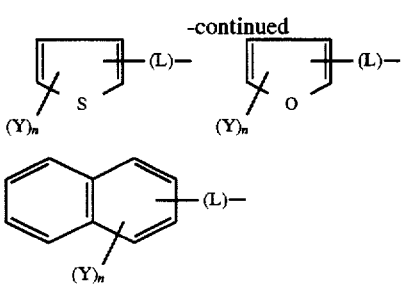

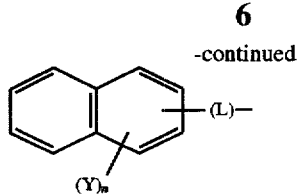

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl, wherein $R^{4a}$ and $R^{5a}$ are the same or different and each is a hydrogen atom, a lower alkyl or —$(CH_2)_mCOOR^{16}$, $R^{16}$ is a hydrogen atom or a lower alkyl, m is an integer of 1 to 6, provided that $R^{4a}$ and $R^{5a}$ are not hydrogen atom at the same time, $R^6$ is a lower alkyl, $R^{10}$ and $R^{11}$ are the same or different and each is a hydrogen atom, an optionally substituted benzoyl, an optionally substituted phenyl, a lower alkylcarbonyl or —$COCOOR^{17}$, $R^{17}$ is a lower alkyl, provided that when all of $R^2$, $R^3$ and $R^{4a}$ are hydrogen atom and $R^{5a}$ is a lower alkyl, $R^{10}$ and $R^{11}$ are not hydrogen atom at the same time, $R^{13}$ is an optionally substituted methylene, $R^{14}$ and $R^{15}$ are the same or different and each is a hydrogen atom, a lower alkyl, —$COCOOR^{17}$ or —$CSNHR^{18}$ and $R^{18}$ is a lower alkyl, or a pharmaceutically acceptable salt thereof.

Fourthly, the present invention relates to bicyclic triazole derivatives of the formula (III)

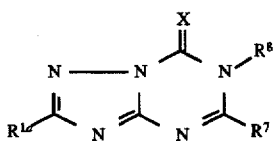 (III)

wherein

X is an oxygen atom or a sulfur atom;

$R^{1a}$ is —$NR^{10}R^{11}$, —$N=R^{13}$ or a group of the formula (II)

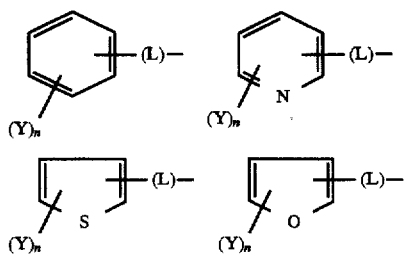 (II)

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene and n is an integer of 1 to 3, provided that when n is 2 or 3, Y may be the same or different;

$R^7$ is a hydrogen atom, a lower alkyl or an optionally substituted phenyl; and $R^8$ is a hydrogen atom, a lower alkyl, an optionally substituted phenyl or —$(CH_2)_mCOOR^{16}$, wherein $R^{10}$ and $R^{11}$ are the same or different and each is a hydrogen atom, an optionally substituted benzoyl, an optionally substituted phenyl, a lower alkylcarbonyl or —$COCOOR^{17}$, $R^{17}$ is a lower alkyl, $R^{13}$ is an optionally substituted methylene, $R^{14}$ and $R^{15}$ are the same or different and each is a hydrogen atom, a lower alkyl, —$COCOOR^{17}$ or —$CSNHR^{18}$, $R^{18}$ is a lower alkyl, $R^{16}$ is a hydrogen atom or a lower alkyl and m is an integer of 1 to 6, and pharmaceutically acceptable salts thereof.

The present invention also relates to a method for the prophylaxis and treatment of immune-related diseases, in particular, eosinophil-related diseases, comprising the use of the compound of the formula (I) or (III).

The present invention further relates to use of the compound of the formula (I) or (III) for the preparation of an agent for the prophylaxis and treatment of immune-related diseases, in particular, eosinophil-related diseases.

The symbols used in the present specification are explained in the following.

Lower alkyl at Y, $R^1$–$R^8$, $R^{14}$–$R^{18}$, $R^{1a}$, $R^{4a}$ and $R^{5a}$ may be linear or branched and preferably has 1 to 7 carbon atoms. Specific examples include methyl, ethyl, propyl, isopropyl, n-butyl, isobutyl, t-butyl, n-pentyl, n-hexyl, 2-methylpropyl, 1,1-dimethylpropyl and 1,2,2-trimethylpropyl.

Lower alkoxy at Y may be linear or branched and preferably has 1 to 6 carbon atoms. Examples thereof include methoxy, ethoxy, propoxy, isopropoxy, butoxy, isobutoxy, t-butoxy, pentyloxy and hexyloxy.

Halogen at Y is fluorine, chlorine, bromine or iodine.

Lower alkyl substituted by halogen at Y may be linear or branched and preferably has 1 to 7 carbon atoms. Examples thereof include trifluoromethyl, trichloromethyl and dibromoethyl.

Alkylene at L preferably has 1 to 5 carbon atoms, and examples thereof include methylene, ethylene, propylene, trimethylene, tetramethylene and pentamethylene.

Cycloalkyl at $R^4$ and $R^5$ has 3 to 10, preferably 3 to 7 carbon atoms, and is exemplified by cyclopropyl, cyclobutyl, cyclopentyl, cyclohexyl and cycloheptyl.

As regards the optionally substituted lower alkyl at $R^4$ and $R^5$, examples thereof include those mentioned above. Examples of the substituent include halogen, hydroxy and lower alkoxy. Note that halogen and lower alkoxy may be exemplified by those exemplified above.

The lower alkyl moiety of lower alkylcarbonyl at $R^{10}$ and $R^{11}$ include those exemplified above. Specific examples of lower alkylcarbonyl include methylcarbonyl, ethylcarbonyl, propylcarbonyl, butylcarbonyl and pentylcarbonyl.

The substituent on optionally substituted phenyl at Y, $R^7$, $R^8$, $R^{10}$ and $R^{11}$ and optionally substituted benzoyl at $R^{10}$ and $R^{11}$ is exemplified by lower alkyl, lower alkoxy, halogen and lower alkyl substituted by halogen, all of which are the same as those exemplified above.

The substituent on optionally substituted methylene at $R^{13}$ is exemplified by di-lower alkylamino, lower alkoxy and optionally substituted phenyl. Note that the substituent on lower alkyl, lower alkoxy and optionally substituted phenyl may be exemplified by those mentioned above.

The position of the substituent Y on the group of the formula (II) in $R^1$ and $R^{10}$ a is not particularly limited.

The production methods of the triazole derivatives of the present invention are explained in the following.

An ester compound (A) of the formula

   (A)

wherein $R^{1'}$ is a group of the formula (II')

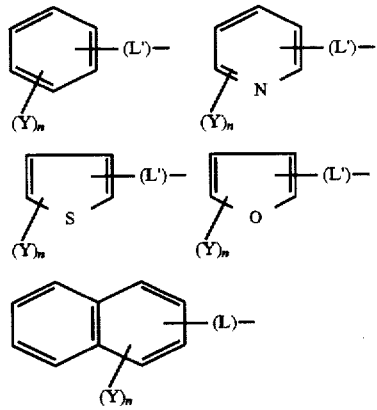   (II')

wherein Y and n are as defined above, L' is a direct bond, alkylene, vinylene or ethynylene and $R^{20}$ is a lower alkyl which is the same as the above-mentioned, can be produced by the following four methods.

(1) Synthesis from related carboxylic acid compound (B)—(Method 1)

A compound of the formula

   (B)

wherein $R^{1'}$ is as defined above, is reacted according to the method of R. O. Clinton et al [J. Am. Chem. Soc., 70, 3135 (1948)]; that is, a carboxylic acid compound (B) and 0.1–0.5 fold equivalent of an acid catalyst such as sulfuric acid are reacted in a mixed solvent of an excess of an alcohol such as methanol, dichloromethane and 1,2-dichloroethane, at room temperature to 80° C. for about 1 to 24 hours to give a compound of the formula (A).

(2) Synthesis from related carboxylic acid compound (B)—(Method 2)

The compound of the formula (B) is reacted with 1–3 fold equivalents of a base such as sodium hydride in a solvent system of tetrahydrofuran or dimethylformamide at 0° C. to room temperature for about 30 minutes to 3 hours to give a sodium salt of carboxylic acid compound (B), which is followed by the addition of 2–3 fold equivalents of an alkyl halide of the formula (C)

   (C)

wherein $R^{20}$ is as defined above and Z is a halogen such as chlorine and bromine to allow reaction at room temperature to 100° C. for about 30 minutes to 24 hours to give a compound of the formula (A). When the substituent on $R^{1'}$ has a hydroxy the compound can be converted to a related lower alkoxy by this method.

(3) Synthesis from substituted nitrile compound—(Method 3)

A compound of the formula (D)

   (D)

wherein $R^{1'}$ is as defined above, in a solvent such as methanol and ethanol, is added with the same solvent containing 1.0–1.5 fold equivalents of hydrogen chloride, and the mixture is reacted at a temperature from room temperature to the refluxing temperature for about 1–24 hours to give a compound of the formula (A). When methanol is used as a solvent, $R^{20}$ in the formula (A) is methyl, and when ethanol is used, $R^{20}$ is ethyl.

(4) Synthesis from substituted acid anhydride—(Method 4)

An acid anhydride of the formula (E)

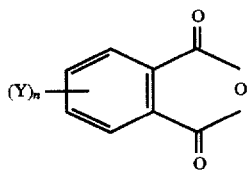   (E)

wherein Y and n are as defined above, and an excess of a solvent such as methanol and ethanol are reacted at a temperature from room temperature to the refluxing temperature for about 1–24 hours to give a compound of the formula (A).

While the formula (E) shows a substituted benzoic anhydride, other compounds having aromatic ring are also treated in the same manner.

The obtained ester compound (A) is converted to a hydrazide compound (F) of the formula

   (F)

wherein $R^{1'}$ is as defined above, by the following method.

The conversion to a hydrazide compound is carried out by the method of M. Bergman et al [J. Biol. Chem., 113, 341 (1936)]; that is, an ester compound (A) is reacted with 1–3 fold equivalents of hydrazine or hydrazine monohydrate in a solvent such as water and ethanol at a temperature from room temperature to the refluxing temperature for about 1–24 hours to give a compound of the formula (F).

Then, an amidinohydrazide compound (G) of the formula

   (G)

wherein $R^{1'}$ is as defined above, is obtained from the hydrazide compound (F) by the method reported by C. A. Lipinski et al [J. Med. Chem., 281, 628 (1985)].

That is, the hydrazide compound (F) is reacted with 1–3 fold equivalents of methylisothiourea sulfate in an aqueous solution of 1–3 fold equivalents of sodium hydroxide, or using methanol as a co-solvent where necessary, at a temperature from room temperature to the refluxing temperature for about 1–48 hours to give an amidinohydrazide compound of the formula (G).

The compound of the formula (G) can be also synthesized by the following method.

That is, a carboxylic acid compound of the formula (B) is reacted with 1.0–1.3 fold equivalents of thionyl chloride and an excess of dimethylformamide in a solvent such as dichloromethane and chloroform at room temperature to 70° C. for about 30 minutes to 24 hours to give a corresponding acid chloride compound (H) of the formula

wherein $R^{1'}$ is as defined above.

The obtained acid chloride compound (H), 2–5 fold equivalents of a salt such as aminoguanidine hydrochloride and 2–5 fold equivalents of a base such as sodium hydroxide are reacted to give an amidinohydrazide compound (G).

The amidinohydrazide compound is then heated at 200°–260° C. for about 10 minutes to 6 hours for ring closure to give an aminotriazole of the formula (J)

wherein $R^1$ is as defined above, in which $R^1$ is the above-mentioned $R^{1'}$.

The compound of the formula (J) wherein $R^1$ is $R^{1'}$ can be also synthesized by the following method.

That is, an ester compound of the formula (A), 2–6 fold equivalents of sodium alkoxide such as sodium methoxide prepared from sodium metal and methanol, and a salt compound such as aminoguanidine hydrochloride are reacted in a solvent such as dry methanol at a temperature from room temperature to the refluxing temperature for about 1–24 hours to give a compound of the formula (J) wherein $R^1$ is $R^{1'}$.

In addition, a compound of the formula (J) wherein $R^1$ is $R^{1'}$ can be also obtained by the method reported by K. R. Huffman et al [J. Org. Chem., 28, 1816 (1963)] and B. T. Heitke et al [J. Org. Chem., 39, 1522 (1974)].

That is, an orthoester of the formula (W)

$$R^{1'}(OR^{21})_3 \quad (W)$$

wherein $R^{1'}$ is as defined above and $R^{21}$ is lower alkyl which is the same as the above-mentioned, one fold equivalent of cyanamide and 2 fold equivalents of acetic anhydride are reacted at 130°–140° C. for about 1–5 hours to give a corresponding ester, N-cyanoimidate (X) of the formula

wherein $R^{1'}$ and $R^{21}$ are as defined above. The obtained ester, N-cyanoimidate (X) is reacted with 1–2 fold equivalents of hydrazine in an organic solvent such as acetonitrile at room temperature to 50° C. for 1–24 hours to give a compound of the formula (J) wherein $R^1$ is $R^{1'}$.

The above-mentioned compound of the formula (J) wherein $R^1$ is a group of the formula (II) and L is an oxygen atom is synthesized by the method of R. L. Webb et al [J. Heterocyclic. Chem., 19, 1205(1982)].

That is, 1.0–1.5 equivalents of hydrazine is added to substituted diphenylcyanocarbonimidate in an alcohol solvent such as methanol and the mixture is reacted at 0° C. to room temperature for about 30 minutes to 5 hours to give a compound of the formula (J) wherein $R^1$ is a group of the formula (II) and L is an oxygen atom.

The compound of the formula (J) wherein $R^1$ is —$NR^{1'}R^{11'}$ wherein $R^{10'}$ and $R^{11'}$ are each hydrogen atom or an optionally substituted phenyl is obtained by reacting a substituted aromatic amine of the formula $$R^{10'}R^{11'}NH \quad (K)$$

wherein $R^{10'}$ and $R^{11'}$ are as defined above, with 1.0–1.2 fold equivalents of diphenylcyanocarbonimidate in an alcohol solvent such as 2-propanol at 0° C. to room temperature for about 30 minutes to 5 hours to give an N-substituted aromatic—N'-cyano-O-phenylisourea (L) of the formula $$R^{10'}R^{11'}NC(=NCN)OPh \quad (L)$$

wherein $R^{10'}$ and $R^{11'}$ are as defined above and Ph is phenyl.

Using the obtained urea compound (L), a compound of the formula (J) wherein $R^1$ is —$NR^{10'}R^{11'}$ wherein $R^{10'}$ and $R^{11'}$ are as defined above can be obtained by the same method for synthesizing a compound of the formula (J) wherein $R^1$ is a group of the formula (II) and L is an oxygen atom.

The compound of the above-mentioned formula (J) wherein $R^1$ is a group of the formula (II) and L is a sulfur atom can be obtained by reacting 3-amino-5-mercapto-1H-1,2,4-triazole with 1.0–1.2 fold equivalents of a base such as sodium hydride in a solvent such as dimethyl sulfoxide and dimethylformamide to give a sodium salt, which is reacted with a halogenated substituted aromatic compound of the formula (M)

wherein Y, Z and n are as defined above, at room temperature to 150° C. for about 1 hour to 48 hours.

Of the compounds of the formula (J), a compound wherein $R^1$ is a group of the formula (II) and Y is amino, —$NHCOCOOR^{17}$ or tetrazolyl can be obtained after converting Y to nitro or cyano by any of the reactions exemplified below.

For example, when nitro is converted to amino, a nitro compound is reacted in a solvent such as methanol with 1–50 wt % of 10% palladium-carbon as a catalyst under a hydrogen atmosphere at room temperature for about 1–48 hours to give an amino compound.

The obtained amino compound is reacted with 1.0–1.1 fold equivalents of an acid chloride such as alkyloxalyl chloride and 1.0–1.1 fold equivalents of a base such as triethylamine in a solvent such as dimethylformamide at $-70°$ C. to room temperature for about 30 minutes to 5 hours to give a —$NHCOCOOR^{17}$ compound.

When a tetrazolyl compound is obtained from the cyano compound, the cyano compound is reacted in the presence of 5–10 fold equivalents of sodium azide and pyridinium chloride in a solvent such as dimethylformamide and dimethyl sulfoxide under reflux with heating for about 1 to 48 hours.

A compound of the formula (O)

wherein $R^1$, $R^2$ and $R^3$ are as defined above, is obtained by reacting a compound wherein the 3-position amino of an aminotriazole compound (J) is substituted with a chlorine atom, with a compound of the formula (P)

$$HNR^2R^3 \quad (P)$$

wherein $R^2$ and $R^3$ are as defined above, in an autoclave at 150°–200° C. for 1–48 hours.

An aminotriazole compound (J) or a compound (O) is converted to a triazole derivative of the formula (I)

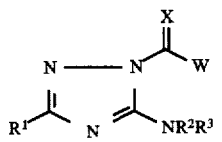

wherein $R^1$, $R^2$, $R^3$, X and W are as defined above, wherein X is a sulfur atom and W is —$NR^4R^5$ as in the following. That is, the above-mentioned aminotriazole compound (J) or a compound (O) is reacted with an alkyl isothiocyanate of the formula (Q)

$$R^{22}-N=C=S \qquad (Q)$$

wherein $R^{22}$ is $R^4$ or $R^5$ wherein $R^4$ and $R^5$ are as defined above, in a solvent such as dimethylformamide, dimethyl sulfoxide and pyridine, or by using sodium hydroxide as a base in a mixed solvent of water and tetrahydrofuran, at room temperature to 60° C. for about 1–200 hours. The alkyl isothiocyanate (Q) used here can be also prepared by the method of J. E. Hodgkins et al [J. Org. Chem., 29, 3098 (1964)].

The conversion to a triazole derivative of the formula (I) wherein X is a sulfur atom and W is —$NR^4R^5$ is also carried out by reacting the above-mentioned triazole compound (J) or a compound (O) with alkylthiocarbamoyl chloride of the formula (R)

$$\underset{\underset{Cl-C-NR^4R^5}{\|}}{S} \qquad (R)$$

wherein $R^1$ and $R^5$ are as defined above, in pyridine at room temperature to 60° C. for about 1–48 hours.

Of the compounds of the formula (I) obtained here, a compound wherein $R^1$ is amino can be synthesized using 3,5-diamino-1H-1,2,4-triazole as an aminotriazole compound. The compound can be converted to an amide compound wherein $R^1$ is lower alkylcarbonylamide, optionally substituted benzoylamide or —$NHCOCOOR^{17}$, or an optionally substituted methylideneamino compound such as dimethylaminomethylideneamino, ethoxymethylideneamino and N-substituted benzylideneamino by the following method.

The conversion to a lower alkylcarbonylamide or an optionally substituted benzoylamide is respectively carried out by reacting a compound of the formula (I) wherein $R^1$ is amino, with 1–3 fold equivalents of a lower alkyl carboxylic anhydride of the formula (V)

$$\underset{R^{23}COCR^{23}}{\overset{O\ \ O}{\|\ \ \|}} \qquad (V)$$

wherein $R^{23}$ is lower alkyl which is the same as the above-mentioned, or a substituted benzoic anhydride of the formula (Y)

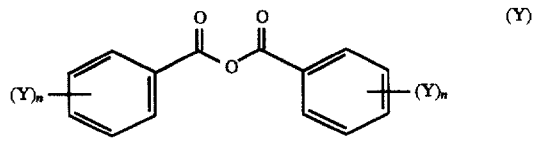

wherein Y and n are as defined above, in pyridine as a solvent at 0° C. to room temperature for about 1–100 hours.

The conversion to a compound wherein $R^1$ is —$NHCOCOOR^{17}$ is carried out by reacting a compound of the formula (I) wherein $R^1$ is amino with 1–3 fold equivalents of alkyloxalyl chloride in a solvent such as pyridine and dimethylformamide at 0° C. to room temperature for about 1–5 hours.

The conversion to a compound wherein $R^1$ is dimethylaminomethylideneamino or alkoxymethylideneamino is respectively carried out by reacting a compound of the formula (I) wherein $R^1$ is amino with an excess of dimethylformamide, 1.0–2.0 fold equivalents of a base such as triethylamine, 1.0–2.0 equivalents of acid chloride such as benzoyl chloride or an excess of dialkoxymethyl acetate at 0° C. to room temperature for about 30 minutes to 5 hours.

The conversion to a compound wherein $R^1$ is N-substituted benzylideneamino is carried out by reacting a compound of the formula (I) wherein $R^1$ is amino with 1.0–2.0 fold equivalents of substituted aromatic aldehyde, using an acid catalyst such as DL-camphor-10-sulfonic acid in ethanol at a temperature from room temperature to the refluxing temperature for about 1–24 hours.

Of the compounds of the formula (I), the conversion to an alkyl dithiocarbonate of the formula (S)

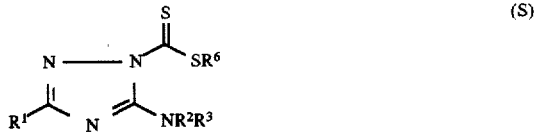

wherein $R^1$, $R^2$, $R^3$ and $R^6$ are as defined above, thiocarbonylaminoalkylcarboxylic acid alkyl ester of the formula (T)

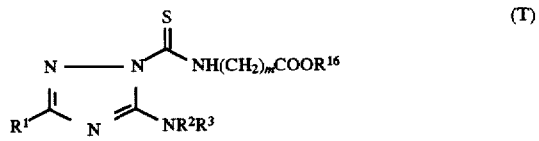

wherein $R^1$, $R^2$, $R^3$, $R^{16}$ and m are as defined above, or thiocarbonylaminoalkylcarboxylic acid of the formula (U)

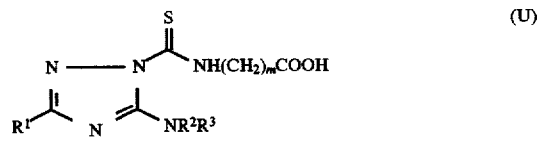

wherein $R^1$, $R^2$, $R^3$ and m are as defined above, is respectively carried out by the method of L. Pongo et al [J. Heterocyclic. Chem. 27, 1249 (1990)] or J. Barkoczy et al [J. Heterocyclic. Chem. 28, 1597 (1991)].

That is, using triazole compound (J) or compound (O) prepared by the above-mentioned method, 1–2 fold equivalents of carbon disulfide, 1.0–1.5 fold equivalents of a base such as potassium hydroxide, a solvent such as dimethylformamide and 1–2 fold equivalents of alkyl iodide, the reaction is performed at 0° C. to room temperature for about 1–10 hours to give an alkyl dithiocarbonate (S).

Using the obtained alkyl dithiocarbonate (S), a solvent such as methanol, 1.0–1.3 fold equivalents of a base such as sodium methoxide, and 1.0–1.3 fold equivalents of aminoalkylcarboxylic acid alkyl ester hydrochloride, the reaction is performed at a temperature from room temperature to heat-refluxing temperature for about 1–4 hours to give a thiocarbonylaminoalkylcarboxylic acid alkyl ester (T).

The obtained ester compound (T) is reacted in 1.0–1.3 fold equivalents of an aqueous solution of alkali such as sodium hydroxide or a co-solvent of phosphate buffer and acetonitrile, using hydrolase such as swine liver esterase at room temperature to 50° C. for about 30 minutes to 15 days to give a thiocarbonylaminoalkylcarboxylic acid (U).

A triazole derivative (I) wherein X is a sulfur atom can be produced by the above method. When X is an oxygen atom, the above-mentioned triazole compound (J) or compound (O) is reacted with a compound of the formula (Z)

$$R^{22}-N=C=O \qquad (Z)$$

wherein $R^{22}$ is as defined above, in the same manner as above for synthesis.

In addition, the above-mentioned triazole compound (J) or compound (O) is reacted with alkylcarbamoyl chloride of the formula

$$\begin{array}{c} O \\ \| \\ Cl-C-NR^4R^5 \end{array} \qquad (Z\text{-}1)$$

wherein $R^1$ and $R^5$ are as defined above, in pyridine at room temperature to 60° C. for about 1–48 hours, to give a triazole derivative (I) wherein X is an oxygen atom.

The compound of the above-mentioned formula (I) is added with an excess of diethoxymethyl acetate to allow reaction at room temperature to 120° C. for about 1–24 hours to give a bicyclic triazole derivative of the formula (III)

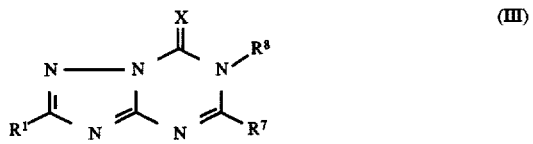

wherein $R^1$, $R^7$, $R^8$ and X are as defined above, in which $R^7$ is a hydrogen atom.

Using an orthoester of the formula (Z-2)

$$R^7C(OR^{21})_3 \qquad (Z\text{-}2)$$

wherein $R^7$ and $R^{21}$ are as defined above, instead of diethoxymethyl acetate and a catalytic amount of acetic acid as necessary, a reaction is carried out at room temperature to 160° C. for about 1–24 hours to give a bicyclic triazole derivative of the formula (III).

In the above-mentioned synthesis method, when the substituent Y on $R^1$ is amino, hydroxy or carboxyl, the reaction is carried out using, as necessary, a group easily protected, deprotected or converted. Specifically, nitro or acetylamino is used in the case of amino; methoxyethoxymethyl is used in the case of hydroxy; and ester is used in the case of carboxyl.

A series of triazole derivatives thus produced can be obtained at optional purities by appropriately using known separation and purification methods such as concentration, extraction, chromatography, reprecipitation and recrystallization. The series of triazole derivatives can be converted to pharmaceutically acceptable salts by a known method. Said triazole derivatives have a basic group and can be converted to acid addition salts, which are exemplified by salts with inorganic acid such as hydrochloride, hydrobromide, phosphate and sulfate, and salts with organic acid such as acetate, succinate, maleate, fumarate, malate and tartrate.

As the series of triazole derivatives and acid addition salts thereof, preferred compounds are 5-amino-1-[methylamino (thiocarbonyl)]-1H-1,2,4-triazole, 3,5-diamino-1-[methylamino(thiocarbonyl)]-1H-1,2,4-triazole, 5-amino-3-(4-cyanophenyl)-1-[methylamino(thiocarbonyl)]-1H-1,2,4-triazole, 5-amino-3-(4-chlorophenyl)-1-[methylamino (thiocarbonyl)]-1H-1,2,4-triazole, 5-amino-3-(4-methoxyphenyl)-1-[methylamino(thiocarbonyl)]-1H-1,2,4-triazole, 6-methyl-1,2,4-triazolo[1,5-a]-1,3,5-triazine-7(6H) -thione, 2-(4-cyanophenyl)-6-methyl-1,2,4-triazolo[1,5-a]-1,3,5-triazine-7(6H)-thione, 2-(4-chlorophenyl)-6-methyl-1, 2,4-triazolo[1,5-a]-1,3,5-triazine-7(6H)-thione, 5-amino-3-(3-chlorophenyl)-1-[methylamino(thiocarbonyl)]-1H-1,2,4-triazole, 5-amino-3-(4-fluorophenyl)-1-[methylamino (thiocarbonyl)]-1H-1,2,4-triazole, 5-amino-3-(4-bromophenyl)-1-[methylamino(thiocarbonyl)]-1H-1,2,4-triazole, 5-amino-1-[methylamino(thiocarbonyl)]-3-(4-trifluoromethylphenyl)-1H-1,2,4-triazole, 5-amino-3-(4-phenylphenyl)-1-[methylamino(thiocarbonyl)]-1H-1,2,4-triazole, 5-amino-3-(2,4-dichlorophenyl)-1-[methylamino (thiocarbonyl)]-1H-1,2,4-triazole, 5-amino-3-(3,4-dichlorophenyl)-1-[methylamino(thiocarbonyl)]-1H-1,2,4-triazole, 5-amino-3-(4-chloro-2-methoxyphenyl)-1-[methylamino(thiocarbonyl)]-1H-1,2,4-triazole, 2-(4-fluorophenyl)-6-methyl-1,2,4-triazolo[1,5-a]-1,3,5-triazine-7(6H)-thione, 2-(4-bromophenyl)-6-methyl-1,2,4-triazolo [1,5-a]-1,3,5-triazine-7(6H)-thione, 6-methyl-2-(4-trifluoromethylphenyl)-1,2,4-triazolo[1,5-a]-1,3,5-triazine-7(6H)-thione, 6-methyl-2-(4-phenylphenyl)-1,2,4-triazolo [1,5-a]-1,3,5-triazine-7(6H)-thione, 2-(2,4-dichlorophenyl)-6-methyl-1,2,4-triazolo [1,5-a]-1,3,5-triazine-7(6H)-thione, 2-(3,4-dichlorophenyl)-6-methyl-1,2,4-triazolo[1,5-a]-1,3, 5-triazine-7(6H)-thione, and acid addition salts thereof.

The series of the triazole derivatives and acid addition salts thereof of the present invention have eosinophilia-inhibitory action and lymphocyte activation-inhibitory action in mammals such as mouse, rat, rabbit, dog, cat and human; are extremely low toxic; and show persistent action since they reside for a long time in blood. Accordingly, they are useful as an agent for the prophylaxis and treatment of immune-related diseases, in particular, immunosuppressant, an agent for the prophylaxis and treatment of allergic diseases, an agent for the prophylaxis and treatment of eosinophil-related diseases or an eosinophilia inhibitor. They are particularly effective in the treatment of accumulation and activation of eosinophil and lymphocytes, inflammatory air duct diseases, eosinophil-related diseases such as eosinophilia, and immune-related diseases.

When the series of the triazole derivatives and acid addition salts thereof are used as the above-mentioned pharmaceutical products, they are admixed with pharmacologically acceptable additives such as carrier, excipient and diluent, as well as pharmaceutically necessary ingredients as appropriate, after which the mixture is formulated into pharmaceutical compositions such as powder, granule, tablet, capsule, syrup, injection and the like, which can be orally or parenterally administered. They can be also administered topically, or as an external agent or inhalant.

The above-mentioned preparations contain an effective amount of the series of triazole derivatives or acid addition salts thereof. While the dose varies depending on the administration route, symptom, and body weight and age of patients, when the preparation is orally administered to an adult, for example, the dose is 0.05–100 mg/day, particularly 1–30 mg/day, which is preferably administered once or in several doses. In the case of intravenous administration, the dose is 0.05–5 mg/day, particularly 0.1–2 mg/day, which is preferably administered once or in several doses.

The present invention is explained in more detail in the following by illustrative examples, to which the present invention is not limited.

EXAMPLE 1

5-Amino-1-[methylamino(thiocarbonyl)]-3-phenyl-1H-1,2,4-triazole (1) Benzoic acid 2-amidinohydrazide A solution of benzoic acid hydrazide (10.3 g), methylisothiourea sulfate (21.0 g), sodium hydroxide (3.12 g) and water (150 ml) was stirred for 99 hours at room temperature. The resulting solid was collected by filtration and washed with water to give 8.28 g of a white solid (yield 61%).

$^1$H-NMR (DMSO-d$_6$) δ: 6.7–7.2 (4H, m), 7.26–7.35 (3H, m), 7.9–8.0 (2H,m), 10.6 (1H, brs)

(2) 3-Amino-5-phenyl-1H-1,2,4-triazole

The compound (8.28 g) obtained in (1) above was heated for 20 minutes at 220° C. to give 6.81 g of white crystals (yield 91%). Melting point: 179°–180° C.

IR (KBr): 3340, 3130, 2990, 2930, 2880, 2090, 1664, 1600, 1581 cm$^{-1}$ $^1$H-NMR (DMSO-d$_6$) δ: 5.96(2H, brs), 7.34 (1H, t, J=7.2 Hz), 7.40 (2H, t, J=7.2 Hz), 7.88 (2H, d, J=7.2 Hz), 12.1 (1H, brs)

(3) 5-Amino-1-[methylamino(thiocarbonyl)]-3-phenyl-1H-1,2,4-triazole

To a solution of the compound (2.60 g) obtained in (2) above in dimethylformamide (20 ml) was added methyl isothiocyanate (1.44 g). The mixture was stirred for 13 hours at room temperature, poured into water, and extracted with ethyl acetate. The extract was dried over magnesium sulfate, and the solvent was distilled away under reduced pressure. The residue was chromatographed on silica gel (chloroform-methanol) to give 1.34 g of a white solid (yield 35%). The solid was recrystallized from chloroform to give 980 mg of white crystals.

Melting point: 174°–175° C.

IR (KBr): 3300, 3070, 1638, 1521 cm$^{-1}$ $^1$H—NMR (DMSO-d$_6$) δ: 3.10 (3H, d, J=4.7 Hz), 7.47–7.52 (3H, m), 8.03–8.07 (2H, m), 8.31 (2H, brs), 10.03 (1H, d, J=4.7 Hz)

EXAMPLE 2

5-Amino-3-(4-cyanophenyl)-1-[methylamino(thiocarbonyl)]-1H-1,2,4-triazole (1) 4-Cyanobenzoic acid hydrazide To a solution of methyl 4-cyanobenzoate (155 g) and ethanol (300 ml) was gradually added dropwise hydrazine monohydrate (71 ml) with stirring. The mixture was stirred at room temperature for 22 hours. The resulting crystals were collected by filtration and washed with ethanol to give 125 g of a white solid (yield 81%).

IR (KBr): 3300, 3050, 2240, 1705, 1640, 1620, 1535 cm$^{-1}$ $^1$H-NMR (DMSO-d$_6$) δ: 4.62 (2H, brs), 7.96 (4H, s), 10.1 (1H, brs)

(2) 4-Cyanobenzoic acid 2-amidinohydrazide

The synthesis was carried out according to the method of Example 1-(1). The compound (112 g) obtained in (1) above, methanol (1100 ml), water (550 ml), methylisothiourea sulfate (387 g) and sodium hydroxide (55.6 g) were used as reagents. The mixture was stirred for 23 hours at 70° C. to give 79.4 g of a yellow solid (yield 56%).

IR (KBr): 3400, 2240, 1650, 1580, 1520 cm$^{-1}$ $^1$H-NMR (DMSO-d$_6$) δ: 6.71 (2H, brs), 7.01 (2H, brs), 7.72 (2H, d, J=8.3 Hz), 8.12 (2H, d, J=8.3 Hz), 10.0–10.5 (1H, m)

(3) 3-Amino-5-(4-cyanophenyl)-1H-1,2,4-triazole

The synthesis was carried out according to the method of Example 1-(2). The compound (78.9 g) obtained in (2), above was used as a reagent and reacted for 3 hours at 240° C. to give 65.5 g of a yellow solid (yield 91%).

IR (KBr): 3380, 3250, 3130, 2220, 1660, 1600, 1585, 1560, 1520 cm$^{-1}$ $^1$H-NMR (DMSO-d$_6$) δ: 6.21 (2H, brs), 7.86 (2H, d, J=8.4 Hz), 8.03 (2H, d, J=8.4 Hz), 12.4 (1H, brs)

(4) 5-Amino-3-(cyanophenyl)-1-[methylamino(thiocarbonyl)]-1H-1,2,4-triazole

The synthesis was carried out according to the method of Example 1-(3). The compound (38.0 g) obtained in (3) above, methyl isothiocyanate (43.5 g) and dimethylformamide (275 ml) were used as reagents. After the reaction, the mixture was chromatographed on silica gel (hexane-ethyl acetate) to give 3.36 g of a yellow solid (yield 6.3%). The solid was recrystallized from chloroform-hexane to give 2.2 g of yellow crystals.

Melting point: 213°–216° C. (decomposition)

IR (KBr): 3250, 2220, 1650, 1530 cm$^{-1}$ $^1$H-NMR (DMSO-d$_6$) δ: 3.09 (3H, d, J=3.9 Hz), 7.99 (2H, d, J=8.4 Hz), 8.19 (2H, d, J=8.4 Hz), 8.40 (2H, brs), 10.1–10.2 (1H, brs)

EXAMPLE 3

5-Amino-1-[methylamino(thiocarbonyl)]-3-(p-tolyl)-1H-1,2,4-triazole (1) p-Toluic acid 2-amidinohydrazide The synthesis was carried out according to the method of Example 1-(1). p-Toluic acid hydrazide (5.66 g), methylisothiourea sulfate (10.5 g), sodium hydroxide (1.57 g) and water (250 ml) were used as reagents. The mixture was reacted at room temperature to give 2.20 g of white crystals (yield 30%).

Melting point: 196°–198° C.

IR (KBr): 3480, 3360, 3220, 3040, 1678, 1634, 1583, 1523 cm$^{-1}$ $^1$H-NMR (DMSO-d$_6$) δ: 2.30 (3H, s), 6.81 (4H, brs), 7.08 (2H, d, J=8.0 Hz), 7.81 (2H, d, J=8.0 Hz), 10.67 (1H, brs)

(2) 3-Amino-5-(p-tolyl)-1H-1,2,4-triazole

The synthesis was carried out according to the method of Example 1-(2). The compound (2.18 g) obtained in (1) above was used as a reagent to give 1.89 g of a white solid (yield 96%).

Melting point: 201°–203° C.

IR (KBr): 3430, 3340, 3230, 3040, 2880, 1627, 1584, 1540 cm$^{-1}$ $^1$H-NMR (DMSO-d$_6$) δ: 2.33 (3H, s), 5.99 (2H, brs), 7.19 (2H, d, J=8.1 Hz), 7.77 (2H, d, J=8.1 Hz), 11.95 (1H, brs)

(3) 5-Amino-1-[methylamino(thiocarbonyl)]-3-(p-tolyl)-1H-1,2,4-triazole

The synthesis was carried out according to the method of Example 1-(3). The compound (1.33 g) obtained in (2) above, methyl isothiocyanate (2.07 g) and dimethylformamide (6 ml) were used as reagents. After the reaction, the mixture was chromatographed on silica gel (chloroform-methanol) to give 1.17 g of a white solid (yield 62%). The solid was recrystallized from chloroform-hexane to give 819 mg of colorless transparent crystals.

Melting point: 188°–190° C.

IR (KBr): 3320, 3070, 1641, 1528, 1500 cm$^{-1}$ $^1$H-NMR (DMSO-d$_6$) δ: 2.36 (3H, s), 3.09 (3H, s), 7.30 (2H, d, J=8.0 Hz), 7.94 (2H, d, J=8.1 Hz), 8.28 (2H, brs), 9.99 (1H, brs)

EXAMPLE 4

5-Amino-3-(4-chlorophenyl)-1-[methylamino(thiocarbonyl)]-1H-1,2,4-triazole (1) 4-Chlorobenzoic acid 2-amidinohydrazide The synthesis was carried out according to the method of Example 1-(1). 4-Chlorobenzoic acid hydrazide (34.8 g), methylisothiourea sulfate (115.4 g), sodium hydroxide (17.1 g), water (440 ml) and methanol (700 ml) were used as reagents. The mixture was stirred for 4 days at 60° C. to give 45.4 g of a pale-brown solid which was a mixture of a hydrazide compound and the objective compound.

$^1$H-NMR (DMSO-d$_6$) δ: 6.72 (2H, brs), 6.88 (2H, brs), 7.31 (2H, d, J=8.6 Hz), 7.95 (2H, d, J=8.6 Hz)

(2) 3-Amino-5-(4-chlorophenyl)-1H-1,2,4-triazole

The synthesis was carried out according to the method of Example 1-(2). The mixture (45.4 g) obtained in (1) above was used as a reagent and chromatographed on silica gel (chloroform-methanol) to give 16.0 g of white crystals (yield 41% from 4-chlorobenzoic acid hydrazide).

Melting point: 190°–195° C.

IR (KBr): 3430, 3080, 1643, 1590, 1576 cm$^{-1}$ $^1$H-NMR (DMSO-d$_6$) δ: 6.07 (2H, brs), 7.45 (2H, d, J=8.6 Hz), 7.88 (2H, d, J=8.6 Hz), 12.10 (1H, brs)

(3) 5-Amino-3-(4-chlorophenyl)-1-[methylamino (thiocarbonyl)]-1H-1,2,4-triazole

The synthesis was carried out according to the method of Example 1-(3). The compound (18.6 g) obtained in (2) above, methyl isothiocyanate (10.0 g) and dimethylformamide (50 ml) were used as reagents. After the reaction, the mixture was chromatographed on silica gel (chloroform-methanol) to give 11.4 g of a white solid (yield 45%). The solid was recrystallized from chloroform to give white crystals.

Melting point: 199°–201° C.

IR (KBr): 3270, 3070, 1635, 1520 cm$^{-1}$ $^1$H-NMR (DMSO-d$_6$) δ: 3.09 (3H, s), 7.57 (2H, d, J=8.4 Hz), 8.04 (2H, d, J=8.4 Hz), 8.32 (2H, brs), 10.05 (1H, brs)

EXAMPLE 5

5-Amino-3-(3-chlorophenyl)-1-[methylamino (thiocarbonyl)]-1H-1,2,4-triazole (1) 3-Chlorobenzoic acid hydrazide The synthesis was carried out according to the method of Example 2-(1). Methyl 3-chlorobenzoate (31.1 g), ethanol (50 ml) and hydrazine monohydrate (17 ml) were used as reagents. After the reaction, ether was added to the reaction mixture to allow precipitation to give 27.8 g of a white solid (yield 92%).

IR (KBr): 3450, 3320, 3050, 1960, 1665 cm$^{-1}$ $^1$H-NMR (DMSO-d$_6$) δ: 4.52(2H, brs), 7.49(1H, t, J=8.0 Hz), 7.59(1H, dt, J=8.0, 1.5 Hz), 7.78(1H, dt, J=8.0, 1.5 Hz), 7.85(1H, t, J=1.5 Hz), 9.91(1H, brs)

(2) 3-Chlorobenzoic acid 2-amidinohydrazide

The synthesis was carried out according to the method of Example 1-(1). The compound (26.3 g) obtained in (1) above, methylisothiourea sulfate (85.7 g), sodium hydroxide (12.3 g), water (350 ml) and methanol (250 ml) were used as reagents. The mixture was stirred for 28 hours at 60° C. to give 19.6 g of a pale-yellow solid (yield 60%).

IR (KBr): 3300, 3220, 1660, 1630, 1600, 1510 cm$^{-1}$ $^1$H-NMR (DMSO-d$_6$) δ: 7.09–7.71(6H, m), 7.87(1H, d, J=7.3 Hz), 7.98(1H, s),8.75–10.95(1H, brs)

(3) 3-Amino-5-(3-chlorophenyl)-1H-1,2,4-triazole

The synthesis was carried out according to the method of Example 1-(2). The compound (5.18 g) obtained in (2) above was used as a reagent to give 4.61 g of a pale-yellow solid (yield 97%).

IR (KBr): 3020, 2850, 2350, 1700, 1640, 1560 cm$^{-1}$ $^1$H-NMR (DMSO-d$_6$) δ: 7.40–7.52(2H, m), 7.84(1H, d, J=5.0, 1.5 Hz),7.88(1H, t, J=1.5 Hz)

(4) 5-Amino-3-(3-chlorophenyl)-1-[methylamino (thiocarbonyl)]-1H-1,2,4-triazole

The synthesis was carried out according to the method of Example 1-(3). The compound (3.09 g) obtained in (3) above, methyl isothiocyanate (4.82 g), dimethyl sulfoxide (15 ml) were used as reagents. After the reaction, the mixture was chromatographed on silica gel (hexane-ethyl acetate) and recrystallized from ethyl acetate to give 1.04 g of white crystals (yield 24%).

Melting point: 191°–92° C.

IR (KBr): 3450, 3300, 1640, 1520 cm$^{-1}$ $^1$H-NMR (DMSO-d$_6$) δ: 3.09(3H, m), 7.47–7.60(2H, m), 7.90–8.03(1H, m), 8.03–8.13(1H, m), 8.37(2H, brs), 10.02–10.21 (1H, m)

EXAMPLE 6

5-Amino-3-(2-chlorophenyl)-1-[methylamino (thiocarbonyl)]-1H-1,2,4-triazole (1) 2-Chlorobenzoic acid 2-amidinohydrazide The synthesis was carried out according to the method of Example 1-(1). 2-Chlorobenzoic acid hydrazide (25.2 g), methylisothiourea sulfate (82.4 g), sodium hydroxide (11.9 g), methanol (200 ml) and water (200 ml) were used as reagents. The mixture was stirred at 60° C. for 32 hours to give 25.2 g of a white solid (yield 80%).

IR (KBr): 3270, 3200, 3150, 2750, 1695, 1665, 1630, 1590 cm$^{-1}$ $^1$H-NMR (DMSO-d$_6$) δ: 7.31–7.53(3H, m), 7.66(4H, brs), 7.77(1H, d, J=7.3 Hz), 8.5–11.3(1H, brs) (2) 3-Amino-5-(2-chlorophenyl)-1H-1,2,4-triazole The synthesis was carried out according to the method of Example 1-(2). The compound (5.36 g) obtained in (1) above was used as a reagent and reacted for 1.5 hours at 230° C. to give 4.36 g of a pale-yellow solid (yield 89%).

IR (KBr): 3320, 2750, 1690, 1600 cm$^{-1}$ $^1$H-NMR (DMSO-d$_6$) δ: 6.95(2H, brs), 7.46–7.65(3H, m), 7.73–7.80(1H, m)

(3) 5-Amino-3-(2-chlorophenyl)-1-[methylamino (thiocarbonyl)]-1H-1,2,4-triazole

The synthesis was carried out according to the method of Example 1-(3). The compound (1.6 g) obtained in (2) above, dimethylformamide (10 ml), methyl isothiocyanate (2.65 g) were used as reagents. After the reaction, water was added to the reaction mixture and the mixture was extracted with ethyl acetate. The extract was dried over magnesium sulfate. The solvent was distilled away under reduced pressure. The residue was chromatographed on silica gel (hexane-ethyl acetate), and recrystallized from ethyl acetate to give 675 mg of pale-yellow crystals (yield 31%).

Melting point: 168°–170° C.

IR (KBr): 3300, 3090, 1645, 1600, 1520 cm$^{-1}$ $^1$H-NMR (DMSO-d$_6$) δ: 3.07(3H, d, J=4.7 Hz), 7.38–7.64 (3H, m), 7.80–7.90(1H, m), 8.35(2H, brs), 9.80–10.10(1H, m)

EXAMPLE 7

5-Amino-3-(4-fluorophenyl)-1-[methylamino (thiocarbonyl)]-1H-1,2,4-triazole (1) Methyl 4-fluorobenzoate A solution of 4-fluorobenzoic acid (25.0 g), 1,2-dichloroethane (120 ml), methanol (21.7 ml) and concentrated sulfuric acid (0.8 ml) was stirred for 16.5 hours with refluxing. After the reaction, the reaction mixture was poured into a saturated aqueous sodium hydrogencarbonate solution, extracted with chloroform, and washed with saturated brine. The mixture was dried over magnesium sulfate, and the solvent was distilled away under reduced pressure to give 23.0 g of a colorless transparent liquid (yield 84%).

IR (Neat): 3100, 3000, 1730 cm$^{-1}$ $^1$H-NMR (CDCl$_3$) δ: 3.91(3H, s), 7.00–7.20(2H, m), 8.00–8.10(2H, m)

(2) 3-Amino-5-(4-fluorophenyl)-1H-1,2,4-triazole

Sodium methoxide was prepared from dry methanol (200 ml) and metallic sodium (6.0 g) according to a conventional method. Aminoguanidine nitrate (35.6 g) was added to this solution under ice-cooling, and a solution of the compound (10.0 g) obtained in (1) above in methanol (50 ml) was dropwise added. The resulting solution was stirred for 18 hours with refluxing, poured into ice-water, and adjusted to pH 3–4 with 3N hydrochloric acid. The resulting powder was collected by filtration, washed with water, and dried to give 9.56 g of a pale-yellow solid (yield 83%).

IR (KBr): 3600, 2950, 1720, 1600, 1500 cm$^{-1}$ $^1$H-NMR (DMSO-d$_6$) δ: 7.43(2H, t, J=90 Hz), 7.99(2H, dd, J=9.0, 6.0 Hz)

(3) 5-Amino-3-(4-fluorophenyl)-1-[methylamino(thiocarbonyl)]-1H-1,2,4-triazole

To the compound (200 mg) obtained in (2) above and a 1N aqueous sodium hydroxide solution (1.1 ml) was added a solution of methyl isothiocyanate (90 mg) in tetrahydrofuran (3 ml), and the mixture was stirred for 1 hour at room temperature. The mixture was neutralized with 1N hydrochloric acid, extracted with ethyl acetate, dried over magnesium sulfate, and concentrated. The residue was chromatographed on silica gel (chloroform), and recrystallized from chloroform to give 130 mg of white crystals (yield 46%).

Melting point: 192°–194° C.

IR (KBr): 3350, 3250, 3050, 1640, 1600, 1520, 1500 cm$^{-1}$ $^1$H-NMR (DMSO-d$_6$) δ: 3.09(3H, s), 7.35(2H, t, J=8.8 Hz), 8.08(2H, dd, J=8.0,6.0 Hz), 8.35(2H, brs), 10.1(1H, brs)

EXAMPLE 8

5-Amino-3-(4-bromophenyl)-1-[methylamino(thiocarbonyl)]-1H-1,2,4-triazole (1) Methyl 2-bromobenzoate The synthesis was carried out according to the method of Example 7-(1). 4-Bromobenzoic acid (25.0 g), 1,2-dichloroethane (120 ml), methanol (21.7 ml) and concentrated sulfuric acid (0.8 ml) were used as reagents to give 22.4 g of a white solid (yield 84%).

IR (KBr): 3100, 3000, 1735 cm$^{-1}$ $^1$H-NMR (CDCl$_3$) δ: 3.91(3H, s), 7.5–7.65(2H, m), 7.85–7.92(2H, m)

(2) 3-Amino-5-(4-bromophenyl)-1H-1,2,4-triazole

The synthesis was carried out according to the method of Example 7-(2). The compound (25.0 g) obtained in (1) above, methanol (250 ml), metallic sodium (6.40 g) and aminoguanidine hydrochloride (30.8 g) were used as reagents to give 9.56 g of a white solid (yield 96%).

$^1$H-NMR (DMSO-d$_6$) δ: 6.09(2H, brs), 7.59(2H, d, J=8.6 Hz), 7.75(2H, d, J=8.6 Hz) (3) 5-Amino-3-(4-bromophenyl)-1-[methylamino(thiocarbonyl)]-1H-1,2,4-triazole The synthesis was carried out according to the method of Example 7-(3). The compound (15.0 g) obtained in (2) above, a 1N aqueous sodium hydroxide solution (69.0 ml), methyl isothiocyanate (6.90 g) and tetrahydrofuran (30 ml) were used as reagents. After the reaction, the mixture was chromatographed on silica gel (chloroform), and recrystallized from chloroform to give 3.43 g of white crystals (yield 17%).

Melting point: 210°–212° C.

IR (KBr): 1630, 1595, 1515, 1500 cm$^{-1}$ $^1$H-NMR (DMSO-d$_6$) δ: 3.08(3H, d, J=2.1 Hz), 7.72(2H, d, J=8.5 Hz), 7.97(2H, d, J=8.5 Hz), 8.35(2H, brs), 9.83–10.20(1H, m)

EXAMPLE 9

5-Amino-1-[methylamino(thiocarbonyl)]-3-(4-trifluoromethylphenyl)-1H-1,2,4-triazole (1) 3-Amino-5-(4-trifluoromethylphenyl)-1H-1,2,4-triazole The synthesis was carried out according to the method of Example 7-(2). Methyl 4-trifluoromethylbenzoate (9.40 g), methanol (180 ml), metallic sodium (4.20 g) and aminoguanidine nitrate (25.3 g) were used as reagents to quantitatively give a white solid.

IR (KBr): 3400, 3300, 3100, 1695 cm$^{-1}$ $^1$H-NMR (DMSO-d$_6$) δ: 7.95(2H, d, J=8.6 Hz), 8.14(2H, d, J=8.6 Hz) (2) 5-Amino-1-[methylamino(thiocarbonyl)]-3-(4-trifluoromethylphenyl)-1H-1,2,4-triazole The synthesis was carried out according to the method of Example 7-(3). The compound (7.00 g) obtained in (1) above, a 1N aqueous sodium hydroxide solution (30.7 ml), methyl isothiocyanate (2.47 g) and tetrahydrofuran (30 ml) were used as reagents. After the reaction, the mixture was chromatographed on silica gel (chloroform), and recrystallized from chloroform to give 4.33 g of white crystals (yield 47%).

Melting point: 193°–195° C.

IR (KBr): 3300, 3000, 1645, 1520, 1500 cm$^{-1}$ $^1$H-NMR (DMSO-d$_6$) δ: 3.10(3H, s), 7.89(2H, d, J=8.2 Hz), 8.24(2H, d, J=8.2 Hz), 8.40(2H, brs), 10.2(1H, brs)

EXAMPLE 10

5-Amino-3-(4-methoxyphenyl)-1-[methylamino(thiocarbonyl)]-1H-1,2,4-triazole (1) 4-Methoxybenzoic acid hydrazide The synthesis was carried out according to the method of Example 2-(1). Methyl 4-methoxybenzoate (31.4 g), hydrazine monohydrate (58 ml) and ethanol (180 ml) were used as reagents. The mixture was reacted for 2 hours at 100° C. to give 23.1 g of a white solid (yield 74%).

IR (KBr): 3320, 3200, 3020, 2850, 1650, 1620, 1560, 1500 cm$^{-1}$ $^1$H-NMR (DMSO-d$_6$) δ: 3.79 (3H, s), 4.42 (2H, brs), 6.98 (2H, d, J=7.0 Hz), 7.80 (2H, d, J=7.0 Hz), 9.62 (1H, brs)

(2) 4-Methoxybenzoic acid 2-amidinohydrazide

The synthesis was carried out according to the method of Example 1-(1). The compound (21.5 g) obtained in (1) above, methylisothiourea sulfate (173 g), sodium hydroxide (24.9 g), water (280 ml) and methanol (100 ml) were used as reagents. The mixture was reacted at 55° C. for 24 hours, and at 90° C. for 7 hours to give 23.2 g of a white solid (yield 86%).

IR (KBr): 3400, 1655, 1615, 1595, 1520 cm$^{-1}$ $^1$H-NMR (DMSO-d$_6$) δ: 3.81 (3H, s), 6.99 (2H, d, J=8.8 Hz), 7.91 (2H, d, J=8.8 Hz), 8.14 (2H, brs), 9.88 (3H, brs)

(3) 3-Amino-5-(4-methoxyphenyl)-1H-1,2,4-triazole

The synthesis was carried out according to the method of Example 1-(2). The compound (12.5 g) obtained in (2) above was used as a reagent to give a brown solid. The resulting compound was used as it was in the next reaction.

$^1$H-NMR (DMSO-d$_6$) δ: 3.78 (3H, s), 6.11 (2H, brs), 6.96 (2H, d, J=8.8 Hz), 7.80(2H, d, J=8.8 Hz), 11.9 (1H, brs)

(4) 5-Amino-3-(4-methoxyphenyl)-1-[methylamino(thiocarbonyl)]-1H-1,2,4-triazole

The synthesis was carried out according to the method of Example 1-(3). The compound obtained in (3) above, methyl isothiocyanate (19.7 g) and dimethylformamide (20 ml) were used as reagents. After the reaction, the mixture was chromatographed on silica gel (hexane-ethyl acetate) to give 686 mg of a white solid (yield 4.4% from 4-methoxybenzoic acid 2-aminohydrazide). The solid was recrystallized from ethyl acetate to give 622 mg of white crystals.

Melting point: 188°–189° C.

IR (KBr): 3340, 3300, 3100, 1635, 1610, 1585, 1525, 1500 cm$^{-1}$ $^1$H-NMR (DMSO-d$_6$) δ: 3.08 (3H, s), 3.82 (3H, s), 7.05 (2H, d, J=7.0 Hz), 7.98 (2H, d, J=7.0 Hz), 8.31 (2H, brs), 9.99 (1H, brs)

EXAMPLE 11

5-Amino-3-(4-aminophenyl)-1-[methylamino(thiocarbonyl)]-1H-1,2,4-triazole (1) 4—Nitrobenzoic acid 2-amidinohydrazide The synthesis was carried out according to the method of Example 1-(1). 4—Nitrobenzoic acid hydrazide (75.7 g), methylisothiourea sulfate (239 g), sodium hydroxide (34.3 g), water (800 ml) and methanol (800 ml) were used as reagents. The mixture was reacted at 60° C. for 41 hours to give 81.4 g of a red-brown solid (yield 87%).

IR (KBr): 3580, 3470, 3390, 3170, 1650, 1588, 1540 cm$^{-1}$ $^1$H-NMR (DMSO-d$_6$) δ: 6.75 (2H, brs), 7.06 (2H, brs), 8.13 (2H, d, J=8.0 Hz), 8.20 (2H, d, J=8.0 Hz), 10.2 (1H, brs)

(2) 3-Amino-5-(4-nitrophenyl)-1H-1,2,4-triazole

The synthesis was carried out according to the method of Example 1-(2). The compound (80.8 g) obtained in (1) above was used as a reagent to give 68.8 g of a yellow-brown solid (yield 93%).

IR (KBr): 3390, 1646, 1573, 1527, 1513 cm$^{-1}$ $^1$H-NMR (DMSO-d$_6$) δ: 6.27 (2H, brs), 8.11 (2H, d, J=90 Hz), 8.28 (2H, d, J=90 Hz), 12.4 (1H, brs)

(3) 3-Amino-5-(4-aminophenyl)-1H-1,2,4-triazole

The compound (68 g) obtained in (2) above, methanol (2500 ml) and 10% palladium-carbon (10.2 g) were used. The mixture was stirred for 20 hours at room temperature under hydrogen. After the reaction, palladium-carbon was removed by filtration, and the solvent was distilled away under reduced pressure to give a crude product. This product was chromatographed on silica gel (chloroform-methanol) to give 51.0 g of a gray solid (yield 88%).

IR (KBr): 3410, 3300, 3200, 1640, 1607, 1532, 1504 cm$^{-1}$ $^1$H-NMR (DMSO-d$_6$) δ: 5.16 (2H, brs), 5.85 (2H, brs), 6.56 (2H, d, J=8.3 Hz), 7.54 (2H, d, J=8.3 Hz), 11.68 (1H, brs)

(4) 5-Amino-3-(4-aminophenyl)-1-[methylamino(thiocarbonyl)]-1H-1,2,4-triazole

The synthesis was carried out according to the method of Example 1-(3). The compound (3.04 g) obtained in (3) above, methyl isothiocyanate (1.39 g) and dimethylformamide (30 ml) were used as reagents. After the reaction, the mixture was chromatographed on silica gel (chloroform-methanol) to give 350 mg of a white solid (yield 8.1%). This solid was recrystallized from chloroform-hexane to give 216 mg of white crystals.

Melting point: 172°–174° C.

IR (KBr): 3400, 3300, 3190, 1604, 1518 cm$^{-1}$ $^1$H-NMR (DMSO-d$_6$) δ: 3.07 (3H, brs), 5.51 (2H, brs), 6.60 (2H, d, J=8.6 Hz), 7.71 (2H, d, J=8.6 Hz), 8.19 (2H, brs), 9.38 (1H, brs)

EXAMPLE 12

5-Amino-1-[methylamino(thiocarbonyl)]-3-[4-(3-methylthioureido)phenyl]-1H-1,2,4-triazole The synthesis was carried out according to the method of Example 1-(3). The compound (3.05 g) obtained in Example 11-(3), methyl isothiocyanate (3.22 g) and dimethylformamide (30 ml) were used as reagents. After the reaction, the mixture was chromatographed on silica gel (chloroform-methanol) to give 483 mg of a pale-brown solid (yield 8.6%). This solid was recrystallized from chloroform to give white crystals.

Melting point: 190°–192° C.

IR (KBr): 3260, 1635, 1550 cm$^{-1}$ $^1$H-NMR (DMSO-d$_6$) δ: 2.94 (3H, s), 3.09 (3H, s), 7.55 (2H, d, J=8.5 Hz), 7.86 (1H, brs), 7.97 (2H, d, J=8.5 Hz), 8.29 (2H, brs), 9.70 (1H, brs), 9.98 (1H, brs)

EXAMPLE 13

5-Amino-3-[4-(ethoxalylamino)phenyl]-1-[methylamino(thiocarbonyl)]-1H-1,2,4-triazole (1) 3-Amino-5-[4-(ethoxalylamino)phenyl]-1H-1,2,4-triazole A solution of the compound (36.9 g) obtained in Example 11-(3) in dimethylformamide (380 ml) was cooled to −70° C. Triethylamine (31 ml) was added and ethyloxalyl chloride (26 ml) was gradually added dropwise. The resulting reaction mixture was gradually heated to −10° C., and added with ice-water. The mixture was extracted with ethyl acetate, washed with water and dried over magnesium sulfate. The solvent was distilled away under reduced pressure. The residue was chromatographed on silica gel (ethyl acetate-ethanol) to give 4.0 g of a white solid (yield 6.9%).

IR (KBr): 3590, 3310, 3140, 2980, 1735, 1680, 1645, 1595, 1555 cm$^{-1}$ $^1$H-NMR (DMSO-d$_6$) δ: 1.32 (3H, t, J=7.1 Hz), 4.31 (2H, q, J=7.1 Hz), 6.07 (2H, brs), 7.77 (2H, d, J=8.7 Hz), 7.85 (2H, d, J=8.7 Hz), 10.87 (1H, brs), 12.05 (1H, brs)

(2) 5-Amino-3-[4-(ethoxalylamino)phenyl]-1-[methylamino(thiocarbonyl)]-1H-1,2,4-triazole The synthesis was carried out according to the method of Example 1-(3). The compound (4.0 g) obtained in (1) above, methyl isothiocyanate (15 g) and dimethyl sulfoxide (32 ml) were used as reagents. After the reaction, the mixture was chromatographed on silica gel (hexane-ethyl acetate) to give 1.3 g of a yellow solid (yield 26%). This solid was recrystallized from ethyl acetate to give pale-yellow crystals.

Melting point: 203°–205° C.

IR (KBr): 3300, 3050, 2970, 1730, 1700, 1640, 1615, 1595, 1530, 1500 cm$^{-1}$ $^1$H-NMR (DMSO-d$_6$) δ: 1.33 (3H, t, J=7.1 Hz), 3.09 (3H, brs), 4.32 (2H, q, J=7.1 Hz), 7.88 (2H, d, J=8.8 Hz), 8.02 (2H, d, J=8.8 Hz), 8.34 (2H, brs), 10.02 (1H, brs), 10.97 (1H, brs)

EXAMPLE 14

5-Amino-1-[methylamino(thiocarbonyl)]-3-[4-(1H-tetrazol-5-yl)phenyl]-1H-1,2,4-triazole (1) 3-Amino-5-[4-(1H-tetrazol-5-yl)phenyl]-1H-1,2,4-triazole A reaction mixture of the compound (3.26 g) obtained in Example 2-(3), dimethylformamide (75 ml), pyridine hydrochloride (17.9 g) and sodium azide (9.9 g) was stirred for 52 hours at 100° C. The reaction mixture was filtrated, and the filtrate was chromatographed on silica gel (chloroform-methanol) to give 2.40 g of a white solid (yield 63%).

IR (KBr): 3250, 3100, 2750, 1700, 1650, 1540 cm$^{-1}$ $^1$H-NMR (DMSO-d$_6$) δ: 6.14 (2H, brs), 7.97–8.14 (4H, m), 12.2 (1H, brs)

(2) 5-Amino-1-[methylamino(thiocarbonyl)]-3-[4-(1H-tetrazol-5-yl)phenyl]-1H-1,2,4-triazole The synthesis was carried out according to the method of Example 1-(3). The compound (2.18 g) obtained in (1) above, methyl isothiocyanate (1.41 g), pyridine (100 ml) and dimethylformamide (2 ml) were used as reagents. After the reaction, the mixture was chromatographed on silica gel (chloroform-methanol), and recrystallized from methanol to give 200 mg of white crystals (yield 6.6%).

Melting point: 275°–285° C. (decomposition)

IR (KBr): 3500, 3310, 3200, 3100, 2700, 1640, 1590, 1535, 1500 cm$^{-1}$ $^1$H-NMR (DMSO-d$_6$)) δ: 3.10 (3H, d, J=4.6 Hz), 8.16 (2H, d, J=8.5 Hz), 8.24 (2H, d, J=8.5 Hz), 8.38 (2H, brs), 10.1–10.2 (1H, m)

EXAMPLE 15

5-Amino-1-[methylamino(thiocarbonyl)]-3-(4-phenylphenyl)-1H-1,2,4-triazole (1) Methyl 4-phenylbenzoate The synthesis was carried out according to the method of Example 7-(1). 4-Phenylbenzoic acid (25.5 g), 1,2-dichloroethane (110 ml), methanol (50 ml) and concentrated sulfuric acid (2.5 ml) were used as reagents to give 26.3 g of a white solid (yield 96%).

IR (KBr): 1700, 1600 cm$^{-1}$ $^1$H-NMR (CDCl$_3$) δ: 3.88(3H, s), 7.36–7.60(3H, m), 7.74(2H, d, J=7.3 Hz), 7.83(2H, d, J=8.3 Hz), 8.05(2H, d, J=8.3 Hz) (2) 3-Amino-5-(4-phenylphenyl)-1H-1,2,4-triazole The synthesis was carried out according to the method of Example 7-(2). The compound (15.2 g) obtained in (1) above, methanol (220 ml), metallic sodium (6.74 g) and aminoguanidine nitrate (40.2 g) were used as reagents to give 11.1 g of a white solid (yield 66%).

IR (KBr): 3300, 2800,1620, 1520 cm$^{-1}$ $^1$H-NMR (DMSO-d$_6$) δ: 6.02(2H, brs), 7.27–7.75(4H, m), 7.92(2H, d, J=8.3 Hz), 11.8–12.5(1H, brs) (3) 5-Amino-1-[methylamino(thiocarbonyl)]-3-(4-phenylphenyl)-1H-1,2,4-triazole The synthesis was carried out according to the method of Example 7-(3). The compound (6.11 g) obtained in (2) above, a 1N aqueous sodium hydroxide solution (25.9 ml), methyl isothiocyanate (2.84 g) and tetrahydrofuran (15 ml) were used as reagents. After the reaction, the mixture was chromatographed on silica gel (chloroform), and recrystallized from chloroform to give 2.90 g of white crystals (36%).

Melting point: 275°–277° C.

IR (KBr): 3250, 3000, 1725, 1645, 1520, 1500 cm$^{-1}$ $^1$H-NMR (DMSO-d$_6$) δ: 3.10(3H, s), 7.30–7.58(3H, m), 7.75(2H, d, J=7.0 Hz),7.82(2H, d, J=8.4 Hz), 8.14(2H, d, J-8.4 Hz), 8.36(2H, brs), 10.1(1H, brs)

EXAMPLE 16

5-Amino-3-(2,4-dichlorophenyl)-1-[methylamino(thiocarbonyl)]-1H-1,2,4-triazole (1) Methyl 2,4-dichlorobenzoate The synthesis was carried out according to the method of Example 7-(1). 2,4-Dichlorobenzoic acid (25.0 g), 1,2-dichloroethane (50 ml), methanol (40 ml), concentrated sulfuric acid (2.0 ml) were used as reagents to give 24.5 g of a colorless transparent liquid (yield 91%).

IR (KBr): 3080, 2910, 1720, 1580, 1545 cm$^{-1}$ $^1$H-NMR (CDCl$_3$) δ: 3.87(3H, s), 7.57(1H, dd, J=8.4, 2.0 Hz), 7.78(1H, d, J=2.0 Hz), 7.86(1H, d, J=8.4 Hz) (2) 5-Amino-5-(2,4-dichlorophenyl)-1H-1,2,4-triazole The synthesis was carried out according to the method of Example 7-(2). The compound (10.0 g) obtained in (1) above, methanol (210 ml), sodium methoxide (10.4 g) and aminoguanidine nitrate (26.5 g) were used as reagents to give 1.45 g of a white solid (yield 13%).

IR (KBr): 3400, 3110, 1635, 1580, 1570, 1550, 1535 cm$^{-1}$

1H-NMR (DMSO-d$_6$) δ: 6.15(2H, brs), 7.40–7.52(1H, m), 7.65(1H, d, J=2.0 Hz), 7.84(1H, d, J=8.5 Hz), 12.3(1H, brs)

(3) 5-Amino-3-(2,4-dichlorophenyl)-1-[methylamino(thiocarbonyl)]-1H-1,2,4-triazole The synthesis was carried out according to the method of Example 7-(3). The compound (968 mg) obtained in (2) above, a 1N aqueous sodium hydroxide solution (4.23 ml), methyl isothiocyanate (715 mg) and tetrahydrofuran (5 ml) were used as reagents. After the reaction, the mixture was chromatographed on silica gel (chloroform), and recrystallized from chloroform to give 675 mg of white crystals (yield 35%).

Melting point: 192°–193° C. (decomposition)

IR (KBr): 3400, 3250, 1650, 1590, 1550, 1515, 1500 cm$^{-1}$ $^1$H-NMR (DMSO-d$_6$) δ: 3.07(3H, s), 7.56(1H, dd, J=8.4, 2.1 Hz), 7.77(1H, d, J=2.1 Hz), 7.90(1H, d, J=8.4 Hz), 8.36(2H, brs), 9.97(1H, brs)

EXAMPLE 17

5-Amino-3-(3,4-dichlorophenyl)-1-[methylamino(thiocarbonyl)]-1H-1,2,4-triazole (1) Methyl 3,4-dichlorobenzoate The synthesis was carried out according to the method of Example 7-(1). 3,4-Dichlorobenzoic acid (25.4 g), 1,2-dichloroethane (80 ml), methanol (40 ml) and concentrated sulfuric acid (2.0 ml) were used as reagents to give 24.6 g of a white solid (yield 79%).

IR (KBr): 3350, 1715, 1580, 1555 cm$^{-1}$ $^1$H-NMR (CDCl$_3$) δ: 3.88(3H, s), 7.81(1H, d, J=8.4 Hz), 7.91(1H, dd, J=8.4, 1.9 Hz), 8.09(1H, d, J=1.9 Hz)

(2) 3-Amino-5-(3,4-dichlorophenyl)-1H-1,2,4-triazole

The synthesis was carried out according to the method of Example 7-(2). The compound (10.2 g) obtained in (1) above, methanol (225 ml), metallic sodium (4.6 g) and aminoguanidine nitrate (27.2 g) were used as reagents to give 11.1 g of a white solid (yield 79%).

IR (KBr): 3400, 3280, 3150, 2700, 1900, 1630, 1600, 1580, 1515 cm$^{-1}$ $^1$H-NMR (DMSO-d$_6$) δ: 6.24(2H, brs), 7.68(1H, d, J=8.4 Hz), 7.84(1H, dd, J=8.4, 1.9 Hz), 8.00(1H, d, J=1.9 Hz), 12.4(1H, brs) (3) 5-Amino-3-(3,4-dichlorophenyl)-1-[methylamino(thiocarbonyl)]-1H-1,2,4-triazole The synthesis was carried out according to the method of Example 7-(3). The compound (5.15 g) obtained in (2) above, a 1N aqueous sodium hydroxide solution (22.5 ml), methyl isothiocyanate (5.12 g) and tetrahydrofuran (20 ml) were used as reagents. After the reaction, the mixture was chromatographed on silica gel (chloroform), and recrystallized, from chloroform to give 2.98 g of white crystals (yield 44%).

Melting point: 216°–218° C. (decomposition)

IR (KBr): 3250, 3000, 1660, 1520 cm$^{-1}$ $^1$H-NMR (DMSO-d$_6$) δ: 3.09(3H, s), 7.79(1H, d, J=8.4 Hz), 7.96(1H, dd, J=8.4,1.9 Hz), 8.22(1H, d, J=1.9 Hz), 8.38(2H, brs), 10.16(1H, brs)

EXAMPLE 18

5-Amino-3-(4-chloro-2-methoxyphenyl)-1-[methylamino(thiocarbonyl)]-1H-1,2,4-triazole (1) Methyl 4-chloro-2-methoxybenzoate To a suspension of 60% sodium hydride oil (3.4 g) in dimethylformamide (25 ml) was added 4-chlorosalicylic acid (7.33 g) under ice-cooling, and the mixture was stirred for 1 hour at room temperature. After the stirring, iodomethane (25 g) was dropwise added to the mixture and the mixture was reacted for 1 hour at 50° C., which was followed by extraction with ether. The extract was washed with water and dried over magnesium sulfate. After the concentration, the residue was chromatographed on silica gel (hexane-ethyl acetate) to give 6.60 g of a colorless transparent liquid (yield 77.4%).

IR (neat) δ: 2940, 1725, 1595, 1570 cm$^{-1}$ $^1$H-NMR (DMSO-d$_6$) δ: 3.79 (3H, s), 3.86 (3H, s), 7.09 (1H, d, J=8.3, 1.8 Hz), 7.25 (1H, d, J=1.8 Hz), 7.68 (1H, d, J=8.3 Hz) (2) 5-Amino-3-(4-chloro-2-methoxyphenyl)-1H-1,2,4-triazole The synthesis was carried out according to the method of Example 7-(2). The compound (6.40 g) obtained in (1) above, methanol (120 ml), metallic sodium (2.94 g) and aminoguanidine hydrochloride (14.1 g) were used as reagents to give 6.77 g of a pale-red solid (yield 94%).

IR (KBr): 3380, 3300, 3200, 2940, 1635, 1600, 1580, 1540 cm$^{-1}$ $^1$H-NMR (DMSO-d$_6$) δ: 3.92 (3H, s), 5.36 (2H, brs), 7.09 (1H, d, J=8.4 Hz), 7.20 (1H, s), 7.70–8.05 (1H, m), 12.51 (1H, brs) (3) 5-Amino-3-(4-chloro-2-methoxyphenyl)-1-[methylamino(thiocarbonyl)]-1H-1,2,4-triazole The synthesis was carried out according to the method of Example 7-(3). The compound (6.37 g) obtained in (2) above, a 0.9N aqueous sodium hydroxide solution (40 ml), methyl isothiocyanate (3.11 g), tetrahydrofuran (30 ml) were used as reagents. After the reaction, the mixture was chromatographed on silica gel (chloroform) to give 3.39 g of solid (yield 40%). This solid was recrystallized from ethyl acetate to give 1.80 g of white crystals.

Melting point: 165°–167° C. (decomposition)

IR (KBr): 3300, 3080, 1640, 1595, 1580, 1530, 1510 cm$^{-1}$ $^1$H-NMR (DMSO-d$_6$) δ: 3.07 (3H, s), 3.85 (3H, s), 7.10 (1H, dd, J=8.2, 1.9 Hz), 7.22 (1H, d, J=1.9 Hz), 7.74 (1H, d, J=8.2 Hz), 8.25 (2H, brs),9.87 (1H, brs)

EXAMPLE 19

5-Amino-3-(4-chloro-2-n-propoxyphenyl)-1-[methylamino(thiocarbonyl)]-1H-1,2,4-triazole (1) n-Propyl 4-chloro-2-n-propoxybenzoate The synthesis was carried out according to the method of Example 18-(1). 4-Chlorosalicylic acid (8.5 g), : 60% oil sodium hydride (4.5 g), n-propyl iodide (50 g), tetrahydrofuran (30 ml) and dimethylformamide (25 ml) were used as reagents. The mixture was reacted for 1 hour at 90° C. After the reaction, the mixture was chromatographed on silica gel (hexane-ethyl acetate) to give 7.63 g of a colorless transparent liquid (yield 63%).

IR (neat) δ: 2950, 2860, 1725, 1700, 1590, 1570 cm$^{-1}$ $^1$H-NMR (DMSO-d$_6$) δ: 0.80–1.10 (6H, m), 1.53 –1.86 (4H, m), 4.02 (2H, t,J=6.3 Hz), 4.18 (2H, t, J=6.5 Hz), 7.07 (1H, dd, J=8.3, 1.9 Hz), 7.21 (1H, d, J=1.9 Hz), 7.67 (1H, d, J=8.3 Hz)

(2) 5-Amino-3-(4-chloro-2-n-propoxyphenyl)-1H-1,2,4-triazole

The synthesis was carried out according to the method of Example 7-(2). The compound (7.63 g) obtained in (1) above, methanol (100 ml), metallic sodium (2.87 g) and aminoguanidine hydrochloride (13.8 g) were used as reagents to give 6.56 g of a pale-red solid (yield 83%).

IR (KBr): 3400, 3200, 2960, 2870, 1630, 1600, 1580, 1540 cm$^{-1}$ $^1$H-NMR (DMSO-d$_6$) δ: 0.95 (3H, t, J=7.3 Hz), 1.62–1.96 (2H, m), 3.80–4.40 (2H, m), 4.90–6.10 (2H, m), 7.06 (1H, d, J=8.2 Hz), 7.20 (1H, brs), 7.60–8.0 (1H, m), 11.8–12.5 (1H, m)

(3) 5-Amino-3-(4-chloro-2-n-propoxyphenyl)-1-[methylamino(thiocarbonyl)]-1H-1,2,4-triazole The synthesis was carried out according to the method of Example 7-(3). The compound (6.22 g) obtained in (2) above, a 0.9N aqueous sodium hydroxide solution (36 ml), methyl isothiocyanate (2.7 g) and tetrahydrofuran (25 ml) were used as reagents. After the reaction, the mixture was chromatographed on silica gel (chloroform), and recrystallized from ethyl acetate to give 2.06 g of white crystals (yield 26%).

Melting point: 136°–138° C. (decomposition)

IR (KBr): 3300, 3050, 2950, 2870, 1655, 1595, 1570, 1560, 1515 cm$^{-1}$ $^1$H-NMR (DMSO-d$_6$) δ: 0.97 (3H, t, J-7.4 Hz), 1.60–1.83 (2H, m), 3.07 (3H, s), 4.02 (2H, t, J=6.4 Hz), 7.08 (1H, dd, J=8.3, 1.9 Hz), 7.20 (1H, d, J=1.9 Hz), 7.71 (1Hi d, J=8.3 Hz), 8.22 (2H, brs), 9.78 (1H, brs)

EXAMPLE 20

5-Amino-3-(3,5-di-tert-butyl-4-hydroxyphenyl)-1-[methylamino(thiocarbonyl)]-1H-1,2,4-triazole (1) Methyl 3,5-di-tert-butyl-4-hydroxybenzoate To a solution of 3,5-di-tert-butyl-4-hydroxybenzoic acid (15.0 g) and triethylamine (8.36 ml) in dichloromethane (100 ml) was added dropwise thionyl chloride (4.81 ml), dimethylformamide (0.05 ml), and the mixture was stirred for 1 hour with refluxing. Methanol (20 ml) was dropwise added to the resulting reaction mixture, and the mixture was stirred for 10 minutes with refluxing. After the reaction, the organic layer was washed with 1N hydrochloric acid, a saturated aqueous sodium hydrogencarbonate solution, saturated brine, and dried over magnesium sulfate to give 15.5 g of a pale-yellow solid (yield 98%).

IR (KBr): 3550, 3400, 2950, 1700, 1600 cm$^{-1}$ $^1$H-NMR (CDCl$_3$) δ: 1.46(18H, s), 3.88(3H, s), 5.67(1H, brs), 7.90(2H, s)

(2) Methyl 3,5-di-tert-butyl-4-methoxyethoxymethoxybenzoate

To a solution of the compound (33.1 g) obtained in (1) above in tetrahydrofuran (150 ml) was gradually added dropwise 60% sodium hydride oil (5.5 g) and methoxyethoxymethyl chloride (17.1 ml) under ice-cooling, and the mixture was stirred for 2 hours with refluxing. After the reaction, the mixture was extracted with ether, wash with water, and dried over magnesium sulfate to quantitatively give a pale-brown liquid.

IR (KBr): 2900, 1720, 1600 cm$^{-1}$ $^1$H-NMR (CDCl$_3$) δ: 1.46(18H, s), 3.43(3H, s), 3.66(2H, t, J=5.0 Hz), 3.90(3H,s), 4.02(2H, t, J=5.0 Hz), 5.01(2H, s), 7.97(2H, s)

(3) 3-Amino-5-(3,5-di-tert-butyl-4-methoxyethoxymethoxyphenyl)-1H-1,2,4-triazole The synthesis was carried out according to the method of Example 7-(2). The compound (48.6 g) obtained in (1) above, methanol (300 ml), metallic sodium (13.1 g) and aminoguanidine hydrochloride (62.7 g) were used as reagents to give 37.1 g of a pale-yellow solid (yield 69%).

IR (KBr): 3300, 3150, 2900, 1630, 1610, 1530 cm$^{-1}$ $^1$H-NMR (DMSO-d$_6$) δ: 1.42(18H, s), 3.28(3H, s), 3.5–3.6(2H, m), 3.9–3.91(2H, m), 4.94(2H, s), 5.98(2H, s), 7.82(2H, s), 11.90(1H, s)

(4) 5-Amino-3-(3,5-di-tert-butyl-4-methoxyethoxymethoxyphenyl)-1-[methylamino(thiocarbonyl)]-1H-1,2,4-triazole The synthesis was carried out according to the method of Example 7-(3). The compound (35.0 g) obtained in (3) above, a 1N aqueous sodium hydroxide solution (93.0 ml), methyl isothiocyanate (10.2 g) and tetrahydrofuran (50 ml) were used as reagents. After the reaction, the mixture was chromatographed on silica gel (chloroform) to give 13.6 g of a pale-yellow solid (yield 33%).

IR (KBr): 3220, 2900, 1640, 1500 cm$^{-1}$ $^1$H-NMR (DMSO-d$_6$) δ: 1.44(18H, s), 3.12(3H, d), 3.28 (3H, s), 3.5–3.65(2H,m), 3.8–3.95(2H, m), 4.96(2H, s), 7.98(2H, s), 8.36(2H, brs), 9.9–10.1(1H, m) (5) 5-Amino-3-(3,5-di-tert-butyl-4-hydroxyphenyl)-1-[methylamino(thiocarbonyl)]-1H-1,2,4-triazole To the compound (7.5 g) obtained in (4) above was gradually added trifluoroacetic acid (9.0 ml), and the mixture was stirred for 30 minutes at room temperature. The powder resulted from the reaction was collected by filtration, and added to a saturated aqueous sodium hydrogencarbonate solution. The mixture was extracted with chloroform, and the extract was washed with a saturated aqueous sodium hydrogencarbonate solution and saturated brine, and dried over magnesium sulfate. After the concentration, the residue was recrystallized from chloroform to give 5.84 g of white crystals (yield 97%).

Melting point: 296°–298° C.

IR (KBr): 3250, 2900, 1650, 1510 cm$^{-1}$ $^1$H-NMR (DMSO-d$_6$) δ: 1.43(18H, s), 3.10(3H, s), 7.36 (1H, brs), 7.86(2H, s), 8.32(2H, brs), 9.90(1H, brs)

EXAMPLE 21

5-Amino-3-(2-carboxy-4,5-dichlorophenyl)-1-[methylamino(thiocarbonyl)]-1H-1,2,4-triazole (1) 2-(3-Amino-1H-1,2,4-triazol-5-yl)-4,5-dichlorobenzoic acid A solution of anhydrous 4,5-dichlorophthalic acid (25.6 g) and dry methanol (110 ml) was stirred for 1 hour at room temperature, and for 1 hour with refluxing under heating to prepare a solution of 4,5-dichlorophthalic acid monomethyl ester in methanol. Separately, a sodium methoxide solution was prepared from sodium (13.5 g) and methanol (890 ml) according to the method of Example 7-(2), and aminoguanidine hydrochloride (64.9 g) was added. The mixture was stirred for 30 minutes at room temperature, and the previously-prepared solution of phthalic acid monomethyl ester in methanol was added. The mixture was stirred for 42 hours with refluxing under heating. After the reaction, the reaction mixture was poured into ice-water, and 3N hydrochloric acid was dropwise added with stirring to make the solution neutral. The resulting solid was collected by filtration to give 31.5 g of a yellow solid. Without purification, the solid was used in the next reaction. (2) 5-Amino-3-(2-carboxy-4,5-dichlorophenyl)-1-[methylamino(thiocarbonyl)]-1H-1,2,4-triazole The synthesis was carried out according to the method of Example 7-(3). The solid (15.4 g) obtained in (1) above, 1N aqueous sodium hydroxide solution (80 ml), tetrahydrofuran (30 ml) and methyl isothiocyanate (6.26 g) were used as reagents. The mixture was stirred for 2 hours at room temperature, and the resulting white crystals were collected by filtration to give a sodium salt (4.12 g) of the objective compound. A suspension of the obtained sodium salt (3.63 g) and water (60 ml) was adjusted to pH$_3$ with 3N hydrochloric acid, and stirred for 2 hours. The resulting crystals were collected by filtration to give 2.21 g of white crystals (yield 11% from anhydrous 4,5-dichlorophthalic acid).

Melting point: >300° C.

IR (KBr): 3330, 3250, 3100, 2400, 1820, 1640, 1625, 1595, 1520 cm$^{-1}$ $^1$H-NMR (DMSO-d$_6$) δ: 3.06 (3H, d, J=4.5 Hz), 7.90 (1H, s), 8.04 (1H, s), 8.31 (2H, brs), 9.90–10.13 (1H, m)

EXAMPLE 22

5-Amino-3-(2-furyl)-1-[methylamino(thiocarbonyl)]-1H-1,2,4-triazole (1) 3-Amino-5-(2-furyl)-1H-1,2,4-triazole The synthesis was carried out according to the method of Example 7-(2). Methyl 2-furoate (15.0 g), methanol (250 ml), metallic sodium (10.9 g) and aminoguanidine hydrochloride (52.6 g) were used as reagents. After the reaction, the reaction mixture was poured into ice-water (100 ml), and adjusted to pH 3–4 with 3N hydrochloric acid. The solvent (water and methanol) was distilled away under reduced pressure. Methanol was added to the residue for extraction. The insoluble inorganic salt was removed by filtration. The filtrate was concentrated under reduced pressure and used as it was in the next reaction. (2) 5-Amino-3-(2-furyl)-1-[methylamino(thiocarbonyl)]-1H-1,2,4-triazole The synthesis was carried out according to the method of Example 7-(3). The compound obtained in (1) above, 1N aqueous sodium hydroxide solution (30.7 ml), methyl isothiocyanate (11.0 g) and tetrahydrofuran (60 ml) were used as reagents. After the reaction, the reaction mixture was neutralized with 3N hydrochloric acid. The resulting solid was collected by filtration, chromatographed on silica gel (chloroform), and recrystallized from chloroform to give 3.68 g of white crystals (yield 16% from methyl 2-furoate).

Melting point: 173°–175° C.

IR (KBr): 3300, 3050, 1650, 1620 cm$^{-1}$ $^1$H-NMR (DMSO-d$_6$) δ: 3.07(3H, s), 6.67(1H, dd, J=3.4, 1.8 Hz), 7.00(1H, d, 3.4 Hz), 7.86(1H, d, J=1.8 Hz), 8.35 (2H, brs), 9.96(1H, brs)

EXAMPLE 23

5-Amino-1-[methylamino(thiocarbonyl)]-3-(2-thienyl)-1H-1,2,4-triazole (1) Methyl 2-thiophenecarboxylate The synthesis was carried out according to the method of Example 7-(1). 2-Thiophenecarboxylic acid (25.0 g), : 1,2-dichloroethane (120 ml), methanol (23.7 ml) and concentrated sulfuric acid (0.8 ml) were used as reagents to give 24.9 g of a pale-yellow transparent liquid (yield 90%).

IR (Neat) δ: 1700, 1520 cm$^{-1}$ $^1$H-NMR (CDCl$_3$) δ: 3.89(3H, s), 7.09(1H, dd, J=5.0, 3.7 Hz), 7.55(1H, dd, J=5.0, 1.0 Hz), 7.79(1H, dd, J=3.7, 1.0 Hz)

(2) 3-Amino-5-(2-thienyl)-1H-1,2,4-triazole

The synthesis was carried out according to the method of Example 7-(2). The compound (15.0 g) obtained in (1) above, methanol (250 ml), metallic sodium (9.7 g) and aminoguanidine hydrochloride (46.7 g) were used as reagents. The mixture was stirred for 24 hours with refluxing. The reaction mixture was poured into ice water and adjusted to pH 3–4 with 3N hydrochloric acid. The solvent (water and methanol) was distilled away under reduced pressure. Methanol was added to the residue for extraction. The insoluble inorganic salt was removed by filtration. The filtrate was concentrated under reduced pressure, and used as it was in the next reaction. (3) 5-Amino-1-[methylamino(thiocarbonyl)]-3-(2-thienyl)-1H-1,2,4-triazole The synthesis was carried out according to the method of Example 7-(3). The compound obtained in (2) above, 1N sodium hydroxide (99.3 ml), methyl isothiocyanate (9.90 g) and tetrahydrofuran (50 ml) were used as reagents. After the reaction, chromatography on silica gel (chloroform), and recrystallization from chloroform gave 2.94 g of white crystals (yield 13%).

Melting point: 170°–172° C.

IR (KBr): 3300, 1650, 1520 cm$^{-1}$ $^1$H-NMR (DMSO-d$_6$) δ: 3.08(3H, s), 7.1–7.3(1H, m), 7.66(1H, d, J=3.4 Hz), 7.71(1H, d, J=5.0 Hz), 8.36(2H, brs), 9.91(1H, brs)

EXAMPLE 24

5-Amino-1-[methylamino(thiocarbonyl)]-3-(4-pyridyl)-1H-1,2,4-triazole (1) Isonicotinic acid 2-amidinohydrazide The synthesis was carried out according to the method of Example 1-(1). Isonicotinic acid hydrazide (5.17 g), methylisothiourea sulfate (10.5 g), sodium hydroxide (1.54 g)

and water (80 ml) were used as reagents. The mixture was reacted at room temperature to quantitatively give white crystals.

Melting point: 199°–201° C.

IR (KBr): 3160, 1648, 1597, 1520 cm$^{-1}$ $^1$H-NMR (DMSO-d$_6$) δ: 6.93 (2H, brs), 7.06 (2H, brs), 7.85–7.93 (2H, m), 8.48–8.51 (2H, m), 10.5 (1H, brs) (2) 3-Amino-5-(4-pyridyl)-1H-1,2,4-triazole The synthesis was carried out according to the method of Example 1-(2). The compound (6.75 g) obtained in (1) above was used as a reagent to give 4.76 g of white crystals (yield 78%).

Melting point: 280°–282° C.

IR (KIr) δ: 3360, 3100, 2920, 2770, 1667, 1610 cm$^{-1}$ $^1$H-NMR (DMSO-d$_6$) δ: 6.18 (2H, brs), 7.79 (2H, d, J=5.8 Hz), 8.60 (2H, d, J=5.8 Hz), 12.36 (1H, brs) (3) 5-Amino-1-[methylamino(thiocarbonyl)]-3-(4-pyridyl)-1H-1,2,4-triazole The synthesis was carried out according to the method of Example 1-(3). The compound (1.50 g) obtained in (2) above, methyl isothiocyanate (1.19 g) and dimethyl sulfoxide (15 ml) were used as reagents. After the reaction, chromatography on silica gel (chloroform-methanol) gave 550 mg of a white solid (yield 25%). The solid was recrystallized from methanol to give white crystals.

Melting point: 187.5°–188.5° C.

IR (KBr): 3300, 3030, 1636, 1611, 1518 cm$^{-1}$ $^1$H-NMR (DMSO-d$_6$) δ: 3.11 (3H, d, J=4.6 Hz), 7.92–7.94(2H, m), 8.39 (2H, brs), 8.72–8.74(2H, m), 10.10–10.18 (1H, m)

EXAMPLE 25

5-Amino-3-(6-chloro-3-pyridyl)-1-[methylamino (thiocarbonyl)]-1H-1,2,4-triazole (1) 6-Chloronicotinic acid 2-amidinohydrazide To a solution of 6-chloronicotinic acid (10.0 g) in dichloromethane (100 ml) was added dropwise dimethylformamide (10 ml) and thionyl chloride (5.1 ml), and the mixture was stirred for 1 hour with refluxing. The resulting reaction mixture was dropwise added to aminoguanidine hydrochloride (24.6 g) in a 2.2N aqueous sodium hydroxide solution (100 ml) under ice-cooling. After the dropwise addition, the mixture was stirred at said temperature for 10 minutes to give 6.87 g of a pale-brown solid by filtration (yield 51%).

IR(KBr): 3150, 1650, 1580 cm$^{-1}$ $^1$H-NMR (DMSO-d$_6$) δ: 6.65(2H, brs), 7.01(2H, brs), 7.40(1H, d, J=8.0 Hz), 8.28(1H, dd, J=8.0, 2.0 Hz), 8.89(1H, d, J=2.0 Hz)

(2) 5-Amino-3-(6-chloro-3-pyridyl)-1-[methylamino (thiocarbonyl)]-1H-1,2,4-triazole The synthesis method of Example 1-(2) was applied. The compound (5.4 g) obtained in (1) above and dimethylsulfoxide (50 ml) were used as reagents and the mixture was stirred at 180° C. for 1 hour. After the reaction, the reaction mixture was ice-cooled and used as it was in the next reaction. The conversion to a thiourea compound was performed according to the method of Example 7-(3). The above-mentioned solution, a 1N aqueous sodium hydroxide solution (20 ml) and methyl isothiocyanate (1.5 g) were used as reagents. After the reaction, the mixture was neutralized with 3N hydrochloric acid and the resulting powder was collected by filtration. The powder was subjected to silica gel column chromatography (chloroform) and recrystallization (chloroform) to give 2.9 g of white crystals (yield 29%).

Melting point: 208°–211° C.

IR(KBr): 3300, 3050, 1640, 1520 cm$^{-1}$ $^1$H-NMR (DMSO-d$_6$) δ: 3.09(3H, s), 7.69(1H, d, J=8.0 Hz), 8.37(1H, dd, J=8.0,2.0 Hz), 8.42(2H, brs), 8.99(1H, d, J=2.0 Hz), 10.13(1H, brs)

EXAMPLE 26

5-Amino-3-(5-chloro-2-pyridyl)-1-[methylamino (thiocarbonyl)]-1H-1,2,4-triazole (1) 2-Bromo-5-chloropyridine To a solution of 2-amino-5-chloropyridine (15.0 g) in 47% hydrobromic acid (18 ml) was gradually added dropwise bromine (18 ml) under ice-cooling. After the dropwise addition, a solution of sodium nitrite (20.1 g) in water (100 ml) was gradually added dropwise under ice-cooling, and the mixture was stirred for 1 hour. The solution was adjusted to pH 8 with a 5N aqueous sodium hydroxide solution and extracted with ether, washed with an aqueous sodium nitrite solution and water, and dried over magnesium sulfate. The solvent was distilled away under reduced pressure to give 19.5 g of a pale-brown solid (yield 87%).

IR (KBr): 3000, 1550 cm$^{-1}$ $^1$H-NMR (CDCl$_3$) δ: 7.43(1H, d, J=8.0 Hz), 7.54(1H, dd, J=8.0, 3.0 Hz), 8.35(1H, d, J=3.0 Hz)

(2) 5-Chloro-2-cyanopyridine

The compound (10.0g) obtained in (1) above, dimethylformamide (50 ml), copper cyanide (6.98 g), triethylamine (10.9 ml) and molecular sieves 4A (2 g, heat-treated) were placed in an autoclave. The outer temperature was set for 200° C. and the mixture was stirred for 4 hours. Water and ethyl acetate were added to the reaction mixture, and, after filtering off insoluble matters, extracted with ethyl acetate. The organic layer was washed with water and dried over magnesium sulfate. The solvent was distilled away under reduced pressure and the residue was subjected to silica gel column chromatography (hexane-ethyl acetate) to give 1.92 g of a white solid (yield 27%).

IR (KBr): 3050, 2220, 1550 cm$^{-1}$ $^1$H-NMR (CDCl$_3$) δ: 7.66(1H, d, J=8.6 Hz), 7.84(1H, dd, J=8.6, 2.0 Hz), 8.68(1H, d, J=2.0 Hz) (3) Ethyl 5-chloro-2-pyridinecarboxylate To a solution of the compound (3.16 g) obtained in (2) above in ethanol (5 ml) was added a 2.7N hydrochloric acid-ethanol solution (10 ml) and the mixture was stirred with refluxing for 2 hours. Ethanol was distilled away under reduced pressure, and the mixture was neutralized with a saturated aqueous sodium hydrogencarbonate solution and extracted with ethyl acetate. The extract was dried over magnesium sulfate and the solvent was distilled away under reduced pressure to give 4.10 g of a pale-brown solid (yield 97%).

IR (KBr): 3400, 3050, 2980, 1710, 1570, 1555 cm$^{-1}$ $^1$H-NMR (CDCl$_3$)d: 1.45(3H, t, J=7.0 Hz), 4.48(2H, q, J=7.0 Hz), 7.82(1H, dd, J=8.0, 1.4 Hz), 8.09(1H, d, J=8.0 Hz), 8.70(1H, d, J=1.4 Hz) (4) 3-Amino-5-(5-chloro-2-pyridyl)-1H-1,2,4-triazole The synthesis method of Example 7-(2) was applied. The compound (3.94 g) obtained in (3) above, a 5M sodium methoxide-methanol solution (17 ml), methanol (20 ml) and aminoguanidine hydrochloride (9.39 g) were used as reagents. The mixture was stirred with refluxing for 18 hours and methanol was distilled away under reduced pressure. Water was added to the residue and the aqueous layer was adjusted to pH 3–4 with 3N hydrochloric acid to give 3.40 g of a pale-yellow solid that precipitated (yield 82%).

IR (KBr): 3350, 3100, 1640, 1580 cm$^{-1}$ $^1$H-NMR (DMSO-d$_6$) δ: 5.93(2H, brs), 7.88(1H, d, J=7.5 Hz), 7.96(1H, dd, J=7.5, 2.0 Hz), 8.61(1H, d, J=2.0 Hz) (5) 5-Amino-3-(5-chloro-3-pyridyl)-1-[methylamino (thiocarbonyl)]-1H-1,2,4-triazole The synthesis method of Example 7-(3) was applied. The compound (3.39 g) obtained in (4) above, a 1N aqueous sodium hydroxide solution (26 ml), methyl isothiocyanate (1.9 g) and tetrahydrofuran (30 ml) were used as reagents. The mixture was stirred at room temperature for 5 hours and neutralized with 3N hydrochloric acid. The resulting powder was collected by filtration and subjected to silica gel column chromatography (chloroform-methanol) and recrystallization from chloroform-methanol to give 917 mg of white crystals (yield 20%).

Melting point: 215°–225° C. (decomposition)
IR (KBr): 3300, 3050, 1635, 1520 cm$^{-1}$
$^1$H-NMR (DMSO-d$_6$) δ: 3.09(3H, s), 8.09(1H, s), 8.09 (1H, s), 8.34(2H, brs), 8.72(1H, s), 10.11(1H, brs)

EXAMPLE 27

5-Amino-1-[methylamino(thiocarbonyl)]-3-(1-naphthyl)-1H-1,2,4-triazole (1) Methyl 1-naphthoate The synthesis method of Example 7-(1) was applied. 1—Naphthoic acid (4.97 g), methanol (10 ml), 1,2-dichloroethane (12 ml) and concentrated sulfuric acid (0.6 ml) were used as reagents and the mixture was stirred at 60° C. for 17 hours. After the reaction, the mixture was extracted with ether to give 4.35 g of a pale-yellow transparent liquid (yield 87%).

IR (KBr): 3600, 3050, 2930, 1710, 1595, 1575, 1510 cm$^{-1}$
$^1$H-NMR (DMSO-d$_6$) δ: 3.95 (3H, s), 7.56–7.76 (3H, m), 8.02–8.28 (3H, m), 8.76 (1H, d, J=90 Hz)

(2) 1—Naphthoic acid hydrazide

The synthesis method of Example 2-(1) was applied. The compound (43.1 g) obtained in (1) above, hydrazine monohydrate (200 ml) and ethanol (80 ml) were used as reagents. After the reaction, a white solid was quantitatively obtained.

IR (KBr): 3400, 3280, 1640, 1600, 1585, 1520 cm$^{-1}$
$^1$H-NMR (DMSO-d$_6$) δ: 4.60 (2H, brs), 7.49–7.63 (4H, m), 7.93–8.08 (2H, m), 8.15–8.25 (1H, m), 9.69 (1H, brs)

(3) 1—Naphthoic acid 2-amidinohydrazide

The synthesis method of Example 1-(1) was applied. The compound (18.3 g) obtained in (2) above, methylisothiourea sulfate (81.6 g), sodium hydroxide (11.7 g), water (90 ml) and methanol (180 ml) were used as reagents and the mixture was reacted at 60° C. for 48 hours to give 39.7 g of a yellow solid. A portion (21.2 g) from the obtained solid was used in the next reaction.

$^1$H-NMR (DMSO-d$_6$) δ: 5.46 (2H, brs), 6.71 (1H, brs), 7.47 (1H, brs), 7.5–8.4 (7H, m), 9.0–10.1 (1H, brs) (4) 3-Amino-5-(1-naphthyl)-1H-1,2,4-triazol The synthesis method of Example 1-(2) was applied. The compound (21.2 g) obtained in (3) above was used as a reagent to give 13.6 g of a yellow solid. The obtained compound was used as it was in the next reaction.

$^1$H-NMR (DMSO-d$_6$) δ: 6.99 (2H, brs), 7.4–8.3 (6H, m), 9.05–9.33 (1H, m), 12.2 (1H, m) (5) 5-Amino-1-[methylamino(thiocarbonyl)]-3-(1-naphthyl)-1H-1,2,4-triazole The synthesis method of Example 1-(3) was applied. The compound (13.6 g) obtained in (4) above, methyl isothiocyanate (25 g) and dimethyl sulfoxide (60 ml) were used as reagents. After the reaction, silica gel column chromatography (hexane-ethyl acetate) and recrystallization from ethyl acetate gave 844 mg of white crystals (yield 8.9% from 1-naphthoic acid hydrazide).

Melting point: 182°–183° C.
IR (KBr): 3350, 3300, 3010, 1640, 1580, 1520 cm$^{-1}$
$^1$H-NMR (DMSO-d$_6$) δ: 3.14 (3H, d, J=4.7 Hz), 7.52–7.67 (3H, m), 8.00 (1H, d, J=7.6 Hz), 8.06 (1H, d, J=8.2 Hz), 8.22 (1H, d, J=7.2 Hz), 8.37 (2H, brs), 9.13 (1H, d, J=8.4 Hz), 10.0–10.15 (1H, m)

EXAMPLE 28

5-Amino-3-(4-chloro-1-naphthyl)-1-[methylamino(thiocarbonyl)]-1H-1,2,4-triazole (1) 1-Acetyl-4-chloronaphthalene To aluminum chloride (54.5 g) and dichloromethane (250 ml) was dropwise added 1-chloronaphthalene (47 ml) under ice-cooling over 10 minutes. The obtained reaction mixture was stirred for 20 minutes and acetyl chloride (25 ml) was dropwise added over 40 minutes. The reaction mixture was stirred at room temperature for 4 hours and with refluxing for 20 minutes. The reaction mixture was cooled to room temperature, poured into 1N hydrochloric acid (300 ml), extracted with dichloromethane, washed with saturated brine and dried over magnesium sulfate. The solvent was distilled away and the residue was subjected to silica gel column chromatography (hexane-ethyl acetate) to give 37.3 g of a red-brown liquid (yield 55%).

IR (Neat) δ: 3080, 3000, 1675, 1560, 1505 cm$^{-1}$
$^1$H-NMR (DMSO-d$_6$) δ: 2.74(3H, s), 7.73–7.79(2H, m), 7.81(1H, d, J=7.8 Hz), 8.10(1H, d, J=7.8 Hz), 8.27–8.32(1H, m), 8.64–8.70(1H, m)

(2) 4-Chloro-1-naphthoic acid

The compound (8.33 g) obtained in (1) above and a 5% sodium hypochlorite solution (380 ml) were stirred with refluxing for 44 hours. The reaction mixture was cooled to room temperature and concentrated hydrochloric acid (10 ml) was dropwise added. The resulting solid was collected by filtration. The obtained solid was subjected to silica gel column chromatography (hexane-ethyl acetate) to give 1.96 g of a red-brown solid (yield 23%).

IR (KBr): 3400, 3000, 2600, 1680, 1565, 1505 cm$^{-1}$
$^1$H-NMR (DMSO-d$_6$) δ: 7.72–7.87(3H, m), 8.11(1H, d, J=7.9 Hz), 8.27–8.37(1H, m), 8.90–9.0(1H, m)

(3) Methyl 4-chloro-1-naphthoate

The synthesis method of Example 7-(1) was applied. The compound (1.93g) obtained in (2) above, 1,2-dichloroethane (50 ml), methanol (25 ml) and concentrated sulfuric acid (1.8 ml) were used as reagents to give 1.99 g of a red-brown solid (yield 96%).

IR (KBr): 3350, 1710, 1560, 1500 cm$^{-1}$
$^1$H-NMR (DMSO-d$_6$) δ: 3.96(3H, s), 7.74–7.88(3H, m), 8.11(1H, d, J=7.9 Hz), 8.28–8.39(1H, m), 8.77–8.90(1H, m)

(4) 3-Amino-5-(4-chloro-1-naphthyl)-1H-1,2,4-triazol

The synthesis method of Example 7-(2) was applied. The compound (1.90 g) obtained in (3) above, methanol (20 ml), metallic sodium (810 mg) and aminoguanidine nitrate (4.8 g) were used as reagents to give a brown solid (2.27 g). The obtained compound was used as it was in the next reaction.

(5) 5-Amino-3-(4-chloro-1-naphthyl)-1-[methylamino(thiocarbonyl)]-1H-1,2,4-triazole The synthesis method of Example 7-(3) was applied. The compound (2.19 g) obtained in (4) above, a 1N sodium hydroxide solution (10.0 ml), methyl isothiocyanate (1.38 g) and tetrahydrofuran (10 ml) were used as reagents. After the reaction, silica gel column chromatography (chloroform) and recrystallization from chloroform gave 135 mg of white crystals (yield 5% from methyl 4-chloro-1-naphthoate).

Melting point: 270°–272° C.
IR (KBr): 3300, 3080, 1660, 1570, 1515 cm$^{-1}$
$^1$H-NMR (DMSO-d$_6$) δ: 3.13(3H, s), 7.62–7.90(3H, m), 8.20(1H, d, J=7.9 Hz), 8.25–8.50(3H, m), 9.2–9.3(1H, m), 10.2(1H, brs)

EXAMPLE 29

5-Amino-1-[methylamino(thiocarbonyl)]-1H-1,2,4-triazole

The synthesis method of Example 1-(3) was applied. 3-Amino-1H-1,2,4-triazole (3.91 g), dimethylformamide (20 ml) and methyl isothiocyanate (3.41 g) were used as reagents. After the reaction, the resulting substance was removed by filtration and the filtrate was extracted with ethyl acetate, after which the obtained white solid was recrystallized from ethanol and ethyl acetate to give 1.34 g of yellow crystals (yield 18%).

Melting point: 184°–185° C.

IR (KBr): 3420, 3310, 1634, 1520 cm$^{-1}$ $^1$H-NMR (DMSO-d$_6$) δ: 3.04 (3H, s), 7.63 (1H, s), 8.18 (2H, brs), 10.02 (1H, brs)

EXAMPLE 30

5-Amino-3-methyl-1-[methylamino(thiocarbonyl)]-1H-1,2,4-triazole (1) Ethyl N-cyanoacetoimidate A solution of cyanamide (3.52 g), acetic anhydride (15.7 ml) and triethyl orthoacetate (15.0 ml) was stirred at 140° C. for 2.5 hours. After the reaction, the mixture was distilled under reduced pressure to give 5.29 g of a colorless transparent liquid (yield 58%). Boiling point: 50°–60° C./2.5 mmHg IR (KBr): 2990, 2940, 2210, 1700, 1668, 1604 cm$^{-1}$ $^1$H-NMR (CDCl$_3$) δ: 1.35 (3H, t, J=7.1 Hz), 2.40 (3H, s), 4.29 (2H, q, J=7.1 Hz)

(2) 3-Amino-5-methyl-1H-1,2,4-triazole

A solution of the compound (5.26 g) obtained in (1) above in acetonitrile (10 ml) was cooled to 0° C. and hydrazine (1.6 ml) was dropwise added. The mixture was stirred at room temperature for 16 hours and the resulting crystals were collected by filtration to give 677 mg of white crystals (yield 15%).

Melting point: 147°–148° C.

IR (KBr): 3380, 3300, 3180, 3030, 2800, 2710, 1632, 1596, 1542 cm$^{-1}$ $^1$H-NMR (DMSO-d$_6$) δ: 2.06 (3H, s), 5.47 (2H, brs), 11.75(1H, brs)

(3) 5-Amino-3-methyl-1-[methylamino(thiocarbonyl)]-1H-1,2,4-triazole

The synthesis method of Example 1-(3) was applied. The compound (664 mg) obtained in (2) above, dimethylformamide (13 ml) and methyl isothiocyanate (600 mg) were used as reagents to give 340 mg of white crystals (yield 29%).

Melting point: 180°–181° C.

IR (KBr): 3330, 3050, 1645, 1530 cm$^{-1}$ $^1$H-NMR (DMSO-d$_6$) δ: 2.13 (3H, s), 3.01(3H, s), 8.11 (2H, brs), 9.86 (1H, brs)

EXAMPLE 31

3,5-Diamino-1-[methylamino(thiocarbonyl)]-1H-1,2,4-triazole

The synthesis method of Example 1-(3) was applied. 3,5-Diamino-1H-1,2,4-triazole (11.0 g), dimethylformamide (100 ml) and methyl isothiocyanate (10.0 g) were used as reagents. After the reaction, recrystallization from ethyl acetate gave 13.0 g of white powdery crystals (yield 68%).

Melting point: 176°–178° C.

IR (KBr): 3430, 3280, 1620, 1520 cm$^{-1}$ $^1$H-NMR (DMSO-d$_6$) δ: 2.98 (3H, d, J=4.4 Hz), 5.63 (2H, brs), 8.14 (2H, brs),9.19 (1H, m)

EXAMPLE 32

3-Acetylamino-5-amino-1-[methylamino(thiocarbonyl)]-1H-1,2,4-triazole

To the compound (3.00 g) obtained in Example 31 and pyridine (25 ml) was gradually added dropwise acetic anhydride (2.1 ml) under ice-cooling. The mixture was stirred at 0° C.-room temperature for 66 hours and the resulting crystals were collected by filtration. The crystals were washed with hexane-ethyl acetate and dried to give 2.98 g of white powdery crystals (yield 80%).

Melting point: >300° C.

IR (KBr): 3370, 3320, 3230, 2810, 1676, 1638, 1582, 1520 cm$^{-1}$ $^1$H-NMR (DMSO-d$_6$)δ: 2.10 (3H, brs), 3.04 (3H, s), 8.30 (2H, brs), 9.46 (1H, brs), 10.27 (1H, brs)

EXAMPLE 33

5-Amino-3-[(dimethylaminomethylidene)amino]-1-[methylamino(thiocarbonyl)]-1H-1,2,4-triazole A solution of the compound (1.00 g) obtained in Example 31, dimethylformamide (25 ml) and triethylamine (1.0 ml, 7.2 mmol) was cooled to 0° C. and benzoyl chloride (0.70 ml) was gradually added dropwise thereto. The mixture was stirred at 0° C.-room temperature for 4.5 hours and the reaction mixture was poured into water and extracted with ethyl acetate. The extract was washed with saturated brine and dried over anhydrous magnesium sulfate. The solvent was distilled away under reduced pressure. After the concentration, silica gel column chromatography (chloroform-methanol) and recrystallization from chloroform-methanol gave 350 mg of pale-yellow crystals (yield 27%).

Melting point: 184°–188° C.

IR (KBr): 3360, 3060, 2930, 1628, 1510

$^1$H-NMR (DMSO-d$_6$) δ: 2.93 (3H, s), 2.98 (3H, d, J=4.5 Hz), 3.05 (3H, s), 8.10 (2H, brs), 8.30 (1H, s), 9.74 (1H, m)

EXAMPLE 34

5-Amino-3-[(ethoxymethylidene)amino]-1-[methylamino(thiocarbonyl)]-1H-1,2,4-triazole A solution of the compound (500 mg) obtained in Example 31 and diethoxymethyl acetate (7 ml) was stirred at room temperature. After stirring for 1 hour, the resulting crystals were collected by filtration to give 480 mg of a white powdery solid (yield 73%).

IR (KBr): 3350, 1642, 1620, 1523 cm$^{-1}$ $^1$H-NMR (DMSO-d$_6$) δ: 1.30 (3H, t, J=7.1 Hz), 3.01 (3H, s), 4.28 (2H, q, J=7.1 Hz), 8.28 (2H, brs), 8.52 (1H, s), 9.93 (1H, brs)

EXAMPLE 35

5-Amino-3-ethoxalylamino-1-[methylamino(thiocarbonyl)]-1H-1,2,4-triazole

The compound (4.00 g) obtained in Example 31, dimethylformamide (80 ml) and triethylamine (3.9 ml) were cooled to 0° C. Ethyloxalyl chloride (2.7 ml) was gradually added dropwise and the mixture was stirred at 0° C.-room temperature for 2.5 hours. After the stirring, chloroform (50 ml) was added and the mixture was stirred at 0° C. for 30 minutes. The reaction mixture was poured into water and extracted with chloroform. The extract was washed with saturated brine and dried over anhydrous magnesium sulfate. The solvent was distilled away under reduced pressure to give a pale-yellow liquid. This liquid was subjected to silica gel column chromatography (chloroform-methanol) and recrystallization from ethanol to give 1.22 g of white powdery crystals (yield 19%).

Melting point: 164°–165° C.

IR (KBr): 3380, 3260, 1722, 1643, 1553 cm$^{-1}$ $^1$H-NMR (DMSO-d$_6$) δ: 1.28 (3H, t, J=70 Hz), 3.04 (3H, d, J=3.7 Hz), 4.28 (2H, q, J=70 Hz), 8.38 (2H, brs), 9.59 (1H, brs), 11.1 (1H, brs)

EXAMPLE 36

5-Amino-3-benzoylamino-1-[methylamino(thiocarbonyl)]-1H-1,2,4-triazole

The synthesis method of Example 32 was applied. The compound (3.00 g) obtained in Example 31, pyridine (8 ml) and anhydrous benzoic acid (2.839 g) were used as reagents and the mixture was stirred at room temperature for 6 days. After the reaction, the reaction mixture was poured into a saturated aqueous sodium hydrogencarbonate solution and extracted with ethyl acetate. The extract was washed with water and saturated brine and dried over anhydrous magnesium sulfate. The solvent was distilled away under reduced pressure to give a yellow solid. The solid was subjected to silica gel column chromatography (chloroform-methanol) to give 916 mg of a mixture with pyridine (yield 36%: objective compound: pyridine=1:1.5). A recrystallization from chloroform gave white powdery crystals.

Melting point: >300° C.

IR (KBr): 3420, 3270, 3120, 1698, 1631, 1590, 1538, 1508 cm$^{-1}$ $^1$H-NMR (DMSO-d$_6$) δ: 3.06 (3H, s), 7.51 (2H, t, J=7.4 Hz), 7.60 (1H, t, J=7.4 Hz), 7.95 (2H, d, J=7.4 Hz), 8.33 (2H, brs), 9.64 (1H, brs), 10.74 (1H, brs)

EXAMPLE 37

5-Amino-3-[(N-benzylidene)amino]-1-[methylamino(thiocarbonyl)]-1H-1,2,4-triazole The compound (3.00 g) obtained in Example 31, ethanol (100 ml), benzaldehyde (1.99 g) and DL-camphor-10-sulfonic acid (110 mg) were stirred with heating in an oil bath at 60° C. for 5 hours. After the reaction, the mixture was cooled to room temperature and the resulting crystals were collected by filtration, which were washed with ethanol and dried to give 2.13 g of pale-yellow crystals (yield 47%).

Melting point: 183°–185° C.

IR (KBr): 3320, 3180, 1635, 1502 cm$^{-1}$ $^1$H-NMR (DMSO-d$_6$) δ: 3.05 (3H, s), 7.56 (2H, t, J=7.2 Hz), 7.62 (1H, t, J=7.2 Hz), 7.99 (2H, d, J=7.2 Hz), 8.36 (2H, brs), 9.16 (1H, s), 10.12 (1H, brs)

EXAMPLE 38

5-Amino-3-anilino-1-[methylamino(thiocarbonyl)]-1H-1,2,4-triazole (1) N-phenyl-N'-cyano-O-phenylisourea Aniline (7.82 g), 2-propanol (160 ml) and diphenylcyanocarbonimidate (20.0 g) were stirred at room temperature for 2 hours. After the reaction, the resulting crystals were collected by filtration, washed with 2-propanol and dried to give 17.6 g of white crystals (yield 91%).

Melting point: 190°–191° C.

IR (KBr): 3420, 3140, 2190, 1634, 1597, 1583 cm$^{-1}$ $^1$H-NMR (DMSO-d$_6$) δ: 7.22–7.33 (4H, m), 7.37–7.52 (6H, m), 10.83 (1H, brs)

(2) 3-Amino-5-anilino-1H-1,2,4-triazole

The compound (10.0 g) obtained in (1) above, methanol (160 ml) and hydrazine monohydrate (2.1 ml) were stirred at room temperature for 2 hours. After the reaction, the solvent was distilled away and the precipitated crystals were collected by filtration. The obtained crystals were washed with 2-propanol and dried to give 4.86 g of pale-brown crystals (yield 66%).

Melting point: 158°–159° C.

IR (KBr): 3340, 3210, 1654, 1603, 1568, 1541 cm$^{-1}$ $^1$H-NMR (DMSO-d$_6$) δ: 5.81 (2H, brs), 6.71 (1H, t, J=7.8 Hz), 7.15 (2H, t, J=7.8 Hz), 7.48 (2H, d, J=7.8 Hz), 8.54 (1H, brs), 11.10 (1H, brs)

(3) 5-Amino-3-anilino-1-[methylamino(thiocarbonyl)]-1H-1,2,4-triazole

The synthesis method of Example 1-(3) was applied. The compound (3.86 g) obtained in (2) above, dimethylformamide (50 ml) and methyl isothiocyanate (1.81 g) were used as reagents and the mixture was stirred at room temperature for 6 days. After the reaction, silica gel column chromatography (chloroform-methanol) and recrystallization from chloroform gave 961 mg of white crystals (yield 18%).

Melting point: 196°–198° C.

IR (KBr): 3400, 3300, 1628, 1518 cm$^{-1}$ $^1$H-NMR (DMSO-d$_6$) δ: 3.09 (3H, s), 6.87 (1H, t, J=7.6 Hz), 7.25 (2H, t, J=7.6 Hz), 7.65 (2H, d, J=7.6 Hz), 8.30 (2H, brs), 9.21 (1H, brs), 9.43 (1H, brs)

EXAMPLE 39

5-Amino-1-[methylamino(thiocarbonyl)]-3-phenoxy-1H-1,2,4-triazole (1) 3-Amino-5-phenoxy-1H-1,2,4-triazole Diphenylcyanocarbonimidate (9.53 g) and methanol (150 ml) were cooled to 0° C. and hydrazine (1.5 ml) was gradually added dropwise thereto. The mixture was stirred at 0° C.-room temperature for 2 hours. Methanol was distilled away under reduced pressure and the residue was subjected to silica gel column chromatography (chloroform-methanol) to quantitatively give white crystals.

Melting point: 129°–132° C.

IR (KBr): 3420, 3100, 1643, 1590, 1542 cm$^{-1}$ $^1$H-NMR (DMSO-d$_6$) δ: 6.07 (2H, brs), 7.06–7.14 (3H, m), 7.34 (2H, t, J=7.7 Hz), 11.48 (1H, brs) (2) 5-Amino-1-[methylamino(thiocarbonyl)]-3-phenoxy-1H-1,2,4-triazole The synthesis method of Example 7-(3) was applied. The compound (5.52 g) obtained in (1) above, 0.7N sodium hydroxide (50 ml), methyl isothiocyanate (3.04 g) and tetrahydrofuran (50 ml) were used as reagents. After the reaction, silica gel column chromatography (chloroform-methanol) and recrystallization from chloroform-hexane gave 1.1 g of white crystals (yield 14%).

Melting point: 184°–186° C.

IR (KBr): 3280, 3120, 3060, 1662, 1570, 1517 cm$^{-1}$ $^1$H-NMR (DMSO-d$_6$) δ: 3.00 (3H, s), 7.21 (1H, t, J=7.7 Hz), 7.27 (2H, d, J=7.7 Hz), 7.41 (2H, t, J=7.7 Hz), 8.48 (2H, brs), 9.67 (1H, brs)

EXAMPLE 40

5-Amino-3-(4-cyanophenylthio)-1-[methylamino(thiocarbonyl)]-1H-1,2,4-triazole (1) 3-Amino-5-(4-cyanophenylthio)-1H-1,2,4-triazole To 60% sodium hydride-in-oil (3.89 g) in dimethylformamide (50 ml) was dropwise added a solution (100 ml) of 3-amino-5-mercapto-1H-1,2,4-triazole (10.0 g) in dimethylformamide under ice-cooling. After the dropwise addition, the mixture was stirred at 0° C.-room temperature for 30 minutes and ice-cooled again. A solution (50 ml) of 4-chlorobenzonitrile (13.0 g) in dimethylformamide was dropwise added. The mixture was stirred at 0° C.-room temperature for 30 minutes and at 100°–110° C. for 33 hours. After the reaction, the mixture was cooled to room temperature and added with water, followed by stirring for 30 minutes. The reaction mixture was poured into water and extracted with ethyl acetate. The extract was washed with water and saturated brine, and dried over anhydrous magnesium sulfate. The solvent was distilled away under reduced pressure. The crude product was subjected to silica gel column chromatography (chloroform-methanol) to give 1.86 g of white crystals (yield 9.9%).

Melting point: 181°–183° C.

IR (KBr): 3380, 3300, 3180, 2220, 1640, 1574 cm$^{-1}$ $^1$H-NMR (DMSO-d$_6$) δ: 6.26 (2H, brs), 7.45 (2H, d, J=8.4 Hz), 7.75 (2H, d, J=8.4 Hz), 12.49 (1H, brs) (2) 5-Amino-3-(4-cyanophenylthio)-1-[methylamino(thiocarbonyl)]-1H-1,2,4-triazole The synthesis method of Example 1-(3) was applied. The compound (2.10 g) obtained in (1) above, dimethylformamide (30 ml) and methyl isothiocyanate (3.21 g) were used as reagents. The mixture was reacted at 50°–60° C. for 42 hours, extracted with ethyl acetate and subjected to silica gel column chromatography (chloroform-methanol) and recrystallization from chloroform to give 387 mg of white crystals (yield 14%).

Melting point: 200°–203° C.

IR (KBr): 3430, 3340, 3300, 3070, 2220, 1637, 1532 cm$^{-1}$ $^1$H-NMR (DMSO-d$_6$) δ: 3.03 (3H, d, J=4.5 Hz), 7.69 (2H, d, J=8.6 Hz), 7.83 (2H, d, J=8.6 Hz), 8.43 (2H, brs), 10.00 (1H, m)

EXAMPLE 41

5-Amino-3-benzyl-1-[methylamino(thiocarbonyl)]-1H-1,2,4-triazole (1) 3-Amino-5-benzyl-1H-1,2,4-triazole The synthesis method of Example 7-(2) was applied. Methyl phenylacetate (10.0 g), methanol (160 ml), metallic sodium (5.73 g) and aminoguanidine hydrochloride (27.5 g) were used as reagents. After the reaction, the reaction mixture was poured into ice water and adjusted to pH 8 with 2N hydrochloric acid and sodium hydrogencarbonate. Methanol was distilled away under reduced pressure and the residue was extracted with ethyl acetate. The extract was dried over anhydrous magnesium sulfate and the solvent was distilled away under reduced pressure to give a white solid. The solid was washed with ethyl acetate to give 7.12 g of white crystals (yield 61%).

Melting point: 166°–169° C.

IR (KBr): 3410, 3290, 1627, 1580, 1540 cm$^{-1}$ $^1$H-NMR (DMSO-d$_6$) δ: 3.73 (2H, brs), 5.76 (2H, brs), 7.15–7.20 (1H, m), 7.23–7.28 (4H, m), 11.61 (1H, brs)

(2) 5-Amino-3-benzyl-1-[methylamino(thiocarbonyl)]-1H-1,2,4-triazole

The synthesis method of Example 7-(3) was applied. The compound (6.17 g) obtained in (1) above, a 0.77N aqueous sodium hydroxide solution (40 ml), methyl isothiocyanate (2.86 g) and tetrahydrofuran (40 ml) were used as reagents and the mixture was stirred at room temperature for 17 hours. 2N Hydrochloric acid (19 ml) was added to neutralize the mixture. The resulting crystals were collected by filtration and washed with hexane-ethyl acetate to give 3.55 g of white powdery crystals (yield 40%).

Melting point: 173°–175° C.

IR (KBr): 3300, 3050, 1634, 1504 cm$^{-1}$ $^1$H-NMR (DMSO-d$_6$) δ: 3.03 (3H, s), 3.81 (2H, s), 7.19–7.24 (1H, m), 7.27–7.32 (4H, m), 8.14 (2H, brs), 9.88 (1H, brs)

EXAMPLE 42

5-Amino-3-(4-chlorostyryl)-1-[methylamino(thiocarbonyl)]-1H-1,2,4-triazole (1) Methyl 4-chlorocinnamate The synthesis method of Example 7-(1) was applied. 4-Chlorocinnamic acid (10.0 g), 1,2-dichloroethane (50 methanol (9.0 ml) and concentrated sulfuric acid (0.4 ml) were used as reagents to give 10.2 g of a white solid (yield 95%).

IR (KBr): 1696, 1628 cm$^{-1}$ $^1$H-NMR (DMSO-d$_6$) δ: 3.73 (3H, s), 6.67 (1H, d, J=16.1 Hz), 7.48 (2H, d, J=8.5 Hz), 7.66 (1H, d, J=16.1 Hz), 7.76 (2H, d, J=8.5 Hz)

(2) 3-Amino-5-(4-chlorostyryl)-1H-1,2,4-triazole

The synthesis method of Example 7-(2) was applied. The compound (9.66 g) obtained in (1) above, methanol (140 ml), metallic sodium (5.69 g) and aminoguanidine hydrochloride (27.3 g) were used as reagents to give 4.93 g of a pale-brown solid (yield 46%).

IR (KBr): 3070, 2850, 2760, 1678 cm$^{-1}$ $^1$H-NMR (DMSO-d$_6$) δ: 7.06 (1H, d, J=16.6 Hz), 7.49 (2H, d, J=8.5 Hz), 7.57 (1H, d, J=16.6 Hz), 7.66 (2H, d, J=8.5 Hz), 7.98 (2H, brs)

(3) 5-Amino-3-(4-chlorostyryl)-1-[methylamino(thiocarbonyl)]-1H-1,2,4-triazole

The synthesis method of Example 7-(3) was applied. The compound (4.00 g) obtained in (2) above, 0.67N sodium hydroxide (30 ml), methyl isothiocyanate (1.52 g) and tetrahydrofuran (30 ml) were used as reagents and the mixture was reacted at room temperature for 4 hours. After the reaction, the mixture was neutralized with 2N hydrochloric acid. The resulting substance was collected by filtration and washed with water and hexane-ethyl acetate to give 3.67 g of white crystals (yield 69%).

Melting point: 209°–210° C.

IR (KBr): 3330, 3270, 3010, 1655, 1520 cm$^{-1}$ $^1$H-NMR (DMSO-d$_6$) δ: 3.06 (3H, s), 6.93 (1H, d, J=16.1 Hz), 7.46 (2H, d, J=8.5 Hz), 7.49 (1H, d, J=16.1 Hz), 7.68 (2H, d, J=8.5 Hz), 8.25 (2H, brs), 9.93 (1H, brs)

EXAMPLE 43

5-Amino-1-[methylamino(thiocarbonyl)]-3-(2-phenylethynyl)-1H-1,2,4-triazole (1) Methyl phenylpropiolate The synthesis method of Example 7-(1) was applied. Phenylpropiolic acid (5.16 g), : 1,2-dichloroethane (40 ml), methanol (5 ml) and concentrated sulfuric acid (0.2 ml) were used as reagents to quantitatively give a colorless transparent liquid.

IR (Neat) δ: 3000, 2970, 2230, 1708 cm$^{-1}$1

$^1$H-NMR (CDCl$_3$) δ: 3.84 (3H, s), 7.37 (1H, t, J=7.5 Hz), 7.45 (2H, t, J=7.5 Hz), 7.58 (2H, d, J=7.5 Hz)

(2) 3-Amino-5-(2-phenylethynyl)-1H-1,2,4-triazole

The synthesis method of Example 7-(2) was applied. The compound (5.63 g) obtained in (1) above, methanol (85 ml), metallic sodium (3.29 g) and aminoguanidine hydrochloride (15.8 g) were used as reagents to give 4.87 g of a pale-brown solid (yield 75%).

IR (KBr): 3380, 1617, 1593, 1538, 1500 cm$^{-1}$ $^1$H-NMR (DMSO-d$_6$) δ: 5.88 (2H, brs), 7.30 (1H, t, J=7.5 Hz), 7.42 (2H, t, J=7.5 Hz), 7.66 (2H, d, J=7.5 Hz), 12.00 (1H, brs)

(3) 5-Amino-1-[[methylamino(thiocarbonyl)]-3-(2-phenylethynyl)-1H-1,2,4-triazole The synthesis method of Example 7-(3) was applied. The compound (3.00 g) obtained in (2) above, 0.68N sodium hydroxide (25 ml), methyl isothiocyanate (2.75 g) and tetrahydrofuran (25 ml) were used as reagents and the mixture was stirred for 3 days. After the reaction, silica gel column chromatography (chloroform-methanol) and recrystallization from chloroform gave 209 mg of white powdery crystals (yield 5.0%).

Melting point: 212°–214° C.

IR (KBr): 3220, 2220, 1628, 1540, 1500 cm$^{-1}$ $^1$H-NMR (DMSO-d$_6$) δ: 3.04 (3H, s), 7.44 –7.54 (3H, m), 7.60 (2H, d, J=6.7 Hz), 8.33 (2H, brs), 10.14 (1H, brs)

EXAMPLE 44

5-Amino-3-(4-chlorophenyl)-1-[n-propylamino(thiocarbonyl)]-1H-1,2,4-triazole

The synthesis method of Example 7-(3) was applied. The compound (5.05 g) obtained in Example 4-(2), a 1N aqueous sodium hydroxide solution (30 ml), n-propyl isothiocyanate (4.0 ml) and tetrahydrofuran (15 ml) were used as reagents. The mixture was stirred at room temperature for 2 hours, neutralized with 3N hydrochloric acid and extracted with chloroform. After concentration, the solvent was distilled away under reduced pressure. The residue was subjected to silica gel column chromatography (chloroform) and recrystallization from ethyl acetate to give 706 mg of white crystals (yield 9.2%).

Melting point: 186°–188° C.

IR (KBr): 3400, 3300, 3050, 2950, 1660, 1600, 1580, 1555, 1520 cm$^{-1}$ $^1$H-NMR (DMSO-d$_6$) δ: 0.92 (3H, t, J=7.3 Hz), 1.68 (2H, sext, J=7.3 Hz), 3.58 (2H, t, J=7.3 Hz), 7.57 (2H, d, J=8.5 Hz), 8.06 (2H, d, J=8.5 Hz), 8.35 (2H, brs), 10.08 (1H, brs)

EXAMPLE 45

5-Amino-3-(4-chlorophenyl)-1-[n-pentylamino(thiocarbonyl)]-1H-1,2,4-triazole (1) n-Pentyl isothiocyanate To carbon disulfide (50 ml) was gradually added dropwise a mixed solution of triethylamine (9.6 ml) and amylamine (6.0 g) under ice-cooling over 15 minutes. The mixture was stirred for 1 hour under ice-cooling and carbon disulfide was distilled away under reduced pressure. Ether was added to the resulting solid for washing. The solid was collected by filtration and dissolved in chloroform (50 ml). Triethylamine (9.0 ml) was added under ice-cooling and ethyl chlorocarbonate (5.93 ml) was gradually added dropwise over 10 minutes. The mixture was stirred under ice-cooling for 15 minutes and at room temperature for 1 hour. After the reaction, 1N hydrochloric acid (75 ml) was added and the mixture was extracted with chloroform. The extract was washed with water and dried over magnesium sulfate. The solvent was distilled away under reduced pressure to give 8.12 g of colorless transparent liquid (yield 93%).

IR (neat) δ: 2950, 2850, 2100 cm$^{-1}$ $^1$H-NMR (DMSO-d$_6$) δ: 0.74–1.06 (3H, m), 1.14–1.50 (4H, m), 1.50–1.90(2H, m), 3.65 (2H, t, J=6.5 Hz) (2) 5-Amino-3-(4-chlorophenyl)-1-[n-pentylamino(thiocarbonyl)]-1H-1,2,4-triazole The synthesis method of Example 44 was applied. The compound (7.07 g) obtained in Example 4-(2), the compound (7.46 g) obtained in (1) above, a 1.13N aqueous sodium hydroxide solution (35 ml) and tetrahydrofuran (20 ml) were used as reagents. The mixture was stirred at room temperature for 16 hours, extracted and applied to silica gel column chromatography (chloroform) and recrystallization from chloroform to give 235 mg of white crystals (yield 2%).

Melting point: 139°–141° C.

IR (KBr): 3300, 3050, 2910, 1655 cm$^{-1}$ $^1$H-NMR (DMSO-d$_6$) δ: 0.80–1.04 (3H, t, J=6.7 Hz), 1.20–1.57 (4H, m), 1.57–1.70 (2H, m), 3.63 (2H, t, J=6.6 Hz), 7.57 (2H, d, J=8.6 Hz), 8.05 (2H, d, J=8.6 Hz), 8.38 (2H, brs), 10.10 (1H, brs)

EXAMPLE 46

5-Amino-3-(4-chlorophenyl)-1-[isopropylamino(thiocarbonyl)]- 1H-1,2,4-triazole (1) Isopropyl isothiocyanate The synthesis method of Example 45-(1) was applied. Isopropylamine (6.20 g), carbon disulfide (50 ml), triethylamine (14.6 ml), ethyl chlorocarbonate (9.0 ml), triethylamine (14.0 ml) and chloroform (50 ml) were used as reagents. After the reaction, a colorless transparent liquid 8.13 g was obtained (yield 78%).

IR (neat) δ: 3000, 2950, 2150, 2100, 1995, 1500 cm$^{-1}$ $^1$H-NMR (DMSO-d$_6$) δ: 1.31 (6H, d, J=6.5 Hz), 4.09 (1H, hept, J=6.5 Hz)

(2) 5-Amino-3-(4-chlorophenyl)-1-[isopropylamino(thiocarbonyl)]-1H-1,2,4-triazole The synthesis method of Example 44 was applied. The compound (6.83 g) obtained in Example 4-(2), the compound (6.03 g) obtained in (1) above, a 1N aqueous sodium hydroxide solution (40 ml) and tetrahydrofuran (20 ml) were used as reagents. The mixture was stirred at room temperature for 17 hours and subjected to silica gel column chromatography (chloroform) and recrystallization from ethyl acetate to give 1.79 g of white crystals.

Melting point: 177°–179° C.

IR (KBr): 33° C., 1635, 1600, 1580, 1510 cm$^{-1}$ $^1$H-NMR (DMSO-d$_6$) δ: 1.30 (6H, d, J=6.6 Hz), 4.40–4.65 (1H, m), 7.57 (2H,d, J=8.6 Hz), 8.07 (2H, d, J=8.6 Hz), 8.35 (2H,brs), 9.68 (1H, brs)

EXAMPLE 47

5-Amino-1-[n-propylamino(thiocarbonyl)]-1H-1,2,4-triazole

The synthesis method of Example 1-(3) was applied. 3-Amino-1H-1,2,4-triazole (4.00 g), dimethylformamide (30 ml) and n-propyl isothiocyanate (5.7 ml) were used as reagents. After the reaction, the reaction mixture was purified by silica gel column chromatography (hexane-ethyl acetate) to give 3.07g of a 1:1 mixture of 5-amino-1-[n-propylamino(thiocarbonyl)]-1H-1,2,4-triazole and 3-amino-1-[n-propylamino(thiocarbonyl)]-1H-1,2,4-triazole as a white solid (yield 35%). The solid was applied to high performance liquid chromatography (acetonitrile-water) and recrystallization from hexane-ethyl acetate to give colorless transparent thin film crystals.

Melting point: 117°–118° C.

IR (KBr): 3300, 1638, 1503 cm$^{-1}$ $^1$H-NMR (DMSO-d$_6$), : 0.88 (3H, t, J=7.4 Hz), 1.63 (2H, sext, J=7.4 Hz), 3.53 (2H, t, J=7.4 Hz), 7.62 (1H, s), 8.18 (2H, brs), 10.03 (1H, brs)

EXAMPLE 48

5-Amino-1-[cyclohexylamino(thiocarbonyl)]-1H-1,2,4-triazole

The synthesis method of Example 1-(3) was applied. 3-Amino-1H-1,2,4-triazole (6.07 g), dimethylformamide (30 ml) and cyclohexyl isothiocyanate (20.5 ml) were used as reagents. After the reaction, the mixture was subjected to silica gel column chromatography (hexane-ethyl acetate), whereby 2.26 g of a white solid was obtained (yield 14%). The, solid was subjected to recrystallization from ethyl acetate to give colorless transparent crystals.

Melting point: 168°–170° C.

IR (KBr): 3380, 3270, 3200, 2900, 2830, 1633, 1562, 1505 cm$^{-1}$ $^1$H-NMR (DMSO-d$_6$) δ: 1.13 (1H, tq, J=12.6, 3.4 Hz), 1.30 (2H, tq, J=12.9, 3.4 Hz), 1.51 (2H, dq, J=11.7, 3.4 Hz), 1.60 (1H, dt, J=12.8, 3.3 Hz), 1.73 (2H, dt, J=13.5, 3.1 Hz), 1.85 (2H, dd, J=12.2, 2.9 Hz), 4.16 (1H, brs), 7.62 (1H, s), 8.18 (2H, brs), 9.62 (1H, brs)

EXAMPLE 49

5-Amino-1-[benzylamino(thiocarbonyl)]-1H-1,2,4-triazole

The synthesis method of Example 1-(3) was applied. 3-Amino-1H-1,2,4-triazole (4.00 g), dimethylformamide (20 ml) and benzyl isothiocyanate (7.0 ml) were used as reagents. After the reaction, white solid was filtered off and the filtrate was extracted with ethyl acetate. The solid previously obtained was combined and the solids were subjected to recrystallization from ethanol to give 3.99 g of white needle crystals (yield 36%).

Melting point: 157°–158° C.

IR (KBr): 3380, 3270, 3070, 1633, 1618, 1512 cm$^{-1}$ $^1$H-NMR (DMSO-d$_6$) δ: 4.81 (2H, s), 7.25 (1H, tt, J=6.8, 1.8 Hz), 7.30–7.36 (4H, m), 7.66 (1H, s), 8.20 (2H, brs), 10.54 (1H, brs)

EXAMPLE 50

5-amino-1-[5-hydroxypentylamino(thiocarbonyl)]-1H-1,2,4-triazole (1) 5-Hydroxypentyl isothiocyanate The synthesis method of Example 45-(1) was applied. 5-Hydroxypentylamine (6.00 g), carbon disulfide (40 ml), triethylamine (8.3 ml), ethyl chlorocarbonate (5.4 ml), triethylamine (8.3 ml) and chloroform (20 ml) were used as reagents. After the reaction, a yellow liquid was quantitatively obtained.

IR (neat) δ: 3290, 2910, 2860, 2070, 1695, 1515 cm$^{-1}$ $^1$H-NMR (CDCl$_3$) δ: 1.47–1.55 (2H, m), 1.57–1.65 (2H, m), 1.75 (2H, quint, J=6.6 Hz), 1.92 (1H, brs), 3.54 (2H, t, J=6.6 Hz), 3.66 (2H, t, J=6.3 Hz)

(2) 5-Amino-1-[5-hydroxypentylamino(thiocarbonyl)]-1H-1,2,4-triazole

The synthesis method of Example 1-(3) was applied. 3-Amino-1H-1,2,4-triazole (4.00 g), dimethylformamide (25 ml) and 5-hydroxypentyl isothiocyanate (9.24 g) were used as reagents. After the reaction, silica gel column chromatography (chloroform-methanol) was applied to give 2.06 g of white crystals (yield 19%). The crystals were subjected to recrystallization from chloroform to give white crystals.

Melting point: 108°–109° C.

IR (KBr): 3290, 3130, 2940, 2880, 1634, 1521 cm$^{-1}$ $^1$H-NMR (DMSO-d$_6$) δ: 1.27–1.36 (2H, m), 1.45 (2H, quint, J=6.5 Hz), 1.62 (2H, quint, J=7.4 Hz), 3.39 (2H, dt, J=6.5, 5.2 Hz), 3.57 (2H, q, J=7.4 Hz), 4.34 (1H, t, J=5.2 Hz), 7.63 (1H, s), 8.19 (2H, brs), 10.02 (1H, brs)

EXAMPLE 51

[5-Amino-3-(4-chlorophenyl)-1H-1,2,4-triazol-1-yl]-thiocarbonylaminoacetic acid (1) Methyl [5-amino-3-(4-chlorophenyl)-1H-1,2,4-triazol-1-yl]-dithiocarbonate To a compound (10.0 g) obtained in Example 4-(2) in dimethylformamide (10 ml) was added carbon disulfide (3.6 ml) under ice-cooling. Then, an aqueous solution (6.5 ml) of potassium hydroxide (3.00 g) was dropwise added over 30 minutes. The mixture was stirred on an ice bath for 30 minutes, and methyl iodide (3.4 ml) was gradually added. Thirty minutes later, the ice bath was removed and the mixture was stirred at room temperature for 2.5 hours. The resulting crystals were collected by filtration, washed with water, dried and subjected to recrystallization from ethanol to give 4.21 g of pale-yellow crystals (yield 28%).

Melting point: 260°–263° C.

IR (KBr): 3350, 1648, 1600, 1575, 1530 cm$^{-1}$ $^1$H-NMR (DMSO-d$_6$) δ: 2.63 (3H, s), 7.59 (2H, d, J=8.3 Hz), 8.01 (2H, d, J=8.3 Hz), 8.64 (2H, brs)

(2) Methyl [5-amino-3-(4-chlorophenyl)-1H-1,2,4-triazol-1-yl]-thiocarbonylaminoacetate The compound (3.62 g) obtained in (1) above, methanol (80 ml), a 5M sodium methoxide-methanol solution (2.9 ml) and glycine methyl ester hydrochloride (1.83 g) were stirred with reflux under heating for 19 hours. After the reaction, the reaction mixture was cooled to room temperature. The resulting crystals were collected by filtration, washed with methanol and dried to give 2.94 g of white crystals (71%).

Melting point: 142°–145° C.

IR (KBr): 3400, 3310, 1735, 1648, 1600, 1507 cm$^{-1}$ $^1$H-NMR (DMSO-d$_6$) δ: 3.69 (3H, s), 4.38 (2H, s), 7.59 (2H, d, J=8.6 Hz), 8.05 (2H, d, J=8.6 Hz), 8.36 (2H, brs), 10.29 (1H, brs) (3) [5-Amino-3-(4-chlorophenyl)-1H-1,2,4-triazol-1-yl]thiocarbonylaminoacetic acid The reaction mixture of the compound (701 mg) obtained in (2) above, 0.1M phosphate buffer (pH 7.5, 200 ml), acetonitrile (20 ml) and swine liver esterase "Amano" (350 mg) was stirred in an oil bath at 40° C. for 13 days. After the reaction, the reaction mixture was poured in a saturated sodium hydrogencarbonate solution and the aqueous layer was washed with ethyl acetate. 2N Hydrochloric acid was added to an aqueous layer to adjust its pH to 3, which led to the precipitation of solid. The precipitated crystals were collected by filtration and washed with water and ethyl acetate, which was followed by drying to give brown crystals. The crystals were washed with ethanol to give 384 mg of pale-brown crystals (yield 57%).

Melting point: 213°–216° C. (decomposition)

IR (KBr): 3360, 3300, 1690, 1640, 1600, 1513 cm$^{-1}$ $^1$H-NMR (DMSO-d$_6$)δ: 4.29 (2H, d, J=5.8 Hz), 7.59 (2H, d, J=8.4 Hz), 8.04 (211, d, J=8.4 Hz), 8.36 (2H, brs), 10.18 (1H, t, J=5.8 Hz), 12.9 (1H, brs)

EXAMPLE 52

5-Amino-3-(4-chlorophenyl)-1-(methylaminocarbonyl)-1H-1,2,4-triazole

The synthesis method of Example 7-(3) was applied. The compound (4.00g) obtained in Example 4-(2), methyl isocyanate (1.5 ml), a 0.73N aqueous sodium hydroxide solution (30 ml) and tetrahydrofuran (25 ml) were used as reagents. The mixture was reacted at 0° C. for 1 hour and the resulting crystals were washed with hexane-ethyl acetate to give 3.28 g of white powdery crystals (yield 63%).

Melting point: 193°–196° C.

IR (KBr): 3380, 3260, 3110, 1725, 1632, 1530 cm$^{-1}$ $^1$H-NMR (DMSO-d$_6$) δ: 2.81 (3H, d, J=4.7 Hz), 7.31 (2H, brs), 7.55 (2H, d, J=8.5 Hz), 7.98 (2H, d, J=8.5 Hz), 8.16 (1H, m)

EXAMPLE 53

5-Amino-1-(methylaminocarbonyl)-1H-1,2,4-triazole

The synthesis method of Example 1-(3) was applied. 3-Amino-1H-1,2,4-triazole (5.00 g), dimethylformamide (30 ml) and methyl isocyanate (4.0 ml) were used as reagents. The mixture was stirred at room temperature for 18 hours and 6.83 g of the resulting solid (yield 81%) was collected by filtration. The obtained solid was recrystallized from ethyl acetate to give colorless transparent crystals.

Melting point: 192°–195° C.

IR (KBr): 3370, 3100, 1707, 1643, 1555, 1504 cm$^{-1}$ $^1$H-NMR (DMSO-d$_6$) δ: 2.73(3H, d, J=4.7 Hz), 7.15(2H, brs), 7.53(1H, s), 8.11(1H, brs)

EXAMPLE 54

5-Amino-1-[dimethylamino(thiocarbonyl)]-1H-1,2,4-triazole

To a solution of 3-amino-1H-1,2,4-triazole (4.00 g) and pyridine (30 ml) was added dimethylthiocarbamoyl chloride (6.46 g). The mixture was stirred at room temperature for 24 hours, and the resulting matter was filtered away and the filtrate was concentrated. The condensate was poured into a saturated aqueous sodium hydrogen-carbonate solution, extracted with ethyl acetate and washed with saturated brine. The solvent was distilled away under reduced pressure and the residue was subjected to silica gel column chromatography (chloroform-methanol) to give 1.63 g of a white solid (yield 20%) of a 2:1 mixture of 5-amino-1-[dimethylamino(thiocarbonyl)]-1H-1,2,4-triazole and 3-amino-1-[dimethylamino(thiocarbonyl)]-1H-1,2,4-triazole. The solid was subjected to recrystallization from ethyl acetate, whereby white crystals were obtained.

Melting point: 139.5°–140.5° C.

IR (KBr): 3360, 1645, 1516 cm$^{-1}$ $^1$H-NMR (DMSO-d$_6$) δ: 3.17 (3H, s), 3.42 (3H, s), 6.80 (2H, brs), 7.53 (1H, s)

EXAMPLE 55

6-Methyl-2-phenyl-1,2,4-triazolo[1,5-a]-1,3,5-triazine-7(6H)-thione

A solution of the compound (930 mg) obtained in Example 1-(3) and diethoxymethyl acetate (15 ml) was stirred at room temperature for 158 hours. After the reaction, the precipitated crystals were collected by filtration to give 895 mg of white powdery crystals (yield 92%).

Melting point: >: 300° C.

IR (KBr): 1595, 1583, 1560 cm$^{-1}$ $^1$H-NMR (DMSO-d$_6$) δ: 3.85 (3H, s), 7.55–7.59 (3H, m), 8.17–8.22 (2H, m), 8.88 (1H, s)

EXAMPLE 56

2-(4-Cyanophenyl)-6-methyl-1,2,4-triazolo[1,5-a]-1,3,5-triazine-7(6H)-thione

The synthesis method of Example 55 was applied. The compound (708 mg) obtained in Example 2-(4) and diethoxymethyl acetate (6.10 g) were used as reagents. The mixture was reacted at 80° C. for 2.5 hours to give 701 mg of white powdery crystals (yield 95%).

Melting point: >300° C.

IR (KBr): 3400, 2210, 1600, 1550 cm$^{-1}$ $^1$H-NMR (DMSO-d$_6$) δ: 3.85 (3H, s), 8.05 (2H, d, J=8.5 Hz), 8.35 (2H, d, J=8.5 Hz), 8.93 (1H, s)

EXAMPLE 57

6-Methyl-2-(p-tolyl)-1,2,4-triazolo[1,5-a]-1,3,5-triazine-7(6H)-thione

The synthesis method of Example 55 was applied. The compound (661 mg) obtained in Example 3-(3) and diethoxymethyl acetate (5 ml) were used as reagents. The mixture was reacted at 85° C. for 2 hours to give 664 mg of white powdery crystals (yield 97%).

Melting point: 277°–279° C.

IR (KBr): 1583, 1557 cm$^{-1}$ $^1$H-NMR (DMSO-d$_6$) δ: 2.39 (3H, s), 3.84 (3H, s), 7.37 (2H, d, J=8.1 Hz), 8.08 (: 2H, d, J=8.1 Hz), 8.86 (1H, s)

EXAMPLE 58

2-(4-Chlorophenyl)-6-methyl-1,2,4-triazolo[1,5-a]-1,3,5-triazine-7(6H)-thione

The synthesis method of Example 55 was applied. The compound (4.48 g) obtained in Example 4-(3) and diethoxymethyl acetate (22 ml) were used as reagents. The mixture was reacted at 90° C. for 1.5 hours to give 4.44 g of pale-yellow crystals (yield 96%).

Melting point: >300° C.

IR (KBr): 1583, 1557 cm$^{-1}$ $^1$H-NMR (DMSO-d$_6$) δ: 3.85 (3H, s), 7.64 (2H, d, J=8.5 Hz), 8.19 (2H, d, J=8.5 Hz), 8.89 (1H, s)

EXAMPLE 59

2-(3-(Chlorophenyl)-6-methyl-1,2,4-triazolo[1,5-a]-1,3,5-triazine-7(6H)-thione

The synthesis method of Example 55 was applied. The compound (272 mg) obtained in Example 5-(4) and diethoxymethyl acetate (3.0 g) were used as reagents. The mixture was reacted at 80° C. for 1.5 hours to give 272 mg of a white powder (yield 82%).

Melting point: 265°–266° C.

IR (KBr): 3400, 1585, 1505 cm$^{-1}$ $^1$H-NMR (DMSO-d$_6$) δ: 3.85(3H, s), 7.58–7.72(2H, m), 8.09–8.21(2H, m), 8.90(1H,s)

EXAMPLE 60

2-(2-(Chlorophenyl)-6-methyl-1,2,4-triazolo[1,5-a]-1,3,5-triazine-7(6H)-thione

The synthesis method of Example 55 was applied. The compound (288 mg) obtained in Example 6-(3) and diethoxymethyl acetate (2.60 g) were used as reagents. The mixture was reacted at 80° C. for 1.5 hours to give 264 mg of white powdery crystals (yield 88%).

Melting point: 2145°–246° C.

IR (KBr): 3450, 3050, 1585, 1560, 1500 cm$^{-1}$ $^1$H-NMR (DMSO-d$_6$) δ: 3.85(3H, s), 7.49–7.61(2H, m), 7.61–7.71(1H, m), 7.90–8.01(1H, m), 8.92(1H, s)

EXAMPLE 61

2-(4-Fluorophenyl)-6-methyl-1,2,4-triazolo[1,5-a]-1,3,5-triazine-7(6H)-thione

The synthesis method of Example 55 was applied. The compound (1.20 g) obtained in Example 7-(3) and diethoxymethyl acetate (7.80 ml) were used as reagents. The mixture was reacted at 90° C. for 2 hours to give 1.20 g of white powdery crystals (yield 96%).

Melting point: >300° C.

IR(KBr): 1600, 1565 cm$^{-1}$ $^1$H-NMR (DMSO-d$_6$)&: 3.84(3H, s), 7.41(2H, t, J=8.0 Hz), 8.23(2H, dd, J=8.0, 6.0 Hz), 8.90(1H, s)

EXAMPLE 62

2-(4-Bromophenyl)-6-methyl-1,2,4-triazolo[1,5-a]-1,3,5-triazine-7(6H)-thione

The synthesis method of Example 55 was applied. The compound (1.70 g) obtained in Example 8-(3) and diethoxymethyl acetate (8.90 ml) were used as reagents. The mixture was reacted at 90° C. for 1 hour to give 1.71 g of white powdery crystals (yield 97%).

Melting point: >300° C.

IR(KBr): 3400, 3010, 1600, 1550, 1505 cm$^{-1}$ $^1$H-NMR (DMSO-d$_6$) δ: 3.84(3H, s), 7.78(2H, d, J=8.5 Hz), 8.12(2H, d, J=8.5 Hz), 8.90(1H, s)

EXAMPLE 63

6-Methyl-2-(4-trifluoromethylphenyl)-1,2,4-triazolo[1,5-a]-1,3,5-triazine-7(6H)-thione The synthesis; method of Example 55 was applied. The compound (1.12 g) obtained in Example 9-(2) and diethoxymethyl acetate (6.10 ml) were used as reagents. The mixture was reacted at 90° C. for 1.5 hours to give 1.08 g of white powdery crystals (yield 93%).

Melting point: 270°–272° C.

IR (KBr): 1600, 1580, 1530 cm$^{-1}$ $^1$H-NMR (DMSO-d$_6$) δ: 3.85(3H, s), 7.95(2H, d, J=8.0 Hz), 8.39(2H, d, J=80 Hz), 8.92(1H, s)

EXAMPLE 64

2-(4-Methoxyphenyl)-6-methyl-1,2,4-triazolo[1,5-a]-1,3,5-triazine-7(6H)-thione

The synthesis method of Example 55 was applied. The compound (265 mg) obtained in Example 10-(4) and diethoxymethyl acetate (2.60 g) were used as reagents. The mixture was reacted at 90° C. for 1.5 hours to give 267 mg of white crystals (yield 98%).

Melting point: >300° C.

IR (KBr): 3400, 1605, 1590, 1560 cm$^{-1}$ $^1$H-NMR (DMSO-d$_6$) δ: 3.84 (3H, s), 3.85 (3H, s), 7.12 (2H, d, J=8.8 Hz), 8.12(2H, d, J=8.8 Hz), 8.86 (1H, s)

EXAMPLE 65

2-[4-(Ethoxalylamino)phenyl]-6-methyl-1,2,4-triazolo[1,5-a]-1,3,5-triazine-7(6H)-thione The synthesis, method of Example 55 was applied. The compound (884 mg) obtained in Example 13-(2) and diethoxymethyl acetate (8.2 g) were used as reagents. The mixture was reacted at 100 ° C. for 2 hours to give 249 mg of pale-yellow crystals (yield 27%).

Melting point: 2615°–262° C.

IR (KBr): 3450, 3360, 3310, 1710, 1600, 1580, 1565, 1515 cm$^{-1}$ $^1$H-NMR (DMSO-d$_6$) δ: 1.33 (3H, t, J=7 Hz), 3.84 (3H, s), 4.33 (3H, q, J=7 Hz), 7.95 (2H, d, J=8.7 Hz), 8.18 (2H, d, J=8.7 Hz), 8.89 (1H, s), 11.05 (1H, brs)

EXAMPLE 66

6-Methyl-2-(4-phenylphenyl)-1,2,4-triazolo[1,5-a]-1,3,5-triazine- 7(6H)-thione

The synthesis method of Example 55 was applied. The compound (595 mg) obtained in Example 15-(3) and diethoxymethyl acetate (8.03 g) were used as reagents. The mixture was reacted at 80° C. for 2 hours to give 525 mg of white powdery crystals (yield 86%).

Melting point: 297°–299° C.

IR (KBr): 3350, 1585, 1550, 1530 cm$^{-1}$ $^1$H-NMR (DMSO-d$_6$) δ: 3.85(3H, s), 7.35–7.60(3H, m), 7.77(2H, d, J=7.0 Hz), 7.89(2H, d, J=8.4 Hz), 8.28(2H, d, J=8.4 Hz), 8.90(1H, s)

EXAMPLE 67

2-(2,14-Dichlorophenyl)-6-methyl-1,2,4-triazolo[1,5-a]-1,3,5-triazine-7((6H)-thione The synthesis method of Example 55 was applied. The compound (153 mg) obtained in Example 16-(3) and diethoxymethyl acetate (4.0 g) were used as reagents. The mixture was reacted at 80° C. for 2.5 hours to give 132 mg of white powdery crystals (yield 84%).

Melting point: 277°–279° C.

IR (KBr): 3350, :3005, 1730, 1580, 1540, 1500 cm$^{-1}$ $^1$H-NMR (DMSO-d$_6$) δ: 3.85(3H, s), 7.64(1H, dd, J=8.4, 2.0 Hz), 7.86(1H, d, J=2.0 Hz), 8.02(1H, d, J=8.4 Hz), 8.92(1H, s)

EXAMPLE 68

2-(3,)$_4$-Dichlorophenyl)-6-methyl-1,2,4-triazolo[1,5-a]-1,3,5-triazine-7((6H)-thione The synthesis method of Example 55 was applied. The compound (241 mg) obtained in Example 17-(3) and diethoxymethyl acetate (5.0 g) were used as reagents. The mixture was reacted at 80° C. for 2.5 hours to give 199 mg of white powdery crystals (yield 80%).

Melting point: 282°–284° C.

IR (KBr): 3400, 3050, 1600, 1565, 1550, 1500 cm$^{-1}$ $^1$H-NMR (DMSO-d$_6$) δ: 3.85(3H, s), 7.85(1H, d, J=8.4 Hz), 8.13(1H, dd, J=8.4, 1.9 Hz), 8.28(1H, d, J=1.9 Hz), 8.92(1H, s)

EXAMPLE 69

2-(4-(Chloro-2-methoxyphenyl)-6-methyl-1,2,4-triazolo[1,5-a]-1,3,5-triazine-7(6H)-thione The synthesis method of Example 55 was applied. The compound (1.51 g) obtained in Example 18-(3) and diethoxymethyl acetate (16 g) were used as reagents. The mixture was reacted at 90° C. for 2.5 hours. The resulting crystals were collected by filtration and subjected to recrystallization from dimethylformamide-water to give 1.07 g of white crystals (yield 68%).

Melting point: 208°–210° C.

IR (KBr): 3400, 3050, 2950, 1590, 1560 cm$^{-1}$ $^1$H-NMR (DMSO-d$_6$) δ: 3 84 (3H, s), 3.89 (3H, s), 7.17 (1H, dd, J=8.3, 1.8 Hz), 7.31 (1H, d, J=1.8 Hz), 7.87 (1H, d, J=8.3 Hz), 8.87 (1H, s)

EXAMPLE 70

2-(4-Chloro-2-n-propoxyphenyl)-6-methyl-1,2,4-triazolo-[1,5-a]-1,3,5-triazine-7(6H)-thione The synthesis method of Example 55 was applied. The compound (880 mg) obtained in Example 19-(3) and diethoxymethyl acetate (8.8 g) were used as reagents. The mixture was reacted at 90° C. for 2.5 hours to give 459 mg of white crystals (yield 53%).

Melting point: 160°–162° C.

IR (KBr): 3400, 2920, 2870, 1600, 1560, 1500 cm$^{-1}$ $^1$H-NMR (DMSO-d$_6$) δ: 1.09 (3H, t, J=7.4 Hz), 1.66–1.87 (2H, m), 3.84 (3H, s), 4.08 (2H, t, J=6.1 Hz), 7.16 (1H, dd, J=8.3, 1.9 Hz), 7.27 (1H, d, J=1.9 Hz), 7.93 (1H, d, J=8.3 Hz), 8.86 (1H, s)

EXAMPLE 71

2-(3,5-di-tert-Butyl-4-hydroxyphenyl)-6-methyl-1,2,4-triazolo[1,5-a]-1,3,5-triazine-7(6H)-thione The synthesis method of Example 55 was applied. The compound (1.2 g) obtained in Example 20-(5) and diethoxymethyl acetate (5.4 ml) were used as reagents. The mixture was reacted at 90° C. for 45 minutes to give 997 mg of white powdery crystals (yield 81%).

Melting point: >300° C.

IR (KBr): 3600, 3250, 2900, 1580, 1500, 1470 cm$^{-1}$ $^1$H-NMR (DMSO-d$_6$) δ: 1.45(18H, s), 3.83(3H, s), 7.56 (1H, brs), 7.98(2H, s), 8.85(1H, s)

EXAMPLE 72

2-(2-(Carboxy-4,5-dichlorophenyl)-6-methyl-1,2,4-triazolo[1,5-a]-1,3,5-triazine-7(6H)-thione The synthesis method of Example 55 was applied. The compound (217 mg) obtained in Example 21-(2) and diethoxymethyl acetate (2.0 g) were used as reagents. The mixture was reacted at 100° C. for 20 minutes to give 100 mg of white crystals (yield 45%).

Melting point: 298°–300° C.

IR (KBr): 3400, 3080, 2820, 2510, 1940, 1720, 1585, 1555, 1505 cm$^{-1}$ $^1$H-NMR (DMSO-d$_6$) δ: 3.84 (3H,s), 8.00 (1H, s), 8.08 (1H,s), 8.91 (1H, s), 13.55 (1H, brs)

EXAMPLE 73

2-(2-Furyl)-6-methyl-1,2,4-triazolo[1,5-a]-1,3,5-triazine-7(6H)-thione

The synthesis method of Example 55 was applied. The compound (1.2 g) obtained in Example 22-(2) and diethoxymethyl acetate (8.8 ml) were used as reagents. The mixture was reacted at 90° C. for 1 hour to quantitatively give white powdery crystals.

Melting point: >300° C.

IR (KBr): 1615, 1580 cm$^{-1}$ $^1$H-NMR (DMSO-d$_6$) δ: 3.83(3H, s), 6.74(1H, dd, J=3.4, 1.6 Hz), 7.28(1H, d, J=3.4 Hz), 7.98(1H, d, J=1.6 Hz), 8.88(1H, s)

EXAMPLE 74

6-Methyl-2-(2-thienyl)-1,2,4-triazolo[1,5-a]-1,3,5-triazine

The synthesis method of Example 55 was applied. The compound (1.2 g) obtained in Example 23-(3) and diethoxymethyl acetate (8.20 ml) were used as reagents. The mixture was reacted at 90° C. for 1 hour to quantitatively give white powdery crystals.

Melting point: >300° C.

IR (KBr): 1580, 1460, 1415 cm$^{-1}$ $^1$H-NMR (DMSO-d$_6$) δ: 3.83(3H, s), 7.26(1H, dd, J=5.0, 3.8 Hz), 7.80–7.95(1H, m),8.87(1H, s)

EXAMPLE 75

2-(6-(Chloro-3-pyridyl)-6-methyl-1,2,4-triazolo[1,5-a]-1,3,5-triazine-7(61H)-thione The synthesis method of Example 55 was applied. The compound (500 mg) obtained in Example 25-(2) and diethoxymethyl acetate (3.0 ml) were used as reagents. The mixture was reacted at 90° C. for 1 hour to quantitatively give white powdery crystals.

Melting point: 263°–265° C.

IR (KBr): 1590, 1540 cm$^{-1}$ $^1$H-NMR (DMSO-d$_6$) δ: 3.85(3H, s), 7.73(1H, d, J=8.0 Hz), 8.53(1H, dd, J=8.0, 2.0 Hz), 8.93(1H, s), 9.12(1H, d, J=2.0 Hz)

EXAMPLE 76

2-(5-Chloro-2-pyridyl)-6-methyl-1,2,4-triazolo[1,5-a]-1,3,5-triazine-7(6H)-thione The synthesis method of Example 55 was applied. The compound (400 mg) obtained in Example 26-(5) and diethoxymethyl acetate (2.4 ml) were used as reagents. The mixture was reacted at 90° C. for 3 hours to give 340 mg of white powdery crystals (yield 82%).

Melting point: >300° C.

IR (KBr): 3000, 1580, 1550 cm$^{-1}$ $^1$H-NMR (DMSO-d$_6$) δ: 3.89(3H, s), 8.14(1H, dd, J=8.0, 2.0 Hz), 8.29(1H, d, J=8.0Hz), 8.83(1H, d, J=2.0 Hz), 8.94(1H, s)

EXAMPLE 77

6-Methyl-2-(1-naphthyl)-1,2,4-triazolo[1,5-a]-1,3,5-triazine-7(6H)-thione

The synthesis method of Example 55 was applied. The compound (334 mg) obtained in Example 27-(5) and diethoxymethyl acetate (2.48 g) were used as reagents. The mixture was reacted at 90° C. for 2 hours to give 317 mg of white crystals (yield 92%).

Melting point: 278°–279° C.

IR (KBr): 3450, 1580, 1510 cm$^{-1}$ $^1$H-NMR (DMSO-d$_6$) δ: 3.88 (3H, s), 7.60–7.80 (3H, m), 8.08 (1H, d, J=8.7 Hz), 8.17 (1H, d, J=8.1 Hz), 8.38 (1H, d, J=7.2 Hz), 8.95 (1H, s), 9.23 (1H, d, J-=8.3 Hz)

EXAMPLE 78

6-Methyl-1,2,4-triazolo[1,5-a]-1,3,5-triazine-7(6H)-thione

The synthesis method of Example 55 was applied. The compound (1.49 g) obtained in Example 29 and diethoxymethyl acetate (12 ml) were used as reagents. The mixture was reacted at 75° C. for 2 hours to give 1.39 g of white crystals (yield 88%). The crystals were subjected to recrystallization from acetone to give white crystals.

Melting point: 238°–240° C.

IR (KBr): 2300, 1585, 1560 cm$^{-1}$ $^1$H-NMR (DMSO-d$_6$) δ: 3.35 (3H, s), 8.57 (1H, s), 8.86 (1H, s)

EXAMPLE 79

2-Acetylamino-6-methyl-1,2,4-triazolo[1,5-a]-1,3,5-triazine-7(6H)-thione

The synthesis method of Example 55 was applied. The compound (1.02 g) obtained in Example 32 and diethoxymethyl acetate (10 ml) were used as reagents. The mixture was reacted at 100° C. for 5.5 hours to give 925 mg of white crystals (yield 87%).

Melting point: >300° C.

IR (KBr): 3400, 1722, 1600, 1551, 1522 cm$^{-1}$ $^1$H-NMR (DMSO-d$_6$) δ: 2.15 (3H, brs), 3.81 (3H, s), 8.83 (1H, s), 11.03 (1H, brs)

EXAMPLE 80

2-[(Dimethylaminomethylidene)amino]-6-methyl-1,2,4-triazolo[1,5-a]-1,3,5-triazine-7(6H)-thione The synthesis method of Example 55 was applied. The compound (486 mg) obtained in Example 33 and diethoxymethyl acetate (5 ml) were used as reagents. The mixture was reacted at 95° C. for 2 hours to give 282 mg of pale-brown crystals (yield 56%).

Melting point: >300° C.

IR (KBr): 3400, 3020, 2910, 1632, 1577, 1506 cm$^{-1}$ $^1$H-NMR (DMSO-d$_6$) δ: 3.02 (3H, s), 3.14 (3H, s), 3.78 (3H, s), 8.52 (1H, s), 8.71 (1H, s)

EXAMPLE 81

2-(Ethoxalylamino)-6-methyl-1,2,4-triazolo[1,5-a]-1,3,5-triazine-7(6H)-thione

The synthesis method of Example 55 was applied. The compound (551 mg) obtained in Example 35 and diethoxymethyl acetate (8 ml) were used as reagents. The mixture was reacted at 90° C. for 2 hours to give 442 mg of white powdery crystals (yield 78%).

Melting point: 280°–282° C.

IR (KBr): 3400, 3300, 1724, 1598, 1577, 1543 cm$^{-1}$ $^1$H-NMR (DMSO-d$_6$) δ: 1.31 (3H, t, J=7.1 Hz), 3.82 (3H, s), 4.32 (2H, q, J=7.1 Hz), 8.86 (1H, s), 11.9 (1H, brs)

EXAMPLE 82

2-Benzoylamino-6-methyl-1,2,4-triazolo[1,5-a]-1,3,5-triazine-7(6H)-thione

The synthesis method of Example 55 was applied. The compound (290 mg) obtained in Example 36 and diethoxymethyl acetate (3 ml) were used as reagents. The mixture was reacted at 1J0° C. for 3 hours to give 223 mg of white crystals (yield 74%).

Melting point: 273°–276° C.

IR (KBr): 3400, 3290, 3070, 1700, 1614, 1545 cm$^{-1}$ $^1$H-NMR (DMSO-d$_6$)(a: 3.84 (3H, s), 7.53 (2H, t, J=7.4 Hz), 7.63 (1H, t, J=7.4 Hz), 8.03 (2H, d, J=7.4 Hz), 8.86 (1H, s), 11.49 (1H, brs)

EXAMPLE 83

2-[(N-Benzylidene)amino]-6-methyl-1,2,4-triazolo[1,5-a]-1,3,5-triazine-7 (6H)-thione The synthesis method of Example 55 was applied. The compound (783 mg) obtained in Example 37 and diethoxymethyl acetate (5 ml) were used as reagents. The mixture was reacted at 90° C. for 1.5 hours to give 757 mg of white powdery crystals (yield 93%).

Melting point: >: 300° C.

IR (KBr): 3020, 1570 cm$^{-1}$ $^1$H-NMR (trifluoroacetic acid-d) δ: 4.06 (3H, s), 7.63 (2H, t, J=7.3 Hz), 7.79 (1H,t, J=7.3 Hz), 8.03 (2H, d, J=7.3 Hz), 8.77 (1H, s), 9.93 (1H, s)

EXAMPLE 84

2-Anilino-6-methyl-1,2,4-triazolo[1,5-a]-1,3,5-triazine-7(6H)-thione

The synthesis method of Example 55 was applied. The compound (500 mg) obtained in Example 38-(3) and diethoxymethyl acetate (3 ml) were used as reagents. The mixture was reacted at 90° C. for 1.5 hours to give 285 mg of yellow powdery crystals (yield 55%).

Melting point: >: 300° C.

IR (KBr): 3290, 3160, 3030, 1640, 1580, 1560 cm$^{-1}$ $^1$H-NMR (DMSO-d$_6$) δ: 3.81 (3H, s), 6.95 (1H, t, J=7.6 Hz), 7.32 (2H, t, J=7.6 Hz), 7.70 (2H, d, J=7.6 Hz), 8.78 (1H, s), 10.02 (1H, brs)

EXAMPLE 85

6-Methyl-2-phenoxy-1,2,4-triazolo[1,5-a]-1,3,5-triazine-7(6H)-thione

The synthesis method of Example 55 was applied. The compound (2.08 g) obtained in Example 39-(2) and diethoxymethyl acetate (10 ml) were used as reagents. The mixture was reacted at 100 ° C. for 1.5 hours to give 1.73 g of white powdery crystals (yield 80%).

Melting point: 209°–211° C.

IR (KBr): 3400, 1592 cm$^{-1}$ $^1$H-NMR (DMSO-d$_6$) δ: 3.81 (3H, s), 7.31 (1H, t, J=7.7 Hz), 7.34 (2H, d, J=7.7 Hz), 7.48 (2H, t, J=7.7 Hz), 8.67 (1H, s)

EXAMPLE 86

2-(4-Cyanophenylthio)-6-methyl-1,2,4-triazolo[1,5-a]-1,3,5-triazine-7(15H)-thione The synthesis method of Example 55 was applied. The compound (373 mg) obtained in Example 40-(2) and diethoxymethyl acetate (8 ml) were used as reagents. The mixture was reacted at 90° C. for 2 hours to give 252 mg of white crystals (yield 66%).

Melting point: 212°–218° C.

IR (KBr): 3400, 3080, 2220, 1598 cm$^{-1}$ $^1$H-NMR (DMSO-d$_6$) δ: 3.82 (3H, s), 7.78 (2H, d, J=8.3 Hz), 7.90 (2H, d, J=8.3 Hz), 8.88 (1H, s)

EXAMPLE 87

2-Benzyl-6-methyl-1,2,4-triazolo[1,5-a]-1,3,5-triazine-7(6H)-thione

The synthesis method of Example 55 was applied. The compound (1.31 g) obtained in Example 41-(2) and diethoxymethyl acetate (8 ml) were used as reagents. The mixture was reacted at 90° C. for 1 hour to give 1.30 g of white powdery crystals (yield 94%).

Melting point: 185°–187° C.

IR (KBr): 3010, 1590, 1556 cm$^{-1}$ $^1$H-NMR (DMSO-d$_6$) δ: 3.80 (3H, s), 4.16 (2H, s), 7.23 (1H, t, J=6.7 Hz), 7.28–7.36 (4H, m), 8.81 (1H, s)

EXAMPLE 88

2-(4-Chlorostyryl)-6-methyl-1,2,4-triazolo[1,5-a]-1,3,5-triazine-7(6H)-thione

The synthesis method of Example 55 was applied. The compound (1.14 g) obtained in Example 42-(3) and diethoxymethyl acetate (8 ml) were used as reagents. The mixture was reacted at 85° C. for 1.5 hours to give 1.12 g of white powdery crystals (yield 95%).

Melting point: >300° C.

IR (KBr): 3010, 1640, 1582, 1562 cm$^{-1}$ $^1$H-NMR (trifluoroacetic acid-d) δ: 4.11 (3H, s), 7.19 (1H, d, J=16.6 Hz), 7.47 (2H, d, J=8.5 Hz), 7.61 (2H, d, J=8.5 Hz), 7.98 (1H, d, J=16.6 Hz), 8.88 (1H, s)

EXAMPLE 89

6-Methyl-2-(2-phenylethynyl)-1,2,4-triazolo[1,5-a]-1,3,5-triazine-7(6H)-thione

The synthesis method of Example 55 was applied. The compound (8.0 mg) obtained in Example 43-(3) and diethoxymethyl acetate (0.2 ml) were used as reagents. The mixture was reacted at 1 0° C. for 1.5 hours to give 6.8 mg of pale-yellow crystals (yield 82%).

Melting point: 290°–295° C.

IR (KBr): 3380, 2220, 1572, 1500 cm$^{-1}$ $^1$H-NMR (DMSO-d$_6$) δ: 3.84 (3H, s), 7.48–7.58 (3H, m), 7.72 (2H, d, J=6.9 Hz), 8.91 (1H, s)

EXAMPLE 90

2-(4-Chlorophenyl)-6-n-propyl-1,2,4-triazolo[1,5-a]-1,3,5-triazine-7(6H)-thione

The synthesis method of Example 55 was applied. The compound (280 mg) obtained in Example 44 and diethoxymethyl acetate (6.0 g) were used as reagents. The mixture was reacted at 100° C. for 2.5 hours to give 207 mg of white crystals (yield 71%).

Melting point: 214°–216° C.

IR (KBr): 3400, 2950, 1735, 1640, 1590, 1560 cm$^{-1}$ $^1$H-NMR (DMSO-d$_6$) δ: 0.95 (3H, t, J=7.4 Hz), 1.86 (2H, sext, J=7.4 Hz), 4.40 (2H,t, J=7.4 Hz), 7.64 (2H, d, J=8.5 Hz), 8.19 (2H, d, J=8.5 Hz), 8.90 (1H, s)

EXAMPLE 91

2-(4-Chlorophenyl)-6-n-pentyl-1,2,4-triazolo[1,5-a]-1,3,5-triazine-7(6H)-thione

The synthesis method of Example 55 was applied. The compound (1.72 g) obtained in Example 45-(2) and diethoxymethyl acetate (15.6 g) were used as reagents. The mixture was reacted at 90° C. for 2 hours to give 1.13 g of white crystals (yield 66%).

Melting point: 197°–199° C.

IR (KBr): 3400, 2900, 1590, 1565, 1555 cm$^{-1}$ $^1$H-NMR (DMSO-d$_6$) δ: 0.89 (3H, t, J=6.7 Hz), 1.12–1.61 (4H, m), 1.68–2.11 (2H, m), 4.43 (2H, t, J=7.3 Hz), 7.64 (2H, d, J=8.5 Hz), 8.19 (2H, d, J=8.5 Hz), 8.91 (1H, s)

EXAMPLE 92

2-(4-Chlorophenyl)-6-isopropyl-1,2,4-triazolo[1,5-a]-1,3,5-triazine-7(6H)-thione The synthesis method of Example 55 was applied. The compound (1.07 g) obtained in Example 46-(2) and diethoxymethyl acetate (8.20 g) were used as reagents. The mixture was reacted at 90° C. for 2 hours to give 958 mg of white crystals (yield 86%).

Melting point: 230°–232° C.

IR (KBr): 3400, 3050, 1595, 1550 cm$^{-1}$ $^1$H-NMR (DMSO-d$_6$) δ: 1.52 (6H, d, J=6.8 Hz), 5.76 (1H, hept, J=6.8 Hz), 7.64 (2H,d, J=8.5 Hz), 8.20 (2H, d, J=8.5 Hz), 8.94 (1H, s)

EXAMPLE 93

6-n-Propyl-1,2,4-triazolo[1,5-a]-1,3,5-triazine-7(6H)-thione

The synthesis method of Example 55 was applied. A 2:1 mixture (3.52 g) obtained in Example 47 of 5-amino-1-[n-propylamino(thiocarbonyl)]-1H-1,2,4-triazole and 3-amino-1-[n-propylamino(thiocarbonyl)]-1H-1,2,4-triazole and diethoxymethyl acetate (20 ml) were used as reagents. The mixture was reacted at 75° C. for 2 hours to give 2.22 g of white crystals (yield 95% from 5-amino-1-[n-propylamino(thiocarbonyl)]-1H-1-1,2,4-triazole), which were then subjected to recrystallization from water to give white crystals.

Melting point: 168°–169° C.

IR (KBr): 3050, 2970, 1587, 1558 cm$^{-1}$ $^1$H-NMR (DMSO)-d$_6$) δ: 0.94 (3H, t, J=7.5 Hz), 1.85 (2H, sext, J=7.5 Hz), 4.39 (2H, dd, J=7.5, 6.3 Hz), 8.57 (1H, s), 8.88 (1H, s)

EXAMPLE 94

2-(4-Chlorophenyl)-6-methyl-1,2,4-triazolo[1,5-a]-1,3,5-triazine-7(6H)-thione

The synthesis method of Example 55 was applied. The compound (1.00 g) obtained in Example 52 and diethoxymethyl acetate (5.0 ml) were used as reagents. The mixture was reacted at 100° C. for 6 hours to give 292 mg of white crystals (yield 28%).

Melting point: 283°–285° C.

IR (KBr): 1740, 1595, 1550 cm$^{-1}$ $^1$H-NMR (DMSO-d$_6$) δ: 3.56 (3H, s), 7.62 (2H, d, J=8.5 Hz), 8.16 (2H, d, J=8.5 Hz), 8.64 (1H, s)

EXAMPLE 95

6-Methyl-1,2,4-triazolo[1,5-a]-1,3,5-triazine-7(6H)-thione

The synthesis method of Example 55 was applied. The compound (2.00 g) obtained in Example 53 and diethoxymethyl acetate (20 ml) were used as reagents. The mixture was reacted at 60° C. for 0.5 hour and 243 mg of crystals were collected by filtration (yield 11%). The crystals were subjected to recrystallization from ethanol to give white crystals.

Melting point: 223°–226° C.

IR (KBr): 3090, 3060, 1758, 1598, 1553 cm$^{-1}$ $^1$H-NMR (DMSO-d$_6$) δ: 3.53(3H, s), 8.42(1H, s), 8.61 (1H, s)

EXAMPLE 96

2-(4-Chlorophenyl)-5,6-dimethyl-1,2,4-triazolo[1,5-a]-1,3,5-triazine-7(6H)-thione The reaction mixture of the compound (1.50 g) obtained in Example 4-(3), triethyl orthoacetate (10 ml) and acetic acid (0.5 ml) was stirred at 140° C. for 5 hours. After the reaction, the mixture was cooled to room temperature and the resulting crystals were collected by filtration. The obtained crystals were subjected to silica gel column chromatography (chloroform-methanol) to give 910 mg of white crystals (yield 56%).

Melting point: >300° C.

IR (KBr): 1590 cm$^{-1}$ $^1$H-NMR (trifluoroacetic acid-d) δ: 2.96 (3H, s), 4.19(3H, s), 7.66 (2H, d, J=8.4 Hz), 8.10 (2H, d, J=8.4 Hz)

EXAMPLE 97

2-(4-Chlorophenyl)-6-methyl-5-phenyl-1,2,4-triazolo[1,5-a]-1,3,5-triazine-7(6H)-thione The synthesis method of Example 96 was applied. The compound (1.61 g) obtained in Example 4-(3), trimethyl orthobenzoate (4.0 ml) and acetic acid (0.2 ml) were used as reagents. The mixture was stirred at 150° C. for 2 hours. After the reaction, the resulting crystals were collected by filtration and subjected to silica gel column chromatography (chloroform) to give 1.33 g of white crystals (yield 63%).

Melting point: 267°–270° C.

IR (KBr): 1580., 1577 cm$^{-1}$ $^1$H-NMR (DMSO-d$_6$) δ: 3.75 (3H, s), 7.59–7.67 (5H, m), 7.74 (2H, d, J=6.4 Hz), 8.10(2H,d,J=8.4 Hz)

EXAMPLE 98

5,6-Dimethyl-1,2,4-triazolo[i,5-a]-1,3,5-triazine-7(6H)-thione

The synthesis method of Example 96 was applied. The compound (2.00 g) obtained in Example 29 and triethyl orthoacetate (13 ml) were used as reagents. The mixture was stirred at 145° C. for 3 hours. After the reaction, the resulting crystals were collected by filtration to give 497 mg of a pale-brown solid. The filtrate was concentrated under reduced pressure and applied to silica gel column chromatography (chloroform-methanol). The previously-obtained crystals were combined to give 605 g of a solid (total yield 26%). The solid was subjected to recrystallization from chloroform-hexane to give white fine fiber-like crystals.

Melting point: 147°–148° C.

IR (KBr): 3530, 3430, 1586 cm$^{-1}$ $^1$H-NMR (DMSO-d$_6$) δ: 3.71 (3H, s), 3.96 (3H, s), 8.51 (1H, s)

EXAMPLE 99

6-Methyl-5-phenyl-1,2,4-triazolo[1,5-a]-1,3,5-triazine-7(6H)-thione

The synthesis method of Example 96 was applied. The compound (1.50 g) obtained in Example 29 and trimethylorthobenzoate (5.0 ml) were used. The mixture was reacted at 150° C. for 2 hours. The resulting crystals were collected by filtration and purified by a method similar to the method of Example 98, whereby crystals (1.53 mg) were obtained (yield 66%). The crystals were recrystallized from methanol to give colorless transparent plate crystals.

Melting point: 246°–248° C.

IR (KBr): 3410, 1591 cm$^{-1}$ $^1$H-NMR (DMSO-d$_6$) δ: 3.73 (3H, s), 7.57–7.66 (3H, m), 7.70–7.74 (2H, m), 8.61 (1H, s)

To establish the effectiveness of said triazole derivatives and salts thereof, the data of the pharmacological tests of the typical compounds of the present invention are shown in the following.

Experimental Example 1

Eosinophilia-Inhibitory Activity (1) Test method

Rats weighing 250°–350 g were used (5 per group). The test method was a partial modification of the method reported by B. A. Spicer et al (Br. J. Pharmacol (1990), 101, 821). Sephadex G-200 having a particle size of 40°–120 micron was suspended in isotonic saline at 0.5 mg/ml and boiled for 5 hours on the administration day to allow swelling. The suspension was administered to the rats from the tail vein by 1 ml at day 0, day 2 and day 5. At the 7th day from the initiation of the administration, the rats were anesthetized with 25% urethane (5 ml/kg) and fixed at a dorsal position. A cut down tube was inserted into trachea and applied with a three-way cock at its end. A 5 ml plastic syringe was set on one end of the three-way cock, a 5 ml plastic syringe containing 6 units/ml heparin-PBS (37° C.) was set on the other end and the liquid was injected. Using the empty 5 ml plastic syringe, the liquid was inserted or sucked out three times. This set of operations were repeated three times and the liquid obtained was preserved on ice as a bronchovesicular washing (ca 12 ml). The obtained washing was centrifuged [1000 rpm (150 g)×5 min, 4° C.] and the supernatant thereof was removed by decantation. The residue was re-suspended in 500 µl of RPMI-1640 medium. The total leukocytes in the suspension was counted by Colter counter (Sysmex, MICROCELLCOUNTER CC-120). Hinkelmann's Solution (900 µl), which is an eosinophil count reagent, was added to 100 µl of the re-suspension for staining (1:9), and the proportion of eosinophil count relative to the leukocyte count in one microscopic field was determined using an optical microscope (NIKON, BIO-PHOT Type 104). The drug (test compound) was intraperitoneally administered in a dose of 30 mg/kg 10 minutes prior to the respective administration of Sephadex. The control group was administered with an isotonic saline containing 1% Tween 80 and 1% dimethyl sulfoxide instead of the drug.

(2) Test compounds

Compound A: 5-amino-1-[methylamino(thiocarbonyl)]-1H-1,2,4-triazole

Compound B: 3,5-diamino-1-[methylamino(thiocarbonyl)]-1H-1,2,4-triazole

Compound C: 5-amino-3-(4-cyanophenyl)-1-[methylamino(thiocarbonyl)]-1H-1,2,4-triazole Compound D: 5-amino-3-(4-chlorophenyl)-1-[methylamino(thiocarbonyl)]-1H-1,2,4-triazole Compound E: 5-amino-3-(4-methoxyphenyl)-1-[methylamino(thiocarbonyl)]-1H-1,2,4-triazole Compound F: 6-methyl-1,2,4-triazolo[1,5-a]-1,3,5-triazine-7(6H)-thione Compound G: 2-(4-cyanophenyl)-6-methyl-1,2,4-triazolo[1,5-a]-1,3,5-triazine-7(6H)-thione Compound H: 2-(4-chlorophenyl)-6-methyl-1,2,4-triazolo[1,5-a]-1,3,5-triazine-7(6H)-thione Compound I: 5-amino-3-(3-chlorophenyl)-1-[methylamino(thiocarbonyl)]-1H-1,2,4-triazole Compound J: 5-amino-3-(4-fluorophenyl)-1-[methylamino(thiocarbonyl)]-1H-1,2,4-triazole Compound K: 5-amino-3-(4-bromophenyl)-1-[methylamino(thiocarbonyl)]-1H-1,2,4-triazole Compound L: 5-amino-1-[methylamino(thiocarbonyl)]-3-(4-trifluoromethylphenyl)-1H-1,2,4-triazole Compound M: 5-amino-3-(4-phenylphenyl)-1-[methylamino(thiocarbonyl)]-1H-1,2,4-triazole Compound N: 5-amino-3-(2,4-dichlorophenyl)-1-[methylamino(thiocarbonyl)]-1H-1,2,4-triazole Compound O: 5-amino-3-(3,4-dichlorophenyl)-1-[methylamino(thiocarbonyl)]-1H-1,2,4-triazole Compound P: 5-amino-3-(4-chloro-2-methoxyphenyl)-1-[methylamino(thiocarbonyl)]-1H-1,2,4-triazole Compound Q: 2-(4-fluorophenyl)-6-methyl-1,2,4-triazolo[1,5-a]-1,3,5-triazine-7(6H)-thione Compound R: 2-(4-bromophenyl)-6-methyl-1,2,4-triazolo[1,5-a]-1,3,5-triazine-7(6H)-thione Compound S: 6-methyl-2-(4-trifluoromethylphenyl)-1,2,4-triazolo[1,5-a]-1,3,5-triazine-7(6H)-thione Compound T: 6-methyl-2-(4-phenylphenyl)-1,2,4-triazolo[1,5-a]-1,3,5-triazine-7(6H)-thione Compound U: 2-(2,4-dichlorophenyl)-6-methyl-1,2,4-triazolo[1,5-a]-1,3,5-triazine-7(6H)-thione Compound V: 2-(3,4-dichlorophenyl)-6-methyl-1,2,4-triazolo[1,5-a]-1,3,5-triazine-7(6H)-thione (3) Test results Eosinophilia-inhibitory activity was calculated from the following formula. The results are shown in Table 1.

TABLE 1

$$\text{Inhibition (\%)} = \left(1 - \frac{\text{proportion of eosinophil count relative to leukocyte count in group administered with test drug}}{\text{proportion of eosinophil count relative to leukocyte count in control}}\right) \times 100$$

| Test Compound | Inhibition (%) |
| --- | --- |
| Compound A | 88 |
| Compound B | 53 |
| Compound C | 87 |
| Compound D | 87 |
| Compound E | 70 |
| Compound F | 58 |
| Compound G | 79 |
| Compound H | 83 |
| Compound I | 70 |
| Compound J | 80 |
| Compound K | 90 |
| Compound L | 88 |
| Compound M | 85 |
| Compound N | 90 |
| Compound O | 88 |
| Compound P | 85 |
| Compound Q | 82 |
| Compound R | 88 |
| Compound S | 89 |
| Compound T | 80 |
| Compound U | 85 |
| Compound V | 87 |

Experimental Example 2:

Inhibitory action on T lymphocyte activation stimulated by concanavalin A (1) Test method The test was performed according to the method of Mishell, B. B. et al ["Cell Proliferation" in Selected Methods in Cellular Immunology, V, XXiX, W. H. Freeman Co., San Francisco, Calif. pp. 153–160, 1980].

T lymphocytes were isolated from mouse thymus by a conventional method and suspended in DMEM. The cells ($5 \times 10^6$ cells/ml) were incubated at 37° C. for 12 hours in the presence of 3 μg/ml of concanavalin A. The test drug was added at 10 μM under these incubation conditions. After 12 hours of incubation, 2 μCi [3H]thymidine was added to each well and the well was incubated for 48 hours. After the incubation, the thymidine uptake was determined by a scintillation counter. The growth-inhibitory activity is shown in minus percentage figures relative to the figure of the control group.

(2) Test compounds

Compound (1): 5-amino-3-(4-chlorophenyl)-1-[methylamino(thiocarbonyl)]-1H-1,2,4-triazole Compound (2): 5-<amino-3-(4-bromophenyl)-1-[methylamino(thiocarbonyl)]-1H-1,2,4-triazole Compound (3): 5-amino-1-|methylamino(thiomethylphenyl]-(4-trifluoromethylphenyl]-1H-1,2,4-triazole Compound (4): 2-(4-chlorophenyl)-6-methyl-1,2,4-triazolo[1,5-a]-1,3,5-triazine-7(6H)-thione Compound (5): 2-(4-bromophenyl)-6-methyl-1,2,4-triazolo[1,5-a]-1,3,5-triazine-7(6H)-thione Compound (6): 6-methyl-2-(4-trifluoromethylphenyl)-1,2,4-triazolo-[1,5-a]-1,3,5-triazine-7(6H)-thione Compound (7): 2-(3,4-dichlorophenyl)-6-methyl-1,2,4-triazolo[1,5-a]-1,3,5-triazine-7(6H)-thione Compound (8): 2-(2,4-dichlorophenyl)-6-methyl-1,2,4-triazolo[1,5-a]-1,3,5-triazine-7(6H)-thione (3) Test results Test compounds Compound (1)—52%
Compound (2)—35%
Compound (3)—37%
Compound (4)—60%
Compound (5)—58%
Compound (6)—36%
Compound (7)—40%
Compound (8)—22%

Example (formulation example)

| Tablet | | |
| --- | --- | --- |
| (1) | Compound (I) hydrochloride | 10 mg |
| (2) | Fine particle No. 209 for direct compression (manufactured by Fuji Kagaku) | 46.6 mg |
| | Magnesium aluminometasilicate | 20% |
| | Corn starch | 30% |
| | Lactose | 50% |
| (3) | Crystalline cellulose | 24.0 mg |
| (4) | Calcium carboxylmethylcellulose | 4.0 mg |
| (5) | Magnesium stearate | 0.4 mg |

(1), (3) and (4) were respectively passed through a 100 mesh sieve in advance. (1), (3), (4) and (2) were dried to a certain water content, and mixed in the above-mentioned weight ratio in a mixer. The homogeneous powder mixture was added with (5) and mixed for a short time (30 sec. The powder mixture was compressed (pounder: 6.3 mmφ, 6.0 mmR) to give tablets weighing 85 mg per tablet.

These tablets may be applied with a conventionally-used enteric film coating (e.g. polyvinylacetal diethylaminoacetate) or food coloring where necessary.

| Capsules | |
| --- | --- |
| (1) Compound (III) hydrochloride | 50 g |
| (2) Lactose | 935 g |
| (3) Magnesium stearate | 15 g |

The above ingredients were respectively weighed and homogeneously mixed. The powder mixture was packed by 200 mg in hard gelatin capsules.

| Injections | |
|---|---|
| (1) Compound (I) hydrochloride | 5 mg |
| (2) Glucose | 100 mg |
| (3) Physiological saline | 10 ml |

A mixed solution of the above ingredients was filtered through a membrane filter and filtered again for sterilization. The filtrate was aseptically dispensed to vials, and the vials were filled with a nitrogen gas to give intravenous injections.

The agent for the prophylaxis and treatment of immune-related diseases, in particular, immunosuppressant, the agent for the prophylaxis and treatment of allergic diseases, the agent for the prophylaxis and treatment of eosinophil-related diseases, the eosinophilia inhibitor and the novel triazole derivative of the present invention all have eosinophilia-inhibitory action and lymphocyte activation-inhibitory action. They are low toxic and persistent in action. They are particularly effective in the treatment of accumulation and activation of eosinophil and lymphocytes, inflammatory respiratory tract diseases, eosinophil-related diseases such as eosinophilia, and immune-related diseases.

What is claimed is:

1. A triazole derivative of the formula (I')

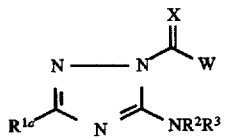

(I')

wherein

X is an oxygen atom or a sulfur atom;
W is —$NR^{4a}R^{5a}$;
$R^{1a}$ is —$NR^{10}R^{11}$, —$N=R^{13}$ or a group of the formula (II)

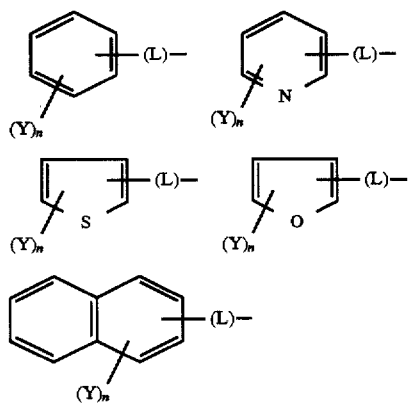

(II)

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl,
L is a direct bond, an oxygen atom, a sulfur atom, an alkylene, a vinylene or an ethynylene, and n is an integer of 1 to 3,
provided that when n is 2 or 3, Y may be the same or different; and $R^2$ and $R^3$ are the same or different and each is a hydrogen atom or a lower alkyl,
wherein $R^{4a}$ and $R^{5a}$ are the same or different and each is a hydrogen atom, or a lower alkyl, provided that $R^{4a}$ and $R^{5a}$ are not hydrogen atom at the same time, $R^{10}$ and $R^{11}$ are the same or different and each is a hydrogen atom, an optionally substituted benzoyl, an optionally substituted phenyl, a lower alkylcarbonyl or —$COCOOR^{17}$, $R^{17}$ is a lower alkyl, provided that when all of $R^2$, $R^3$ and $R^{4a}$ are hydrogen atom and $R^{5a}$ is a lower alkyl, $R^{10}$ and $R^{11}$ are not hydrogen atom at the same time, $R^{13}$ is an optionally substituted methylene, $R^{14}$ and $R^{15}$ are the same or different and each is a hydrogen atom, a lower alkyl, —$COCOOR^{17}$ or —$CSNHR^{18}$ and $R^{18}$ is a lower alkyl, or a pharmaceutically acceptable salt thereof.

2. A method for the prophylaxis or treatment of immune-related diseases, comprising administering to a mammal a compound of the formula (I)

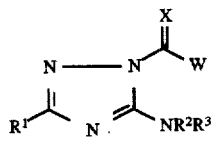

(I)

wherein
X is an oxygen atom or a sulfur atom;
W is —$NR^4R^5$ or —$SR^6$;
$R^1$ is a hydrogen atom, a lower alkyl, —$NR^{10}R^{11}$, —$N=R^{13}$ or a group of the formula (II)

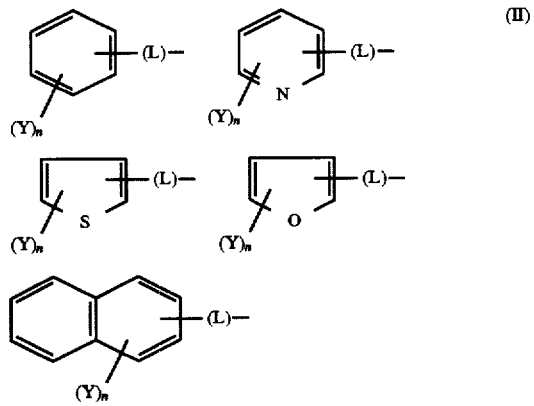

(II)

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl,
L is a direct bond, an oxygen atom, a sulfur atom, an alkylene, a vinylene or an ethynylene, and n is an integer of 1 to 3,
provided that when n is 2 or 3, Y may be the same or different; and
$R^2$ and $R^3$ are the same or different and each is a hydrogen atom or a lower alkyl;
wherein $R^4$ and $R^5$ are the same or different and each is a hydrogen atom, a lower alkyl, a cycloalkyl, or a phenyl, $R^6$ is a lower alkyl, $R^{10}$ and $R^{11}$ are the same or different and each is a hydrogen atom, an optionally substituted benzoyl, an optionally substituted phenyl,
a lower alkylcarbonyl or —$COCOOR^{17}$, $R^{17}$ is a lower alkyl, $R^{13}$ is an optionally substituted methylene, $R^{14}$ and $R^{15}$ are the same or different and each is a hydrogen atom, a lower alkyl, —COCOOR$^{17}$ or —CSNHR$^{18}$, and $R^{18}$ is a lower alkyl, or a pharmaceutically acceptable salt thereof.

3. A method for the prophylaxis or treatment of eosinophil-related diseases, comprising administering to a mammal a compound of the formula (I)

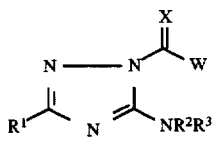
(I)

wherein

X is an oxygen atom or a sulfur atom;

W is —NR$^4$R$^5$ or —SR$^6$;

$R^1$ is a hydrogen atom, a lower alkyl, —NR$^{10}$R$^{11}$, —N=R$^{13}$ or a group of the formula (II)

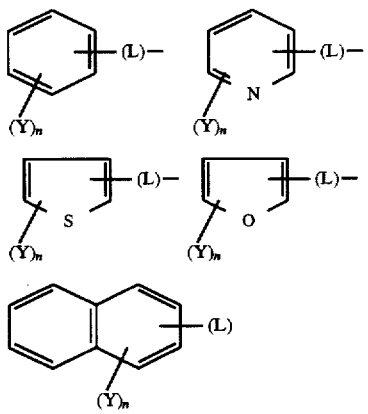
(II)

wherein Y is a hydrogen atom, a lower alkyl, a lower alkoxy, a halogen, a cyano, a nitro, a lower alkyl substituted by halogen, —NR$^{14}$R$^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl;

wherein $R^4$ and $R^5$ are the same or different and each is a hydrogen atom, a lower alkyl, a cycloalkyl, or a phenyl, $R^6$ is a lower alkyl, $R^{10}$ and $R^{11}$ are the same or different and each is a hydrogen atom, an optionally substituted benzoyl, an optionally substituted phenyl;

a lower alkylcarbonyl or —COCOOR$^{17}$, $R^{17}$ is a lower alkyl, $R^{13}$ is an optionally substituted methylene, $R^{14}$ and $R^{15}$ are the same or different and each is a hydrogen atom, a lower alkyl, —COCOOR$^{17}$ or —CSNHR$^{18}$, and $R^{18}$ is a lower alkyl, or a pharmaceutically acceptable salt thereof.

4. A method according to claim 2, wherein the immune-related disease is an eosinophil-related disease.

5. A method according to claim 2, wherein the administering is accomplished by an oral route.

6. The method according to claim 2, wherein the administering is accomplished by a parenteral route.

7. A method according to claim 2, wherein administering is accomplished by topical application.

8. A method according to claim 2, wherein the administering is accomplished by making said compound available to the mammal by inhalation.

9. The method according to claim 2, wherein the immune-related disease is an allergic disease.

10. The method according to claim 2, wherein the administering is accomplished by intravenous injection.

11. A method for suppressing activation of an eosinophil or a lymphocyte comprising treating said eosinophil or lymphocyte with a compound of formula (I)

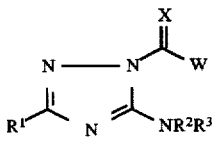
(I)

wherein

X is an oxygen atom or a sulfur atom;

W is —NR$^4$R$^5$ or —SR$^6$;

$R^1$ is a hydrogen atom, a lower alkyl, —NR$^{10}$R$^{11}$, —N=R$^{13}$ or a group of the formula (II)

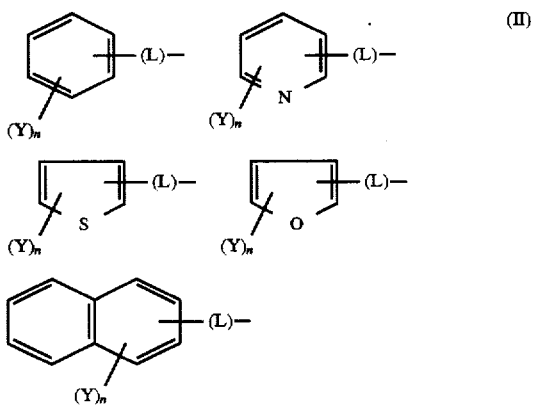
(II)

wherein Y is a hydrogen atom, a lower alkyl, a lower alkoxy, a halogen, a cyano, a nitro, a lower alkyl substituted by halogen, —NR$^{14}$R$^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl;

wherein $R^4$ and $R^5$ are the same or different and each is a hydrogen atom, a lower alkyl, a cycloalkyl, or a phenyl, $R^6$ is a lower alkyl, $R^{10}$ and $R^{11}$ are the same or different and each is a hydrogen atom, an optionally substituted benzoyl, an optionally substituted phenyl, a lower alkylcarbonyl or —COCOOR$^{17}$, $R^{17}$ is a lower alkyl, $R^{13}$ is an optionally substituted methylene, $R^{14}$ and $R^{15}$ are the same or different and each is a hydrogen atom, a lower alkyl, —COCOOR$^{17}$ or —CSNHR$^{18}$, and $R^{18}$ is a lower alkyl, or a pharmaceutically acceptable salt thereof.

12. The method of claim 2 wherein, in the formula (I), $R^1$ is a group of the formula (II)

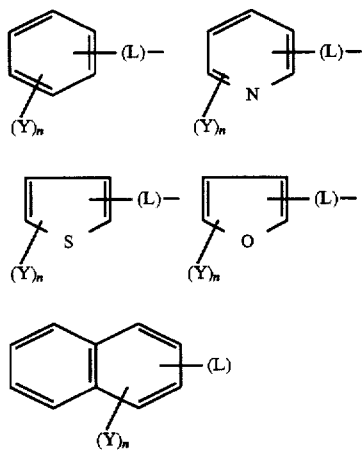

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different.

13. The method of claim 3 wherein, in the formula (I), $R^1$ is a group of the formula (II)

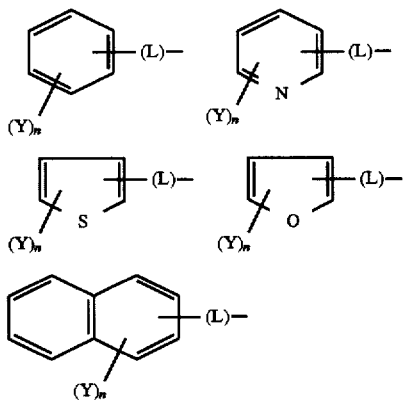

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different.

14. A method for suppressing an immune reaction in a mammal which comprises administering to the mammal a compound of the formula (I)

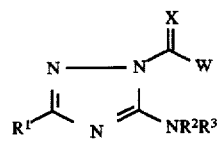

wherein

X is an oxygen atom or a sulfur atom;

W is —$NR^4R^5$ or —$SR^6$;

$R^1$ is a hydrogen atom, a lower alkyl, —$NR^{10}R^{11}$, —$N=R^{13}$ or a group of the formula (II)

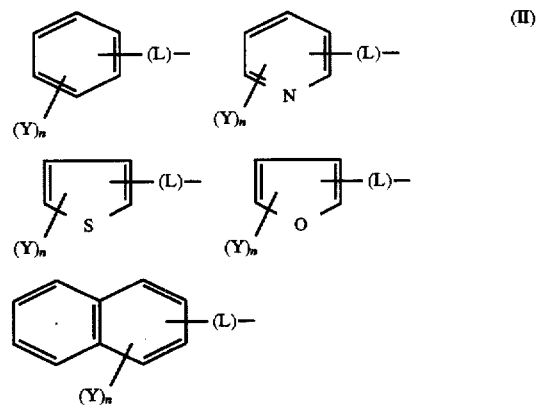

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl;

wherein $R^4$ and $R^5$ are the same or different and each is a hydrogen atom, a lower alkyl, a cycloalkyl, or a phenyl, $R^6$ is a lower alkyl, $R^{10}$ and R are the same or different and each is a hydrogen atom, an optionally substituted benzoyl, an optionally substituted phenyl, a lower alkylcarbonyl or —$COCOOR^{17}$ $R^{17}$ is a lower alkyl, $R^{13}$ is an optionally substituted methylene, $R^{14}$ and $R^{15}$ are the same or different and each is a hydrogen atom, a lower alkyl, —$COCOOR^{17}$ or —$CSNHR^{18}$, and $R^{18}$ is a lower alkyl, or a pharmaceutically acceptable salt thereof.

15. The method of claim 4 wherein, in the formula (I), $R^1$ is a group of the formula (II)

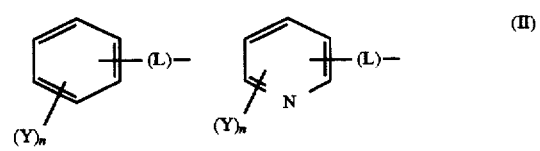

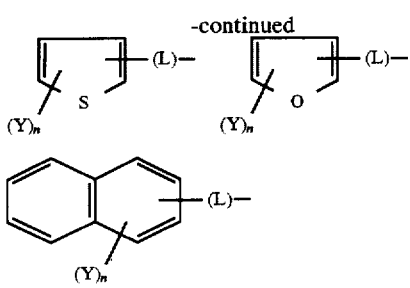

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different.

16. A method for suppressing increase of eosinophils in a mammal by administration of a compound of the formula (I)

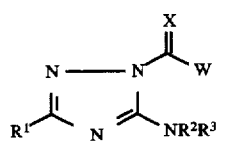

wherein

X is an oxygen atom or a sulfur atom;

W is —$NR^4R^5$ or —$SR^6$;

$R^1$ is a hydrogen atom, a lower alkyl, —$NR^{10}R^{11}$, —$N=R^{13}$ or a group of the formula (II)

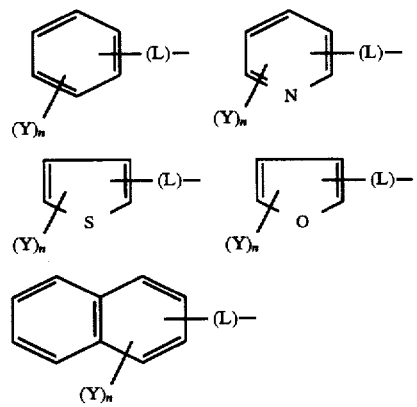

wherein Y is a hydrogen atom, a lower alkyl, a lower alkoxy, a halogen, a cyano, a nitro, a lower alkyl substituted by halogen, —$NR^{14}R^5$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different; and $R^2$ and $R^3$ are the same or different and each is a hydrogen atom or a lower alkyl;

wherein $R^4$ and $R^5$ are the same or different and each is a hydrogen atom, a lower alkyl, a cycloalkyl, or a phenyl, $R^6$ is a lower alkyl, $R^{10}$ and $R^{11}$ are the same or different and each is a hydrogen atom, an optionally substituted benzoyl, an optionally substituted phenyl, a lower-alkylcarbonyl or —$COCOOR^{17}$, $R^{17}$ is a lower alkyl, $R^{13}$ is an optionally substituted methylene, $R^{14}$ and $R^{15}$ are the same or different and each is a hydrogen atom, a lower-alkyl, —$COCOOR^{17}$ or —$CSNHR^{18}$, and $R^{18}$ is a lower alkyl, or a pharmaceutically acceptable salt thereof.

17. The method of claim 35 wherein, in the formula (I), $R^1$ is a group of the formula (II)

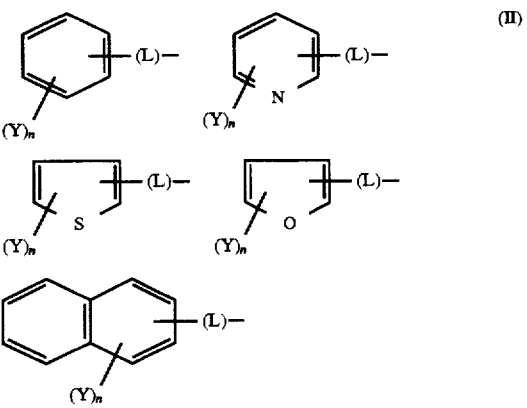

wherein Y is a hydrogen atom, a lower alkyl, a lower alkoxy, a halogen, a cyano, a nitro, a lower alkyl substituted by halogen, —$NR^{14}R^{15}$, a tetrazolyl, an optionally substituted phenyl, a hydroxy or a carboxyl, L is a direct bond, an oxygen atom, a sulfur atom, an alkylene, a vinylene or an ethynylene, and n is an integer of 1 to 3, provided that when n is 2 or 3, Y may be the same or different.

* * * * *